United States Patent
Lai

(10) Patent No.: US 10,004,741 B2
(45) Date of Patent: *Jun. 26, 2018

(54) SOLID FORMS OF AN EPIDERMAL GROWTH FACTOR RECEPTOR KINASE INHIBITOR

(71) Applicant: Celgene CAR LLC, Pembroke (BM)

(72) Inventor: Mei Lai, Longmont, CO (US)

(73) Assignee: Celgene CAR LLC, Pembroke (BM)

( * ) Notice: Subject to any disclaimer, the term of this patent is extended or adjusted under 35 U.S.C. 154(b) by 0 days. days.

This patent is subject to a terminal disclaimer.

(21) Appl. No.: 15/401,663

(22) Filed: Jan. 9, 2017

(65) Prior Publication Data

US 2017/0281623 A1 Oct. 5, 2017

Related U.S. Application Data

(63) Continuation of application No. 14/734,279, filed on Jun. 9, 2015, now Pat. No. 9,539,255, which is a continuation of application No. 13/801,060, filed on Mar. 13, 2013, now Pat. No. 9,056,839.

(60) Provisional application No. 61/611,376, filed on Mar. 15, 2012.

(51) Int. Cl.
*A61K 31/506* (2006.01)
*C07D 239/48* (2006.01)

(52) U.S. Cl.
CPC .......... *A61K 31/506* (2013.01); *C07D 239/48* (2013.01)

(58) Field of Classification Search
CPC ... A61K 31/497; A61K 31/506; C07D 239/48
See application file for complete search history.

(56) References Cited

U.S. PATENT DOCUMENTS

| | | | |
|---|---|---|---|
| 3,609,152 A | 9/1971 | Hess et al. |
| 4,337,341 A | 6/1982 | Zimmerman |
| 4,879,303 A | 11/1989 | Davison et al. |
| 5,958,935 A | 9/1999 | Davis et al. |
| 6,093,716 A | 7/2000 | Davis et al. |
| 6,114,333 A | 9/2000 | Davis et al. |
| 6,127,376 A | 10/2000 | Davey et al. |
| 6,160,010 A | 12/2000 | Uckun et al. |
| 6,262,088 B1 | 7/2001 | Phillips |
| 6,469,168 B1 | 10/2002 | Ratzne Simonek et al. |
| 6,579,983 B1 | 6/2003 | Batchelor et al. |
| 6,593,326 B1 | 7/2003 | Bradbury et al. |
| 6,838,464 B2 | 1/2005 | Pease et al. |
| 6,908,906 B2 | 6/2005 | Takita et al. |
| 6,939,874 B2 | 9/2005 | Harmange et al. |
| 7,060,827 B2 | 6/2006 | Singh et al. |
| 7,122,542 B2 | 10/2006 | Singh et al. |
| 7,125,879 B2 | 10/2006 | Guillemont et al. |
| 7,176,212 B2 | 2/2007 | Breault et al. |
| 7,202,033 B2 | 4/2007 | Prescott et al. |
| 7,241,769 B2 | 7/2007 | Stadtmueller et al. |
| 7,282,504 B2 | 10/2007 | Armistead et al. |
| 7,329,671 B2 | 2/2008 | Singh et al. |
| 7,329,672 B2 | 2/2008 | Singh et al. |
| 7,332,484 B2 | 2/2008 | Singh et al. |
| 7,435,814 B2 | 10/2008 | Singh et al. |
| 7,452,879 B2 | 11/2008 | Singh et al. |
| 7,485,724 B2 | 2/2009 | Singh et al. |
| 7,491,732 B2 | 2/2009 | Li et al. |
| 7,498,435 B2 | 3/2009 | Singh et al. |
| 7,504,396 B2 | 3/2009 | Nunes et al. |
| 7,514,444 B2 | 4/2009 | Honigberg et al. |
| 7,514,445 B2 | 4/2009 | Freyne et al. |
| 7,514,446 B2 | 4/2009 | Davis-Ward et al. |
| 7,528,143 B2 | 5/2009 | Noronha et al. |
| 7,531,548 B2 | 5/2009 | Guillemont et al. |
| 7,550,460 B2 | 6/2009 | Singh et al. |
| 7,557,210 B2 | 7/2009 | Singh et al. |
| 7,582,648 B2 | 9/2009 | Singh et al. |
| 7,589,200 B2 | 9/2009 | Singh et al. |
| 7,642,351 B2 | 1/2010 | Singh et al. |
| 7,655,797 B2 | 2/2010 | Singh et al. |
| 7,718,662 B1 | 5/2010 | Chen et al. |
| 7,741,330 B1 | 6/2010 | Chen et al. |
| 7,803,939 B2 | 9/2010 | Singh et al. |
| 7,820,819 B2 | 10/2010 | Singh et al. |
| 7,858,633 B2 | 12/2010 | Li et al. |
| 7,884,111 B2 | 2/2011 | Argade et al. |
| 8,088,781 B2 | 1/2012 | Honigberg et al. |
| 8,338,439 B2 | 12/2012 | Singh et al. |
| 8,450,335 B2 | 5/2013 | Singh et al. |
| 8,501,751 B2 | 8/2013 | Honigberg et al. |
| 8,563,568 B2 | 10/2013 | Witowski et al. |

(Continued)

FOREIGN PATENT DOCUMENTS

| CN | 1501939 A | 6/2004 |
|---|---|---|
| CN | 102558149 A | 7/2012 |

(Continued)

OTHER PUBLICATIONS

U.S. Appl. No. 13/518,833, filed Jun. 22, 2012, Gray et al.
Adeyeye, Moji, Ed., Preformulation in Solid Dosage Form Development, Chapter 2.3, Informa Healthcare, 63-80 (2008).
Aliagas-Martin, I. et al., A class of 2,4-bisanilinopyrimidine Aurora A inhibitors with unusually high selectivity against Aurora B, J. Med. Chem. 52:3300-3307 (2009).
Andrulis, I. et al., Neu/ErbB-2 amplification identifies a poor-prognosis group of women with node-negative breast cancer, J Clin Oncol 16:1340-9 (1998).
Bamborough, P. et al., N-4-Pyrimidinyl-1H-indazol-4-amine inhibitors of Lck: Indazoles as phenol isosteres with improved pharmacokinetics, Bioorg. & Med. Chem. Lett. 17:4363-4368 (2007).
Bastin, R.J. et al., Salt Selection and Optimisation Procedures for Pharmaceutical New Chemical Entities, Organic Process Research & Development, 4: 427-435, (2000).

(Continued)

*Primary Examiner* — Alexander R Pagano
*Assistant Examiner* — Ebenezer Sackey
(74) *Attorney, Agent, or Firm* — Choatge, Hall & Stewart LLP; Kristen C. Buteau; Michael A. Shinall

(57) ABSTRACT

The present invention provides a solid form and composites thereof, which are useful as an inhibitor of EGFR kinases and which exhibit desirable characteristics for the same.

20 Claims, 66 Drawing Sheets

(56) References Cited

U.S. PATENT DOCUMENTS

| | | |
|---|---|---|
| 8,609,679 B2 | 12/2013 | Singh et al. |
| 8,710,222 B2 | 4/2014 | Singh et al. |
| 8,796,255 B2 | 8/2014 | Lee et al. |
| 8,975,249 B2 | 3/2015 | Lee et al. |
| 9,056,839 B2 * | 6/2015 | Lai .................. A61K 31/506 |
| 9,108,927 B2 | 8/2015 | Lai et al. |
| 9,375,431 B2 | 6/2016 | Lee et al. |
| 9,539,255 B2 * | 1/2017 | Lai .................. A61K 31/506 |
| 9,540,335 B2 | 1/2017 | Lai et al. |
| 9,867,824 B2 | 1/2018 | Lee et al. |
| 2004/0002395 A1 | 1/2004 | Poynor |
| 2004/0019067 A1 | 1/2004 | Armistead et al. |
| 2004/0023957 A1 | 2/2004 | Wang et al. |
| 2004/0077661 A1 | 4/2004 | Arbiser |
| 2005/0004125 A1 | 1/2005 | Freyne et al. |
| 2005/0014753 A1 | 1/2005 | Ding et al. |
| 2005/0085637 A1 | 4/2005 | Cheung et al. |
| 2005/0209221 A1 | 9/2005 | Nunes et al. |
| 2005/0272083 A1 | 12/2005 | Seshagiri |
| 2006/0030018 A1 | 2/2006 | Zuccola et al. |
| 2006/0079543 A1 | 4/2006 | Sum et al. |
| 2006/0084644 A1 | 4/2006 | Pal et al. |
| 2006/0084645 A1 | 4/2006 | Pal et al. |
| 2006/0100227 A1 | 5/2006 | Baenteli et al. |
| 2006/0148800 A1 | 7/2006 | Stadtmueller et al. |
| 2006/0160803 A1 | 7/2006 | Adams et al. |
| 2006/0247241 A1 | 11/2006 | Garcia-Echeverria et al. |
| 2006/0247262 A1 | 11/2006 | Baenteli et al. |
| 2006/0270694 A1 | 11/2006 | Wong |
| 2006/0293311 A1 | 12/2006 | Li et al. |
| 2007/0010668 A1 | 1/2007 | Davis-Ward et al. |
| 2007/0032493 A1 | 2/2007 | Foley et al. |
| 2007/0066658 A1 | 3/2007 | Chappell |
| 2007/0203161 A1 | 8/2007 | Argade et al. |
| 2007/0203162 A1 | 8/2007 | Li et al. |
| 2007/0259904 A1 | 11/2007 | Noronha et al. |
| 2008/0009484 A1 | 1/2008 | Argade et al. |
| 2008/0009494 A1 | 1/2008 | Li et al. |
| 2008/0021020 A1 | 1/2008 | Argade et al. |
| 2008/0027045 A1 | 1/2008 | Argade et al. |
| 2008/0039622 A1 | 2/2008 | Singh et al. |
| 2008/0058358 A1 | 3/2008 | Luecking et al. |
| 2008/0076921 A1 | 3/2008 | Honigberg et al. |
| 2008/0132504 A1 | 6/2008 | Garcia-Echeverria et al. |
| 2008/0139582 A1 | 6/2008 | Honigberg et al. |
| 2008/0167330 A1 | 7/2008 | Luecking et al. |
| 2008/0176866 A1 | 7/2008 | Jautelat et al. |
| 2008/0182852 A1 | 7/2008 | Johnson et al. |
| 2008/0194603 A1 | 8/2008 | Li et al. |
| 2008/0194605 A1 | 8/2008 | Heinrich et al. |
| 2008/0207613 A1 | 8/2008 | Styles et al. |
| 2008/0214501 A1 | 9/2008 | Pan et al. |
| 2008/0260754 A1 | 10/2008 | Li et al. |
| 2008/0279867 A1 | 11/2008 | Atuegbu et al. |
| 2008/0300268 A1 | 12/2008 | Singh et al. |
| 2008/0312438 A1 | 12/2008 | Singh et al. |
| 2009/0131436 A1 | 5/2009 | Imbach et al. |
| 2009/0137588 A1 | 5/2009 | Singh et al. |
| 2009/0156622 A1 | 6/2009 | Singh et al. |
| 2009/0171086 A1 | 7/2009 | Singh et al. |
| 2009/0181987 A1 | 7/2009 | Honigberg et al. |
| 2009/0215803 A1 | 8/2009 | Rice et al. |
| 2009/0286778 A1 | 11/2009 | Combs et al. |
| 2009/0298830 A1 | 12/2009 | Mann et al. |
| 2009/0318407 A1 | 12/2009 | Bauer et al. |
| 2010/0004270 A1 | 1/2010 | Honigberg et al. |
| 2010/0016296 A1 | 1/2010 | Singh et al. |
| 2010/0022561 A1 | 1/2010 | Honigberg et al. |
| 2010/0029610 A1 | 2/2010 | Singh et al. |
| 2010/0041677 A1 | 2/2010 | Honigberg et al. |
| 2010/0081679 A1 | 4/2010 | Greul et al. |
| 2010/0088912 A1 | 4/2010 | Higgs et al. |
| 2010/0173285 A1 | 7/2010 | Varmus et al. |
| 2010/0197918 A1 | 8/2010 | Singh et al. |
| 2010/0249092 A1 | 9/2010 | Singh et al. |
| 2010/0254905 A1 | 10/2010 | Honigberg et al. |
| 2011/0039868 A1 | 2/2011 | Honigberg et al. |
| 2011/0105472 A1 | 5/2011 | Greul et al. |
| 2011/0207736 A1 | 8/2011 | Gray et al. |
| 2011/0224235 A1 | 9/2011 | Honigberg et al. |
| 2011/0245156 A1 | 10/2011 | Sielecki-Dzurdz |
| 2011/0245284 A1 | 10/2011 | Greul et al. |
| 2011/0281322 A1 | 11/2011 | Honigberg et al. |
| 2012/0040968 A1 | 2/2012 | Shimada et al. |
| 2012/0065201 A1 | 3/2012 | Honigberg et al. |
| 2012/0071497 A1 | 3/2012 | Buggy et al. |
| 2012/0077832 A1 | 3/2012 | Witowski et al. |
| 2012/0083006 A1 | 4/2012 | Ramsden et al. |
| 2012/0087915 A1 | 4/2012 | Buggy et al. |
| 2012/0088912 A1 | 4/2012 | Honigberg et al. |
| 2012/0094999 A1 | 4/2012 | Gray et al. |
| 2012/0101113 A1 | 4/2012 | Honigberg et al. |
| 2012/0101114 A1 | 4/2012 | Honigberg et al. |
| 2012/0149687 A1 | 6/2012 | Lee et al. |
| 2012/0149722 A1 | 6/2012 | Lee et al. |
| 2012/0157426 A1 | 6/2012 | Lee et al. |
| 2012/0165328 A1 | 6/2012 | Honigberg et al. |
| 2012/0165332 A1 | 6/2012 | Major et al. |
| 2012/0184013 A1 | 7/2012 | Honigberg et al. |
| 2012/0184567 A1 | 7/2012 | Honigberg et al. |
| 2012/0202264 A1 | 8/2012 | Honigberg et al. |
| 2012/0270237 A9 | 10/2012 | Ramsden et al. |
| 2012/0296089 A1 | 11/2012 | Honigberg et al. |
| 2012/0316135 A1 | 12/2012 | Dalgarno et al. |
| 2012/0329130 A1 | 12/2012 | Honigberg et al. |
| 2013/0065879 A1 | 3/2013 | Singh et al. |
| 2013/0065899 A1 | 3/2013 | Singh et al. |
| 2013/0072469 A1 | 3/2013 | Singh et al. |
| 2013/0137708 A1 | 5/2013 | Garske et al. |
| 2013/0165462 A1 | 6/2013 | Singh et al. |
| 2013/0267530 A1 | 10/2013 | Lai |
| 2014/0057929 A1 | 2/2014 | Witowski et al. |
| 2014/0134265 A1 | 5/2014 | Buggy et al. |
| 2014/0142123 A1 | 5/2014 | Honigberg et al. |
| 2014/0163046 A1 | 6/2014 | Honigberg et al. |
| 2014/0187564 A1 | 7/2014 | Honigberg et al. |
| 2014/0187565 A1 | 7/2014 | Honigberg et al. |
| 2014/0213574 A1 | 7/2014 | Singh et al. |
| 2016/0022677 A1 | 1/2016 | Lai |
| 2017/0217904 A1 | 8/2017 | Lai et al. |

FOREIGN PATENT DOCUMENTS

| | | |
|---|---|---|
| CN | 103159742 A | 6/2013 |
| EP | 1 054 004 A1 | 11/2000 |
| JP | H0741461 A | 2/1995 |
| WO | WO-96/28427 A1 | 9/1996 |
| WO | WO-97/19065 A1 | 5/1997 |
| WO | WO-99/31073 A1 | 6/1999 |
| WO | WO-00/027825 A1 | 5/2000 |
| WO | WO-00/046203 A2 | 8/2000 |
| WO | WO-00/078731 A1 | 12/2000 |
| WO | WO-01/047897 A1 | 7/2001 |
| WO | WO-01/060816 A1 | 8/2001 |
| WO | WO-01/064654 A1 | 9/2001 |
| WO | WO-01/064655 A1 | 9/2001 |
| WO | WO-01/085699 A2 | 11/2001 |
| WO | WO-02/083653 A1 | 10/2002 |
| WO | WO-03/016306 A1 | 2/2003 |
| WO | WO-03/030909 A1 | 4/2003 |
| WO | WO-03/063794 A2 | 8/2003 |
| WO | WO-03/066601 A1 | 8/2003 |
| WO | WO-2004/014382 A1 | 2/2004 |
| WO | WO-2004/031232 A1 | 4/2004 |
| WO | WO-2004/056786 A2 | 7/2004 |
| WO | WO-2004/069812 A1 | 8/2004 |
| WO | WO-2004/074244 A2 | 9/2004 |
| WO | WO-2004/080980 A1 | 9/2004 |
| WO | WO-2004/096224 A1 | 11/2004 |
| WO | WO-2005/013996 A2 | 2/2005 |
| WO | WO-2005/016893 A2 | 2/2005 |
| WO | WO-2005/016894 A1 | 2/2005 |
| WO | WO-2005/026130 A2 | 3/2005 |
| WO | WO-2005/026158 A1 | 3/2005 |

(56) References Cited

FOREIGN PATENT DOCUMENTS

| | | |
|---|---|---|
| WO | WO-2005/063722 A1 | 7/2005 |
| WO | WO-2005/070890 A2 | 8/2005 |
| WO | WO-2006/021544 A1 | 3/2006 |
| WO | WO-2006/045066 A2 | 4/2006 |
| WO | WO-2006/053109 A1 | 5/2006 |
| WO | WO-2006/055561 A2 | 5/2006 |
| WO | WO-2006/068770 A1 | 6/2006 |
| WO | WO-2006/074057 A2 | 7/2006 |
| WO | WO-2006/078846 A1 | 7/2006 |
| WO | WO-2006/101977 A2 | 9/2006 |
| WO | WO-2006/108487 A1 | 10/2006 |
| WO | WO-2006/124874 A2 | 11/2006 |
| WO | WO-2006/128129 A2 | 11/2006 |
| WO | WO-2006/129100 A1 | 12/2006 |
| WO | WO-2006/133426 A2 | 12/2006 |
| WO | WO-2007/027238 A2 | 3/2007 |
| WO | WO-2007/048064 A2 | 4/2007 |
| WO | WO-2007/053452 A1 | 5/2007 |
| WO | WO-2007/056151 A2 | 5/2007 |
| WO | WO-2007/085833 A2 | 8/2007 |
| WO | WO-2007/089768 A2 | 8/2007 |
| WO | WO-2007/113254 A1 | 10/2007 |
| WO | WO-2007/113256 A1 | 10/2007 |
| WO | WO-2007/120339 A1 | 10/2007 |
| WO | WO-2007/120980 A2 | 10/2007 |
| WO | WO-2007/125351 A1 | 11/2007 |
| WO | WO-2008/005538 A2 | 1/2008 |
| WO | WO-2008/009458 A1 | 1/2008 |
| WO | WO-2008/025556 A1 | 3/2008 |
| WO | WO-2008/049123 A2 | 4/2008 |
| WO | WO-2008/064274 A1 | 5/2008 |
| WO | WO-2008/073687 A2 | 6/2008 |
| WO | WO-2008/074515 A1 | 6/2008 |
| WO | WO-2008/079719 A1 | 7/2008 |
| WO | WO-2008/079907 A1 | 7/2008 |
| WO | WO-2008/080841 A1 | 7/2008 |
| WO | WO-2008/080965 A2 | 7/2008 |
| WO | WO-2008/088303 A1 | 7/2008 |
| WO | WO-2008/092199 A1 | 8/2008 |
| WO | WO-2008/107096 A1 | 9/2008 |
| WO | WO-2008/115738 A1 | 9/2008 |
| WO | WO-2008/115742 A1 | 9/2008 |
| WO | WO-2008/118822 A1 | 10/2008 |
| WO | WO-2008/118823 A2 | 10/2008 |
| WO | WO-2009/012421 A1 | 1/2009 |
| WO | WO-2009/017838 A2 | 2/2009 |
| WO | WO-2009/029682 A1 | 3/2009 |
| WO | WO-2009/032668 A2 | 3/2009 |
| WO | WO-2009/032694 A1 | 3/2009 |
| WO | WO-2009/032703 A1 | 3/2009 |
| WO | WO-2009/080638 A2 | 7/2009 |
| WO | WO-2009/105675 A1 | 8/2009 |
| WO | WO-2009/112490 A1 | 9/2009 |
| WO | WO-2009/115267 A2 | 9/2009 |
| WO | WO-2009/127642 A2 | 10/2009 |
| WO | WO-2009/132202 A2 | 10/2009 |
| WO | WO-2009/143389 A1 | 11/2009 |
| WO | WO-2009/158571 A1 | 12/2009 |
| WO | WO-2010/025833 A1 | 3/2010 |
| WO | WO-2010/081679 A2 | 7/2010 |
| WO | WO-2010/129053 A2 | 11/2010 |
| WO | WO-2011/079231 A1 | 6/2011 |
| WO | WO-2011/090760 A1 | 7/2011 |
| WO | WO-2011/140338 A1 | 11/2011 |
| WO | WO-2011/153514 A2 | 12/2011 |
| WO | WO-2012/021444 A1 | 2/2012 |
| WO | WO-2012/061299 A1 | 5/2012 |
| WO | WO-2012/061303 A1 | 5/2012 |
| WO | WO-2012/061415 A1 | 5/2012 |
| WO | WO-2012/064706 A1 | 5/2012 |
| WO | WO-2012/158843 A2 | 11/2012 |
| WO | WO-2013/138495 A1 | 9/2013 |
| WO | WO-2013/138502 A1 | 9/2013 |

OTHER PUBLICATIONS

Calvo, E. et al., Administration of Cl-1033, an Irreversible Pan-erbB Tyrosine Kinase Inhibitor, Is Feasible on a 7-Day Off Schedule: A Phase I Pharmacokinetic and Food Effect Study, Clinical Cancer Research, 10: 7112-7120 (2004).

Carter, T. et al, Inhibition of drug-resistant mutants of ABL, KIT, and EGF receptor kinases, Proc. Natl. Acad. Sci. USA 102(31):11011-11016 (2005).

Clovis Oncology, Press Release, "Clovis Oncology's CO-1686 Demonstrates Compelling Clinical Activity and Progression-free Survival (PFS) in Updated Phase 1/2 Study Results in Patients with EGFR-Mutant Non-small Cell Lung Cancer (NSCLC)", May 31, 2014.

Cohen, M. et al., Structural bioinformatics-based design of selective, irreversible inhibitors, Science 308:1318-1321 (2005).

Curto, M. et al., Contact-dependent inhibition of EGFR signaling by Nf2/Merlin, J Cell Biol 177:893-903 (2007).

Ding, K. et al., Design, Synthesis and Biological Evaluation of Novel Conformationally Constrained Inhibitors Targeting Epidermal Growth Factor Receptor T790M mutant, J. Med. Chem., Just Accepted Manuscript, 1-36 (2012).

Extended European Search Report for EP11816874.9, 5 pages (dated Dec. 12, 2014).

Extended European Search Report for EP11838624.2, 5 pages (dated Jun. 6, 2014).

Extended European Search Report for EP11838628.3, 7 pages (dated Jun. 20, 2014).

Extended European Search Report for EP11839800.7, 8 pages (dated Jun. 24, 2014).

Extended European Search Report for EP13760923.6, 5 pages (dated Jul. 27, 2015).

Fabian, M. et al., A small molecule-kinase interaction map for clinical kinase inhibitors, Nature Biotechnology, 23(3): 329 (2005).

Fallon, K. et al., Constitutive activation of the neuregulin-1/erbB signaling pathway promotes the proliferation of a human peripheral neuroepithelioma cell line, J Neuro Oncol 66:273-84 (2004).

Frank, D., STAT signaling in the pathogenesis and treatment of cancer, Mol. Med. 5 :432-456 (1999).

Fry, D. et al., Specific, irreversible inactivation of the epidermal growth factor receptor and erbB2, by a new class of tyrosine kinase inhibitor, Proc. Natl. Acad. Sci. USA 95:12022-12027 (1998).

Ghoneim, K., Synthesis and evaluation of some 2-, 4-, di- substituted -6-methylpyrimidine derivatives for antimicrobial activity, J. Indian Chem. Soc. 63(10):914-917 (1986).

Ghosh, D., 2-4-bis (arylamino)-5-methylpyrimidines as antimicrobial agents, J. Med. Chem. 10(5):974 (1967).

Ghosh, D., 2-4-bis (arylamino)-6-methylpyrimidines as antimicrobial agents, J. Indian Chem. Soc. 58(5):512-573 (1981).

Gonzales, A. et al, Antitumor activity and pharmacokinetic properties of PF-00299804, a second-generation, irreversible pan-erbB receptor tyrosine kinase inhibitor, Mol. Cancer Ther. 7(7):1880-1889 (2008).

Gould, Philip L., Salt selection for basic drugs, International Journal of Pharmaceutics, 33:201-217 (1986).

Hur, W. et al., Clinical stage EGFR inhibitors irreversibly alkylate Bmx kinase, Bioorg. Med. Chem. Lett. 18:5916-5919 (2008).

International Search Report for PCT/US09/48784, 8 pages (dated Nov. 16, 2009).

International Search Report for PCT/US10/31714, 4 pages (dated Aug. 13, 2010).

International Search Report for PCT/US10/62432, 4 pages (dated May 26, 2011).

International Search Report for PCT/US11/58610, 4 pages (dated Mar. 27, 2012).

International Search Report for PCT/US11/58616, 3 pages (dated Mar. 27, 2012).

International Search Report for PCT/US11/59726, 3 pages (dated Mar. 20, 2012).

International Search Report of PCT/US11/46926, Publication No. WO 2012/021444 (dated Dec. 22, 2011).

(56) References Cited

OTHER PUBLICATIONS

International Search Report of PCT/US13/30982, 2 pages (dated May 30, 2013).
International Search Report of PCT/US13/30996, 2 pages (dated May 30, 2013).
Kirken, R., Targeting Jak3 for immune suppression and allograft acceptance, Transplant. Proc. 33 :3268-3270 (2001).
Kumar, A., et al, Structure and Clinical Relevance of the Epidermal Growth Factor Receptor in Human Cancer, Journal of Clinical Oncology 26(10):1742-1751 (2008).
Kwak, E. et al., Irreversible inhibitors of the EGF receptor may circumvent acquired resistance to gefitinib, Proc. Natl. Acad. Sci. USA 102:7665-7670 (2005).
Lajeunesse, D. et al., A systematic screen for dominant second-site modifiers of Merlin/NF2 phenotypes reveals an interaction with blistered/DSRF and scribbler, Genetics 158:667-79 (2001).
Li, D. et al., BIBW2992, an irreversible EGFR/HER2 inhibitor highly effective in preclinical lung cancer models, Oncogene 27:4702-4711 (2008).
Lin, N. and Winer, E., New targets for therapy in breast cancer: Small molecule tyrosine kinase inhibitors, Breast Cancer Res 6:204-210 (2004).
Liu, Rong, Ed., Water-Insoluble Drug Formulation, Chapter 15, CRC Press, 417-435 (2008).
Malaviya, R. et al., Targeting Janus Kinase 3 in Mast Cells Prevents Immediate Hypersensitivity Reactions and Anaphylaxis, J. Biol. Chem. 274 :27028-27038 (1999).
McClatchey, A. and Giovannini, M., Membrane organization and tumorigenesis—the NF2 tumor suppressor, Merlin, Genes Dev 19:2265-77 (2005).
Minkovsky, N. and Berezov, A., BIBW-2992, a dual receptor tyrosine kinase inhibitor for the treatment of solid tumors, Curr Opin Invest Drugs 9:1336-1346 (2008).
Morissette, S.L. et al., High-throughput crystallization: polymorphs, salts, co-crystals and solvates of pharmaceutical solids, Advanced Drug Delivery Reviews, 56: 275-300 (2004).
Morris, K.R. et al., An integrated approach to the selection of optimal salt form for a new drug candidate, International Journal of Pharmaceutics, 105: 209-217 (1994).
Ogiso, et al., Crystal Structure of the Complex of Human Epidermal Growth Factor and Receptor Extracellular Domains, Cell, vol. 110, 775-787 (2002).
Pelton, P. et al., Ruffling membrane, stress fiber, cell spreading and proliferation abnormalities in human Schwann cells, Oncogene 17:2195-2209 (1998).
PubChem CID 44594695. Feb. 1, 2010. [Retrieved from the Internet May 15, 2011: http://pubchem.ncbi.nlm.nih.gov/summary.cgi?cid=44594695&loc=ec_rcs].
Readinger, J. et al., Selective Targeting of ITK Blocks Multiple Steps of HIV Replication, Proc. Natl. Acad. Sci. USA 105: 6684-6689 (2008).
Seidel, H. et al., Pharmaceutical intervention in the JAK/STAT signaling pathway, Oncogene 19: 2645-2656 (2000).
Sequist, L., Second-Generation Epidermal Growth Factor Receptor Tyrosine Kinase Inhibitors in Non-Small Cell Lung Cancer, The Oncologist 12(3):325-330 (2007).
Serajuddin, A.T.M., Salt formation to improve drug solubility, Advanced Drug Delivery Reviews, 59:603-616 (2007).

Singh, J. et al, Structure-based design of a potent, selective, and irreversible inhibitor of the catalytic domain of the erbB receptor subfamily of protein tyrosine kinases, J. Med. Chem. 40:1130-1135 (1997).
Soria, J-C. et al., "Abstract # 1354: First-In-Human Evaluation of CO-1686, an Irreversible, Highly Selective Tyrosine Kinase Inhibitor of Mutations of EGFR (Activating and T790M)," 15th World Conference on Lung Cancer, Oct. 27, 2013.
Stahl, H.P. and Wermuth, C.G., Handbook of Pharmaceutical Salts. Properties, Selection, and Use. Wiley-VCH, 265-327 (2008).
Stonecypher, M. et al., Activation of the neuregulin-1/ErbB signaling pathway promotes the proliferation of neoplastic Schwann cells in human malignant peripheral nerve sheath tumors, Oncogene 24:5589-5605 (2005).
Sudbeck, E. et al., Structure-based Design of Specific Inhibitors of Janus Kinase 3 as Apoptosis-inducing Antileukemic Agents, Clin. Cancer Res. 5: 1569-1582 (1999).
Supplementary European Search Report for EP10844293.0, 8 pages (Jun. 27, 2013).
Swarbrick, James and Boylan, James C., Eds., Encyclopedia of Pharmaceutical Technology 13, Marcel Dekker, NY, 453-499 (1996).
Trieu, V. et al., A specific inhibitor of janus kinase-3 increases survival in a transgenic mouse model of amyotrophic lateral sclerosis, Biochem. Biophys. Res. Commun. 267 :22-25 (2000).
Walter, A. O. et al., "Discovery of a mutant-selective covalent inhibitor of EGFR that overcomes T790M-mediated resistance in NSCLC," *Cancer Discov*. Dec. 2013; 3(12): 1404-1415.
Wong, K. et al, a phase I study with neratinib (HKI-272), an irreversible pan Erb B receptor tyrosine kinase inhibitor, in patients with solid tumors, Clin. Cancer Res. 15(7):2552-2558 (2009).
Written Opinion for PCT/US09/48784, 9 pages (dated Nov. 16, 2009).
Written Opinion for PCT/US10/31714, 7 pages (dated Aug. 13, 2010).
Written Opinion for PCT/US10/62432, 14 pages (dated May 26, 2011).
Written Opinion for PCT/US11/46926, 9 pages (dated Dec. 22, 2011).
Written Opinion for PCT/US11/58610, 8 pages (dated Mar. 27, 2012).
Written Opinion for PCT/US11/58616, 9 pages (dated Mar. 27, 2012).
Written Opinion for PCT/US11/59726, 7 pages (dated Mar. 20, 2012).
Written Opinion of PCT/US13/30982, 12 pages (dated May 30, 2013).
Written Opinion of PCT/US13/30996, 12 pages (dated May 30, 2013).
Zhang, J. et al., Targeting Cancer with Small Molecule Kinase Inhibitors, Nature Rev. Cancer 9:28-39 (2009).
Zhang, Y. et al., Antitumor Activity of Epidermal Growth Factor Receptor-Related Protein is Mediated by Inactivation of ErbB Receptors and Nuclear Factor-kB in Pancreatic Cancer, Cancer Res 66:1025-1032 (2006).
Zhou, W. et al. Novel mutant-selective EGFR kinase inhibitors against EGFR T790M, Nature, 462(7276): 1070-1074 (2009).
U.S. Appl. No. 15/869,635, Lee et al.
Extended European Search Report for EP13761487.1, 7 pages (Aug. 20, 2015).

\* cited by examiner

SOLID FORMS OF AN EPIDERMAL GROWTH FACTOR RECEPTOR KINASE INHIBITOR

CROSS REFERENCE TO RELATED CASES

The present application claims priority to U.S. provisional application Ser. No. 61/611,376, filed Mar. 15, 2012, the entirety of which is hereby incorporated by reference.

FIELD OF THE INVENTION

The present invention provides solid forms of a compound useful as mutant-selective inhibitors of epidermal growth factor receptor (EGFR) kinase. The invention also provides pharmaceutically acceptable compositions comprising solid forms of the present invention and methods of using the compositions in the treatment of various disorders.

Protein tyrosine kinases are a class of enzymes that catalyze the transfer of a phosphate group from ATP or GTP to a tyrosine residue located on a protein substrate. Receptor tyrosine kinases act to transmit signals from the outside of a cell to the inside by activating secondary messaging effectors via a phosphorylation event. A variety of cellular processes are promoted by these signals, including proliferation, carbohydrate utilization, protein synthesis, angiogenesis, cell growth, and cell survival.

There is strong precedent for involvement of the EGFR in human cancer because over 60% of all solid tumors overexpress at least one of these proteins or their ligands. Overexpression of EGFR is commonly found in breast, lung, head and neck, bladder tumors.

Activating mutations in the tyrosine kinase domain of EGFR have been identified in patients with non-small cell lung cancer (Lin, N. U.; Winer, E. P., Breast Cancer Res 6; 204-210, 2004). The reversible inhibitors Tarceva (erlotinib) and Iressa (gefitinib) currently are first-line therapy for non-small cell lung cancer patients with activating mutations. The most common activating mutations are L858R and delE746-A750.

Additionally, in the majority of patients that relapse, acquired drug resistance, such as by mutation of gatekeeper residue T790M, has been detected in at least half of such clinically resistant patients. Moreover, T790M may also be pre-existing; there may be an independent, oncogenic role for the T790M mutation. For example, there are patients with the L858R/T790M mutation who never received gefitinib treatment. In addition, germline EGFR T790M mutations are linked with certain familial lung cancers.

Current drugs in development, including second-generation covalent inhibitors, such as BIBW2992, HKI-272 and PF-0299804, are effective against the T790M resistance mutation but exhibit dose-limiting toxicities due to concurrent inhibition of WT EGFR. Accordingly, there remains a need to find mutant-selective EGFR kinase inhibitors useful as therapeutic agents.

SUMMARY OF THE INVENTION

It has now been found that the novel solid forms of the present invention, and compositions thereof, are useful as mutant-selective inhibitors of one or more EGFR kinases and exhibits desirable characteristics for the same. In general, these solid forms, and pharmaceutically acceptable compositions thereof, are useful for treating or lessening the severity of a variety of diseases or disorders as described in detail herein.

DETAILED DESCRIPTION OF THE INVENTION

Figure 1:
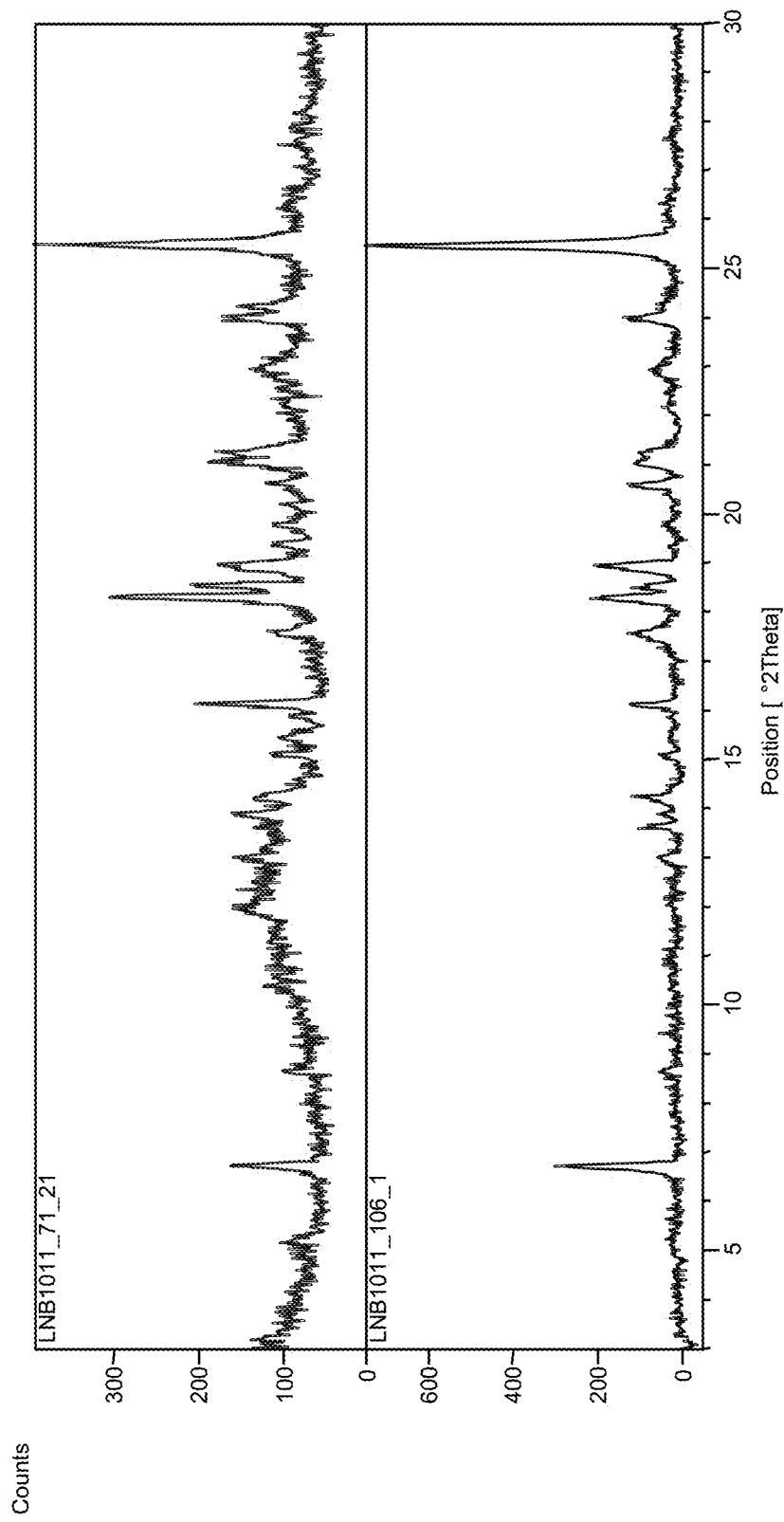
FIG. 1 depicts the x-ray powder diffraction (XRPD) pattern for Form A of Compound 1.

General Description of Certain Aspects of the Invention

U.S. application Ser. No. 13/286,061 ("the '061 application"), filed Oct. 31, 2011, the entirety of which is hereby incorporated herein by reference, describes certain 2,4-disubstituted pyrimidine compounds which covalently and irreversibly inhibit activity of EGFR kinase. Such compounds include Compound 1:

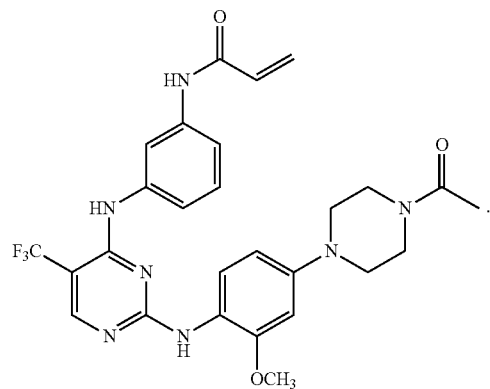

Compound 1 (N-(3-(2-(4-(4-acetylpiperazin-1-yl)-2-methoxyphenylamino)-5-(trifluoromethyl)pyrimidin-4-ylamino)phenyl)acrylamide)) is designated as compound number I-4 and the synthesis of Compound 1 is described in detail at Example 3 of the '061 application.

Compound 1 is active in a variety of assays and therapeutic models demonstrating selective covalent, irreversible inhibition of mutant EGFR kinase (in enzymatic and cellular assays). Notably, Compound 1 was found to inhibit human non-small cell lung cancer cell proliferation both in vitro and in vivo. Accordingly, Compound 1 is useful for treating one or more disorders associated with activity of mutant EGFR kinase.

It would be desirable to provide a solid form of Compound 1 that, as compared to Compound 1, imparts characteristics such as improved aqueous solubility, stability and ease of formulation. Accordingly, the present invention provides several solid forms of Compound 1.

According to one embodiment, the present invention provides an amorphous form, a crystalline form, or a mixture thereof. Exemplary solid forms are described in more detail below.

In other embodiments, the present invention provides Compound 1 substantially free of impurities. As used herein, the term "substantially free of impurities" means that the compound contains no significant amount of extraneous matter. Such extraneous matter may include starting materials, residual solvents, or any other impurities that may result from the preparation of, and/or isolation of, Compound 1. In certain embodiments, at least about 90% by weight of Compound 1 is present. In certain embodiments, at least about 95% by weight of Compound 1 is present. In still other embodiments of the invention, at least about 99% by weight of Compound 1 is present.

According to one embodiment, Compound 1 is present in an amount of at least about 95, 97, 97.5, 98.0, 98.5, 99, 99.5, 99.8 weight percent where the percentages are based on the total weight of the composition. According to another embodiment, Compound 1 contains no more than about 5.0 area percent HPLC of total organic impurities and, in certain embodiments, no more than about 3.0 area percent HPLC of total organic impurities and, in certain embodiments, no more than about 1.5 area percent HPLC total organic impurities relative to the total area of the HPLC chromatogram. In other embodiments, Compound 1 contains no more than about 1.0 area percent HPLC of any single impurity; no more than about 0.6 area percent HPLC of any single impurity, and, in certain embodiments, no more than about 0.5 area percent HPLC of any single impurity, relative to the total area of the HPLC chromatogram.

The structure depicted for Compound 1 is also meant to include all tautomeric forms of Compound 1. Additionally, structures depicted here are also meant to include compounds that differ only in the presence of one or more isotopically enriched atoms. For example, compounds having the present structure except for the replacement of hydrogen by deuterium or tritium, or the replacement of a carbon by a $^{13}$C- or $^{14}$C-enriched carbon are within the scope of this invention.

Solid Forms of Compound 1:

It has been found that Compound 1 can exist in a variety of solid forms. Such forms include polymorphs and amorphous forms. The solid forms can be solvates, hydrates and unsolvated forms of Compound 1. All such forms are contemplated by the present invention. In certain embodiments, the present invention provides Compound 1 as a mixture of one or more solid forms of Compound 1.

As used herein, the term "polymorph" refers to the different crystal structures (of solvated or unsolvated forms) in which a compound can crystallize.

As used herein, the term "solvate" refers to a solid form with either a stoichiometric or non-stoichiometric amount of solvent (e.g., a channel solvate). For polymorphs, the solvent is incorporated into the crystal structure. Similarly, the term "hydrate" refers to a solid form with either a stoichiometric or non-stoichiometric amount of water. For polymorphs, the water is incorporated into the crystal structure.

As used herein, the term "about", when used in reference to a degree 2-theta value refers to the stated value ±0.3 degree 2-theta. In certain embodiments, "about" refers to ±0.2 degree 2-theta or ±0.1 degree 2-theta.

In certain embodiments, Compound 1 is a crystalline solid. In other embodiments, Compound 1 is a crystalline solid substantially free of amorphous Compound 1. As used herein, the term "substantially free of amorphous Compound 1" means that the compound contains no significant amount of amorphous Compound 1. In certain embodiments, at least about 90% by weight of crystalline Compound 1 is present, or at least about 95% by weight of crystalline Compound 1 is present. In still other embodiments of the invention, at least about 97%, 98% or 99% by weight of crystalline compound 1 is present.

In certain embodiments, Compound 1 is a neat or unsolvated crystal form and thus does not have any water or solvent incorporated into the crystal structure. It has been found that Compound 1 can exist in at least two distinct neat (i.e., anhydrous) crystal forms, or polymorphs. In some embodiments, the present invention provides an anhydrous polymorphic form of Compound 1 referred to herein as Form A. In other embodiments, the present invention provides an anhydrous polymorphic form of Compound 1 referred to herein as Form B.

In certain embodiments, the present invention provides Form A of Compound 1. According to one embodiment, Form A of Compound 1 is characterized by one or more peaks in its powder X-ray diffraction pattern selected from those at about 6.73, about 18.30, about 18.96 and about 25.48 degrees 2-theta. In some embodiments, Form A of Compound 1 is characterized by two or more peaks in its powder X-ray diffraction pattern selected from those at about 6.73, about 18.30, about 18.96 and about 25.48 degrees 2-theta. In certain embodiments, Form A of Compound 1 is characterized by three or more peaks in its powder X-ray diffraction pattern selected from those at about 6.73, about 18.20, about 18.96 and about 25.48 degrees 2-theta. In particular embodiments, Form A of Compound 1 is characterized by substantially all of the peaks in its X-ray powder diffraction pattern selected from those at about 6.73, 14.24, 16.13, 18.30, 18.96, 20.59, 21.02, 21.23, 23.99 and 25.48 degrees 2-theta. In an exemplary embodiment, Form A of Compound 1 is characterized by substantially all of the peaks in its X-ray powder diffraction pattern selected from those at about

| °2-Theta |
|---|
| 5.21 |
| 5.42 |
| 6.73 |
| 8.67 |
| 9.47 |
| 10.59 |
| 10.93 |
| 12.07 |
| 13.00 |
| 13.06 |
| 13.64 |
| 13.89 |
| 14.24 |
| 15.08 |
| 15.47 |
| 15.88 |
| 16.13 |
| 17.57 |
| 18.30 |
| 18.51 |
| 18.96 |
| 19.80 |
| 20.43 |
| 20.59 |
| 21.02 |
| 21.23 |
| 22.18 |
| 22.93 |
| 23.99 |
| 24.22 |
| 25.48 |
| 26.18 |
| 26.50 |
| 27.68 |
| 30.32 |

| °2-Theta |
|---|
| 30.65 |
| 31.41 |
| 32.31 |
| 33.62 |
| 34.01 |
| 37.93 |
| 38.66 |
| 39.78 |
| 45.41 |

Figure 2:
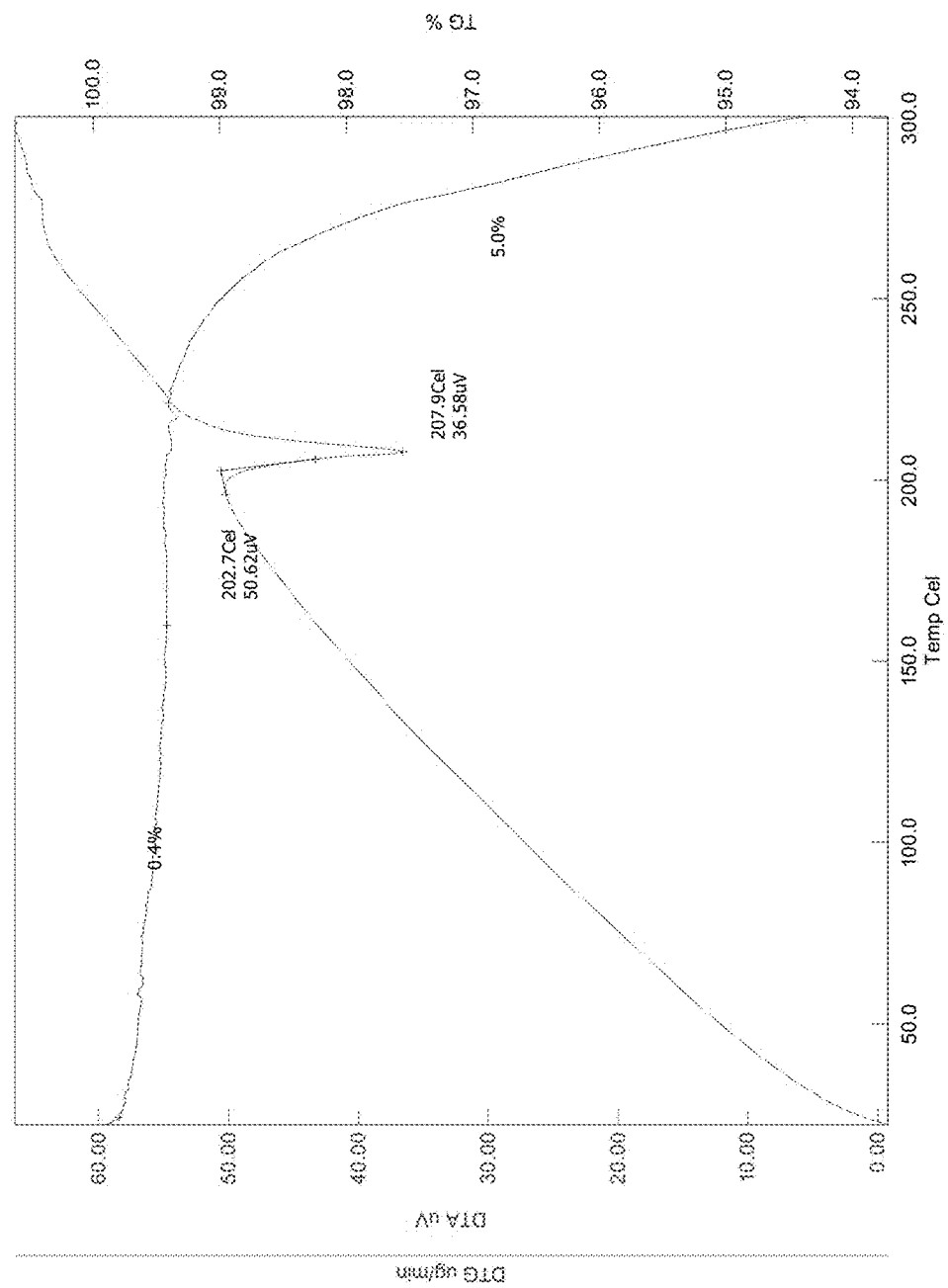
FIG. 2 depicts the thermogravimetric analysis/differential thermal analyser (TGA/DTA) pattern for Form A of Compound 1.
Figure 3:
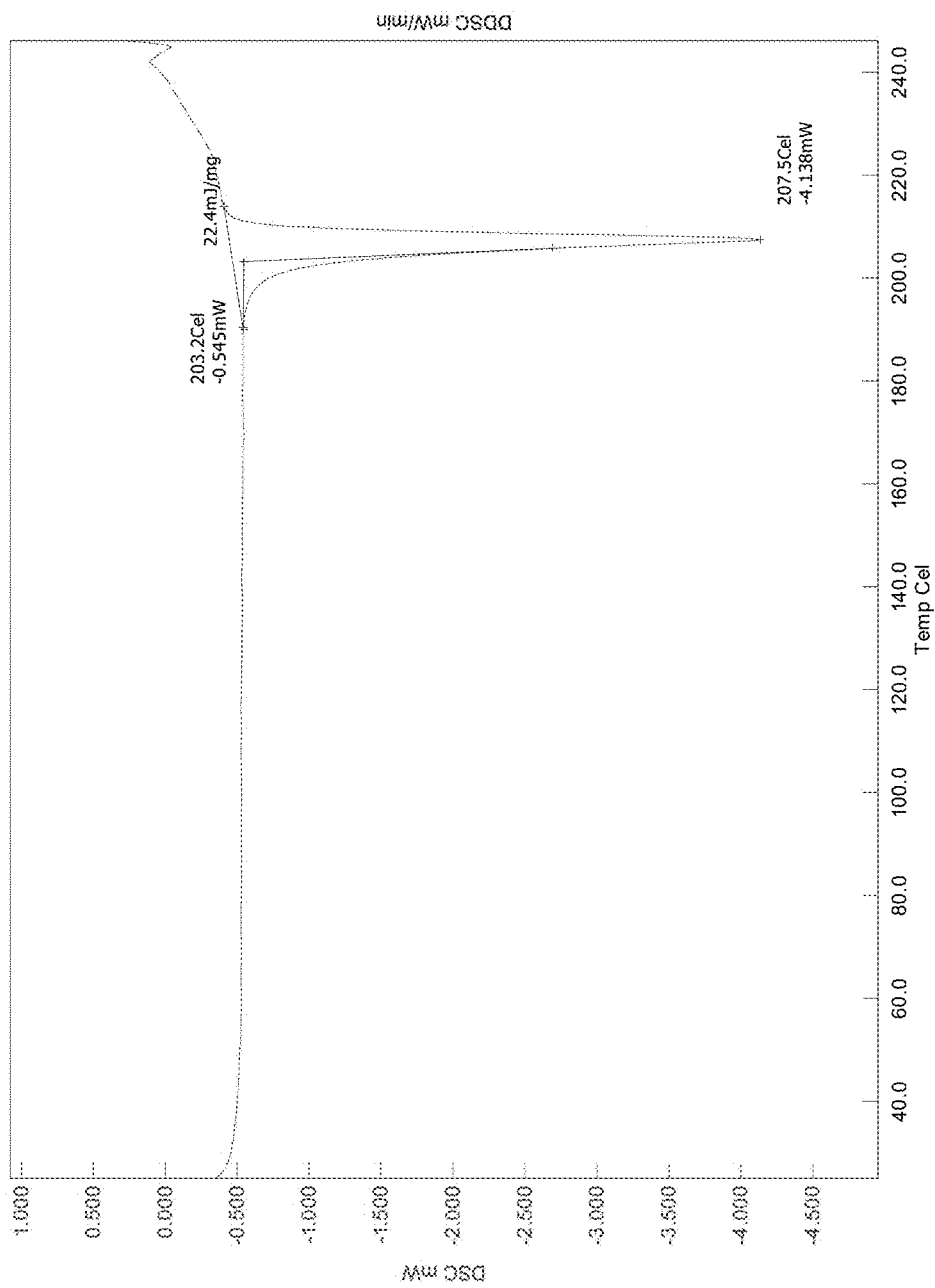
FIG. 3 depicts the differential scanning calorimetry (DSC) pattern for Form A of Compound 1.
Figure 4:
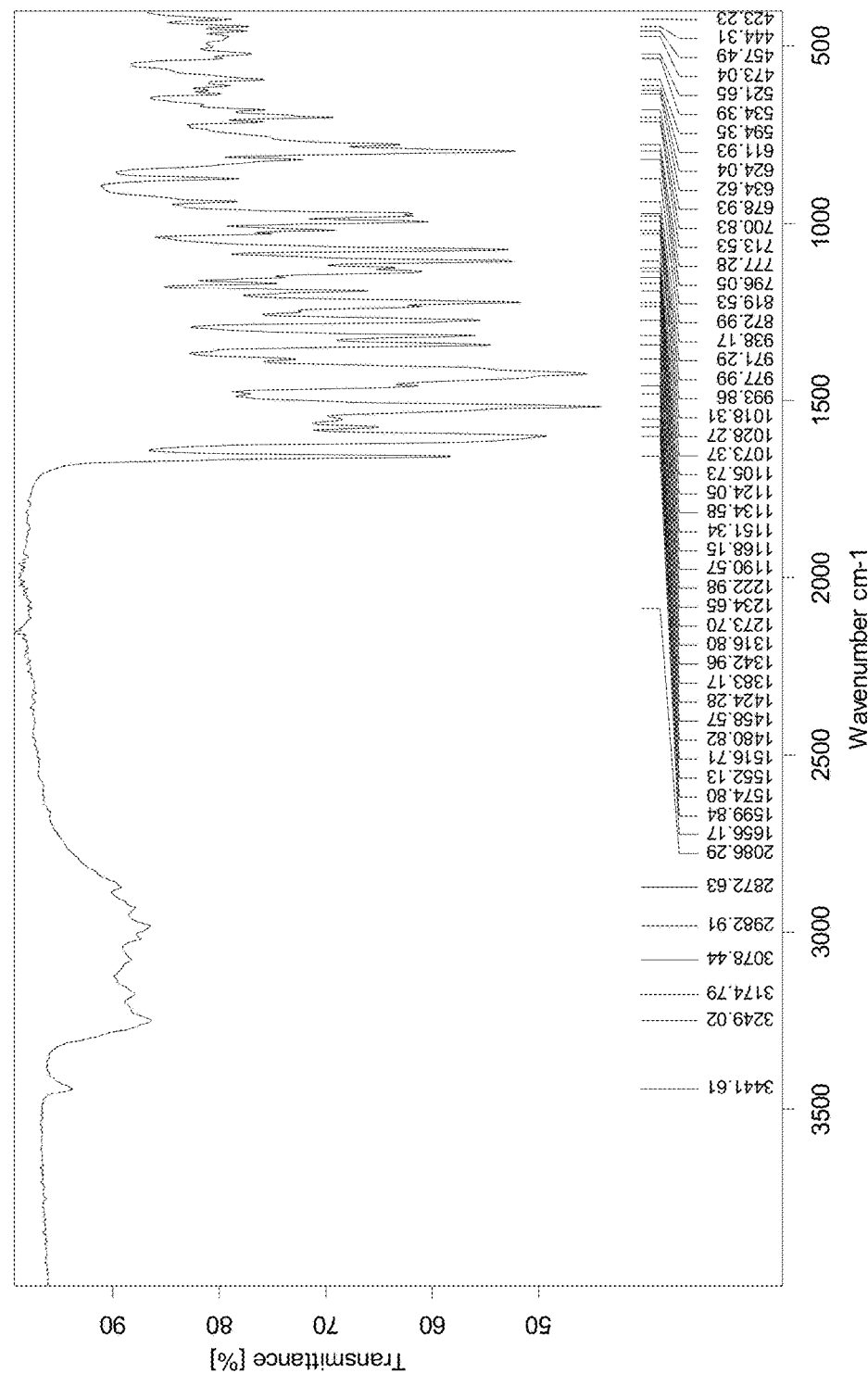
FIG. 4 depicts the infrared (IR) spectrum for Form A of Compound 1.
Figure 5:
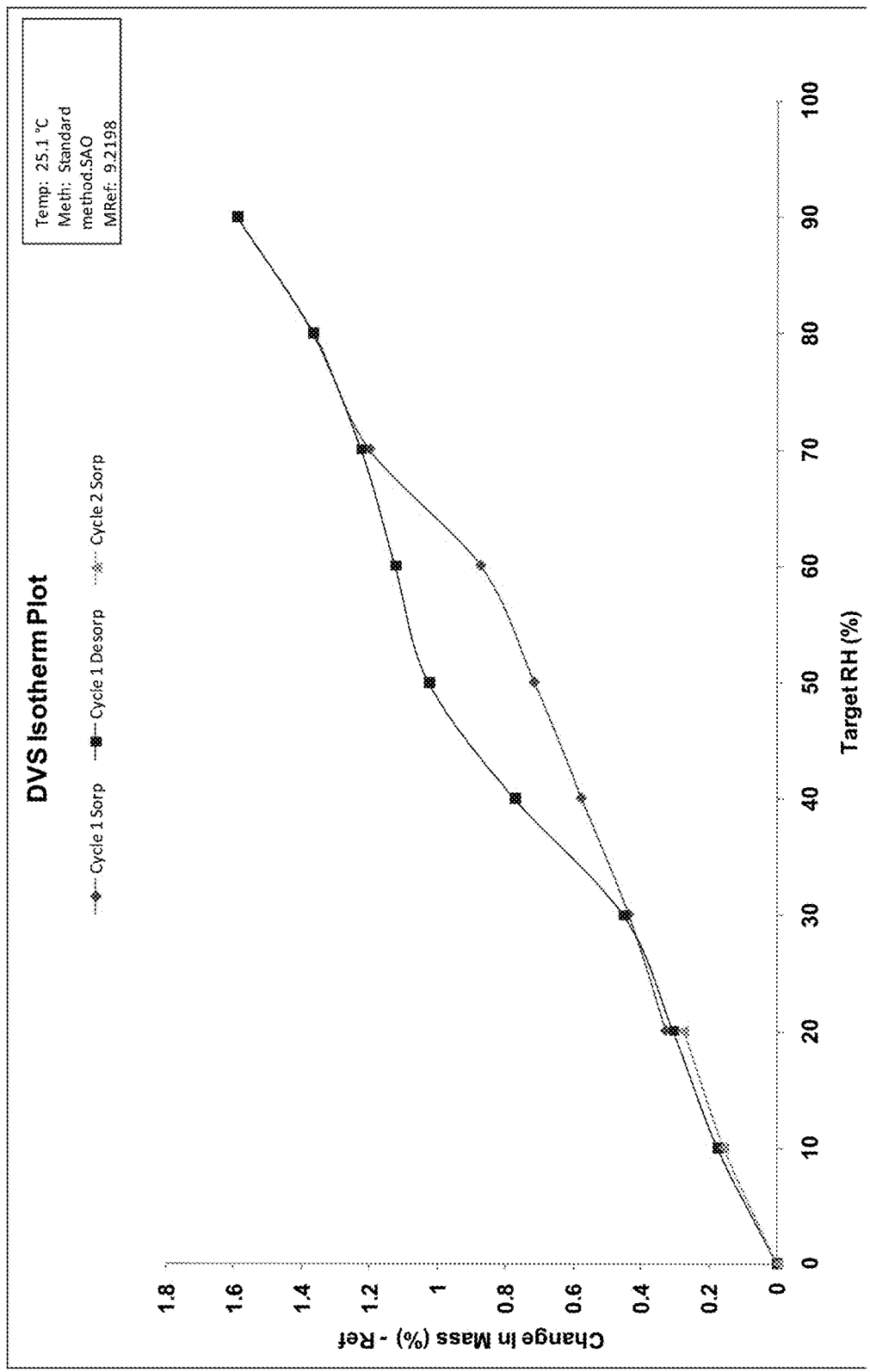
FIG. 5 depicts the dynamic vapour sorption (DVS) pattern for Form A of Compound 1.

According to one aspect, Form A of Compound 1 has a powder X-ray diffraction pattern substantially similar to that depicted in FIG. 1. According to another aspect, Form A of Compound 1 has a thermogravimetric analysis pattern substantially similar to that depicted in FIG. 2. Accordingly to yet another aspect, Form A of Compound 1 has a differential scanning calorimetry pattern substantially similar to that depicted in FIG. 3. According to a further embodiment, Form A of Compound 1 has a infrared spectrum substantially similar to that depicted in FIG. 4. According to another embodiment, Form A of Compound 1 has a dynamic vapour sorption pattern substantially similar to that depicted in FIG. 5. Form A of Compound 1 can be characterized by substantial similarity to two or more of these figures simultaneously.

In certain embodiments, the present invention provides Form B of Compound 1. According to another embodiment, Form B of Compound 1 is characterized by one or more peaks in its powder X-ray diffraction pattern selected from those at about 10.67, about 12.21, about 18.11, about 19.24 and about 21.53 degrees 2-theta. In some embodiments, Form B of Compound 1 is characterized by two or more peaks in its powder X-ray diffraction pattern selected from those at about 10.67, about 12.21, about 18.11, about 19.24 and about 21.53 degrees 2-theta. In certain embodiments, Form B of Compound 1 is characterized by three or more peaks in its powder X-ray diffraction pattern selected from those at about 10.67, about 12.21, about 18.11, about 19.24 and about 21.53 degrees 2-theta. In particular embodiments, Form B of Compound 1 is characterized by substantially all of the peaks in its X-ray powder diffraction pattern selected from those at about 8.96, 10.67, 12.21, 14.56, 16.49, 17.74, 18.11, 19.24, 19.90, 21.53 and 23.93 degrees 2-theta. In an exemplary embodiment, Form B of Compound 1 is characterized by substantially all of the peaks in its X-ray powder diffraction pattern selected from those at about:

| °2-Theta |
|---|
| 3.03 |
| 4.74 |
| 5.01 |
| 6.91 |
| 7.59 |
| 8.23 |
| 8.96 |
| 10.67 |
| 12.21 |
| 13.31 |
| 14.28 |
| 14.56 |
| 15.29 |
| 15.59 |
| 16.49 |
| 16.98 |
| 17.42 |
| 17.74 |

| °2-Theta |
|---|
| 18.11 |
| 19.24 |
| 19.90 |
| 21.53 |
| 22.25 |
| 23.93 |
| 24.63 |
| 24.87 |
| 25.30 |
| 26.34 |
| 27.66 |
| 29.31 |
| 30.57 |
| 31.21 |
| 32.39 |
| 32.58 |
| 33.41 |
| 34.38 |
| 36.19 |
| 39.13 |
| 40.01 |
| 41.81 |
| 45.49 |
| 48.16 |

Figure 6:
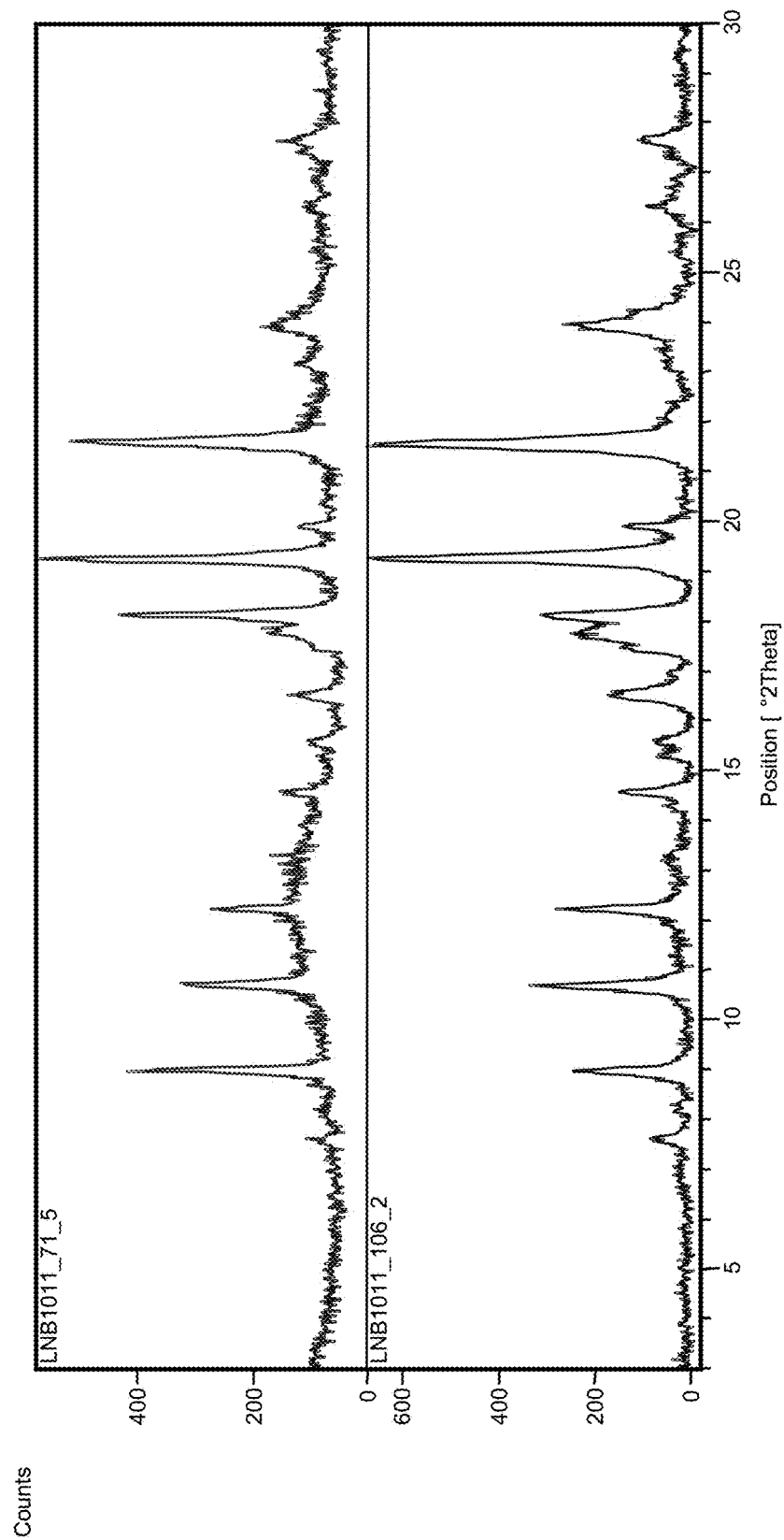
FIG. 6 depicts the XRPD pattern for Form B of Compound 1.
Figure 7:
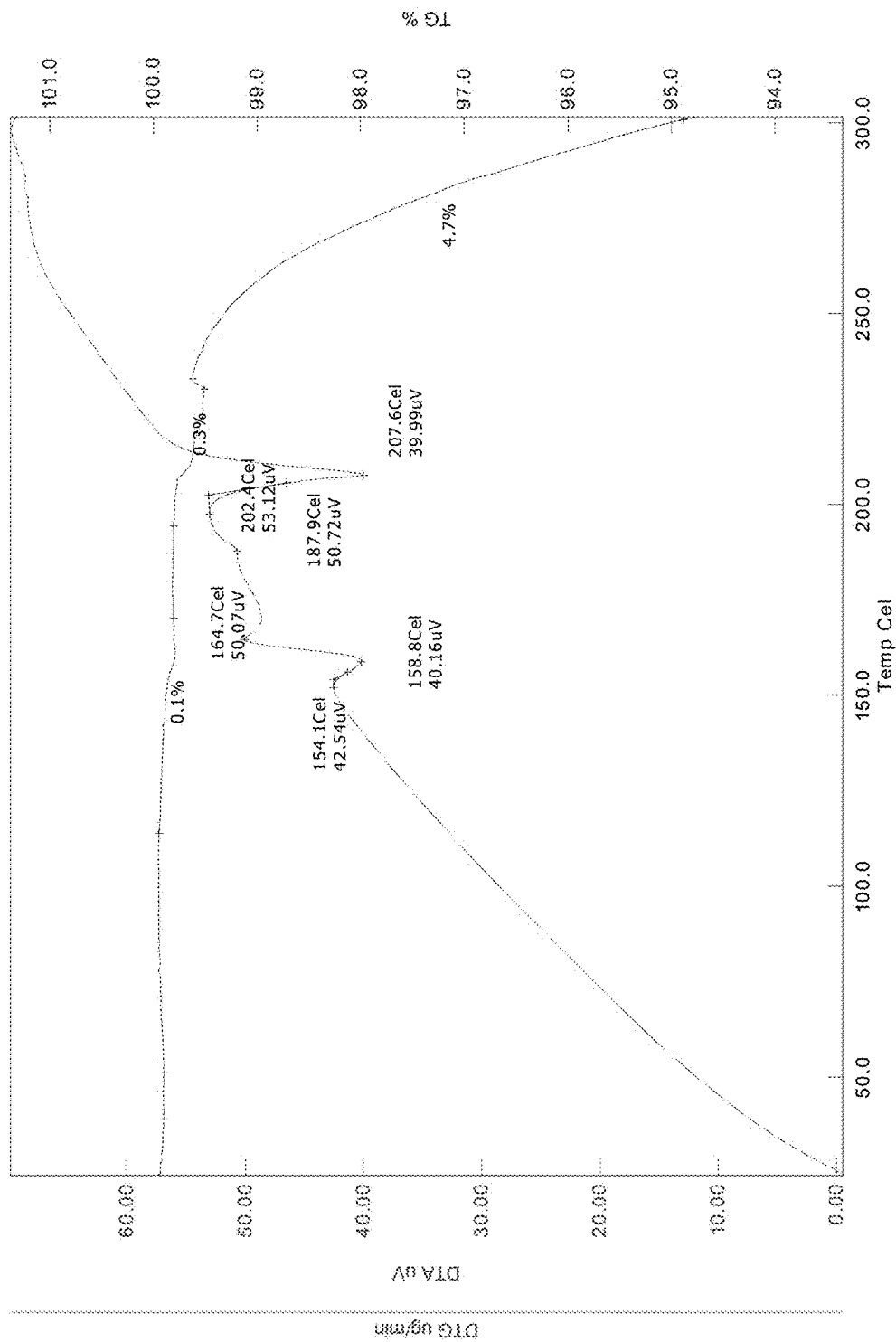
FIG. 7 depicts the TGA/DTA pattern for Form B of Compound 1.
Figure 8:
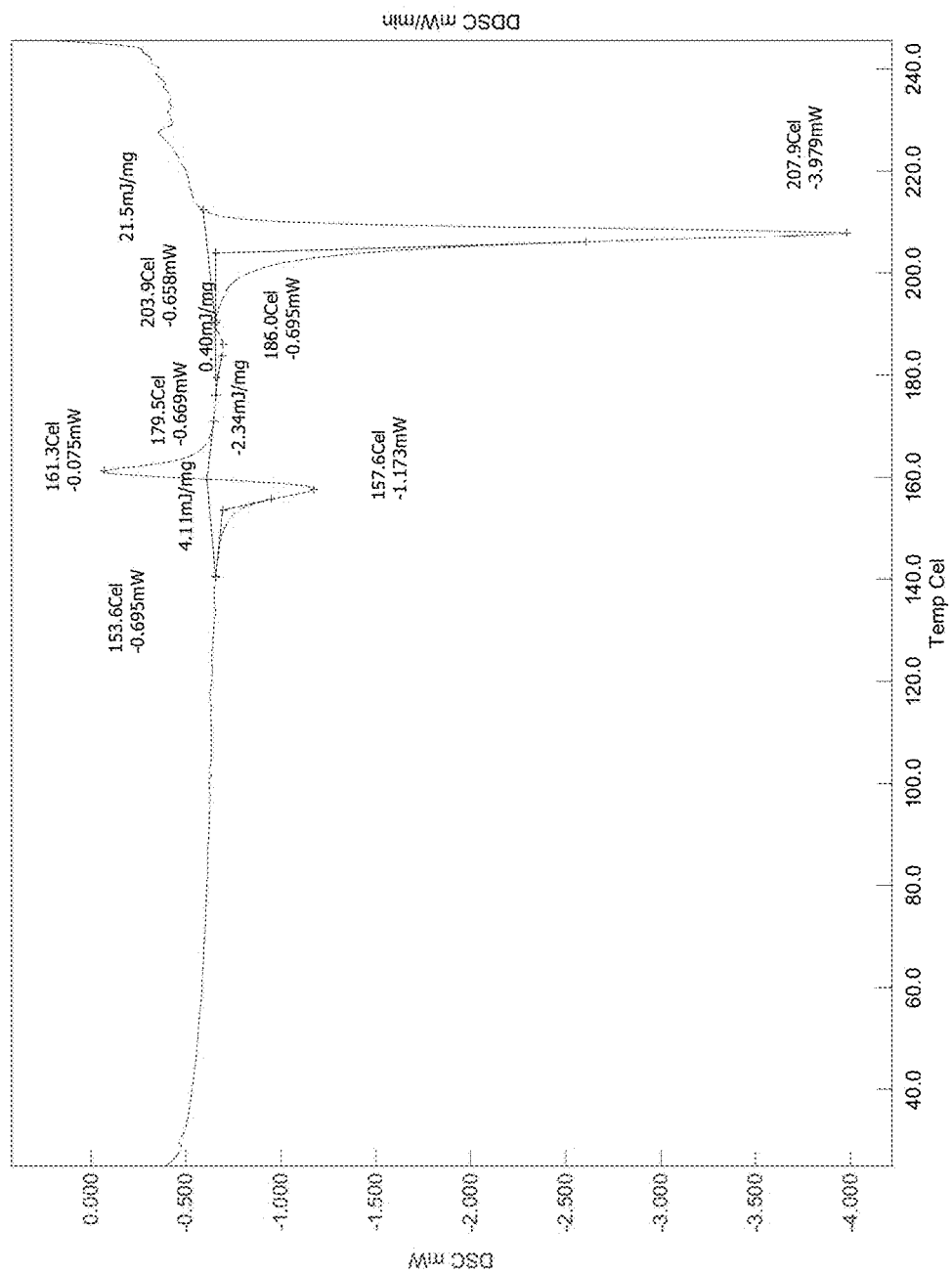
FIG. 8 depicts the DSC pattern for Form B of Compound 1.
Figure 9:
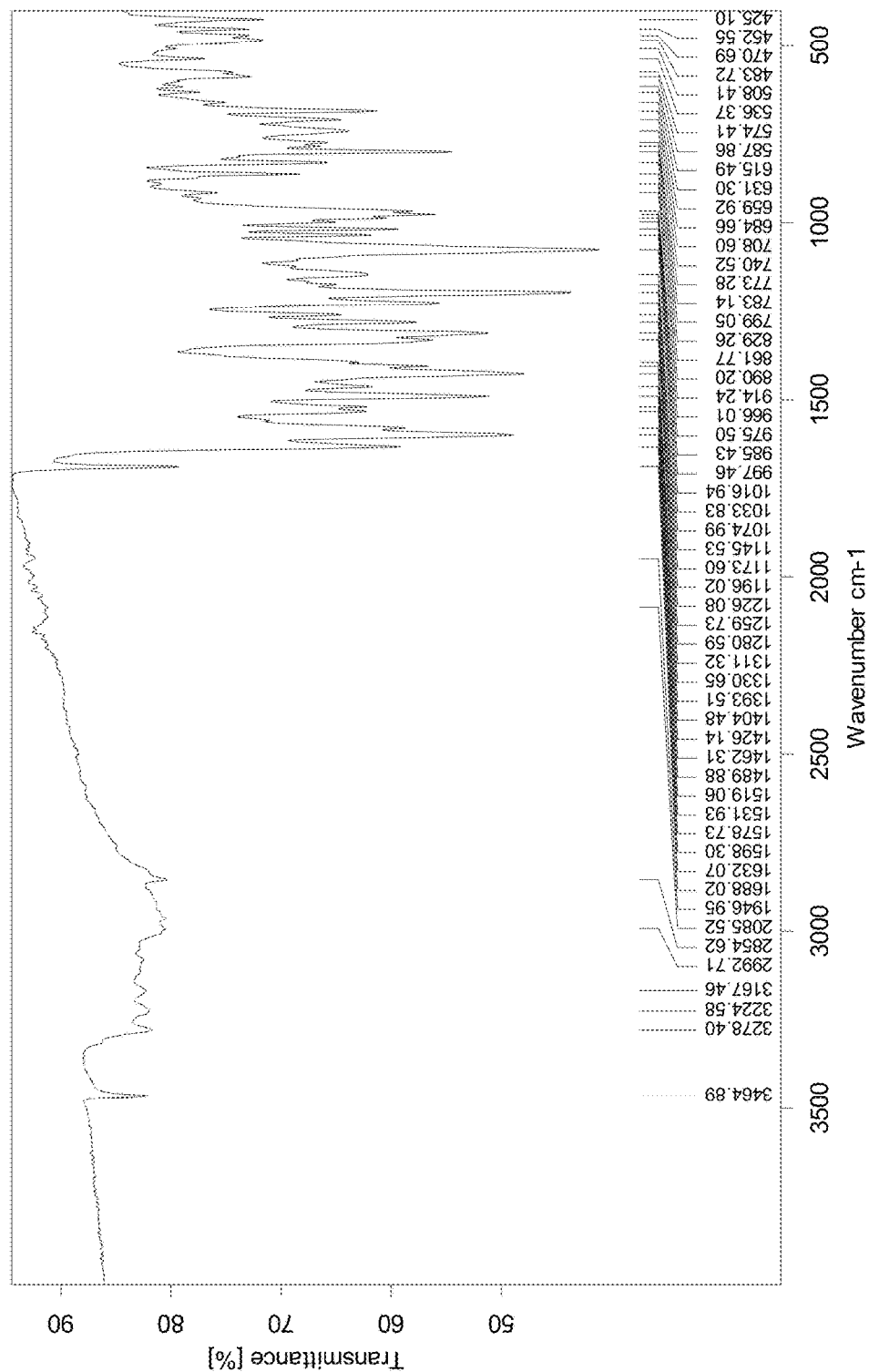
FIG. 9 depicts the IR spectrum for Form B of Compound 1.
Figure 10:
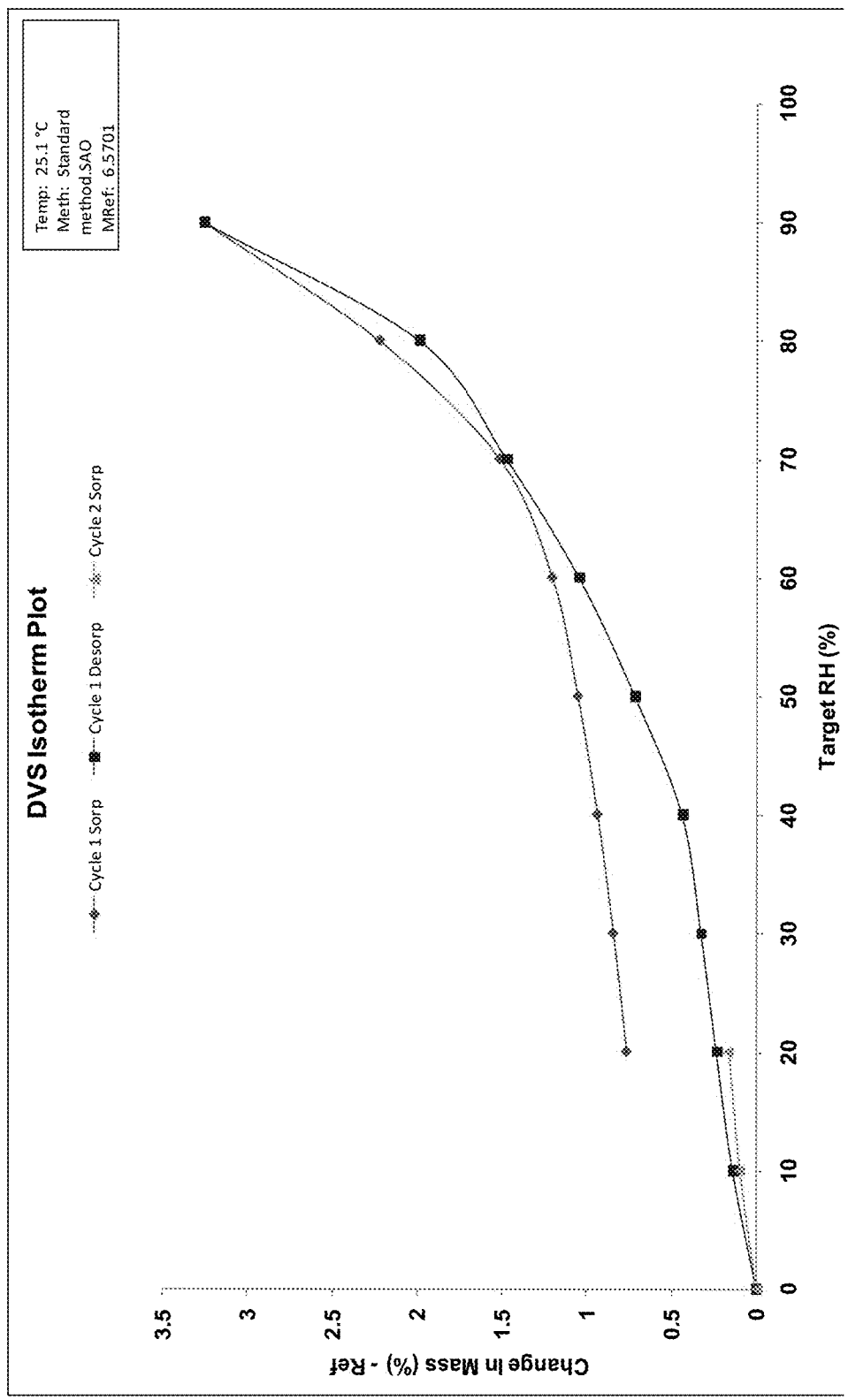
FIG. 10 depicts the DVS pattern for Form B of Compound 1.

According to one aspect, Form B of Compound 1 has a powder X-ray diffraction pattern substantially similar to that depicted in FIG. 6. According to another aspect, Form B of Compound 1 has a thermogravimetric analysts pattern substantially similar to that depicted in FIG. 7. Accordingly to yet another aspect, Form B of Compound 1 has a differential scanning calorimetry pattern substantially similar to that depicted in FIG. 8. According to a further embodiment, Form B of Compound 1 has an infrared spectrum substantially similar to that depicted in FIG. 9. According to another embodiment, Form B of Compound 1 has a dynamic vapour sorption pattern substantially similar to that depicted in FIG. 10. Form B of Compound 1 can be characterized by substantial similarity to two or more of these figures simultaneously.

In certain embodiments, Compound 1 is a dimethylformamide (DMF) solvate crystal form. In some embodiments, the present invention provides a DMF solvate polymorphic form of Compound 1 referred to herein as Form C.

In certain embodiments, the present invention provides Form C of Compound 1. According one embodiment, Form C of Compound 1 is characterized by one or more peaks in its powder X-ray diffraction pattern selected from those at about 16.32, about 18.22, about 20.26, about 22.58 and about 25.36 degrees 2-theta. In some embodiments, Form C of Compound 1 is characterized by two or more peaks in its powder X-ray diffraction pattern selected from those at about 16.32, about 12.82, about 20.26, about 22.58 and about 25.36 degrees 2-theta. In certain embodiments, Form C of Compound 1 is characterized by three or more peaks in its powder X-ray diffraction pattern selected from those at about 16.32, about 18.82, about 20.26, about 22.58 and about 25.36 degrees 2-theta. In particular embodiments, Form C of Compound 1 is characterized by substantially all of the peaks in its X-ray powder diffraction pattern selected from those at about 8.14, 14.45, 15.37, 16.33, 18.16, 18.82, 20.26, 22.58, 22.96, 24.33, 25.36 and 26.36 degrees 2-theta. In an exemplary embodiment, Form C of compound 1 is characterized by substantially all of the peaks in its X-ray powder diffraction pattern selected from those at about:

| °2-Theta |
| --- |
| 4.11 |
| 5.95 |
| 6.30 |
| 7.40 |
| 7.80 |
| 8.14 |
| 9.21 |
| 10.09 |
| 11.01 |
| 11.87 |
| 12.57 |
| 13.59 |
| 14.45 |
| 15.37 |
| 15.94 |
| 16.33 |
| 16.67 |
| 17.03 |
| 17.57 |
| 18.16 |
| 18.37 |
| 18.82 |
| 19.35 |
| 19.72 |
| 20.26 |
| 20.62 |
| 21.02 |
| 21.56 |
| 22.10 |
| 22.58 |
| 22.96 |
| 23.99 |
| 24.33 |
| 24.62 |
| 25.36 |
| 26.36 |
| 27.02 |
| 27.37 |
| 27.81 |
| 28.44 |
| 29.12 |
| 29.45 |
| 29.80 |
| 30.28 |
| 30.66 |
| 31.24 |
| 31.79 |
| 32.65 |
| 33.04 |
| 34.03 |
| 34.16 |
| 34.51 |
| 35.25 |
| 35.65 |
| 36.92 |
| 38.42 |
| 39.28 |
| 39.89 |
| 41.64 |
| 42.14 |
| 44.15 |
| 44.54 |
| 45.35 |
| 46.02 |
| 46.44 |
| 48.42 |
| 49.16 |

Figure 12:
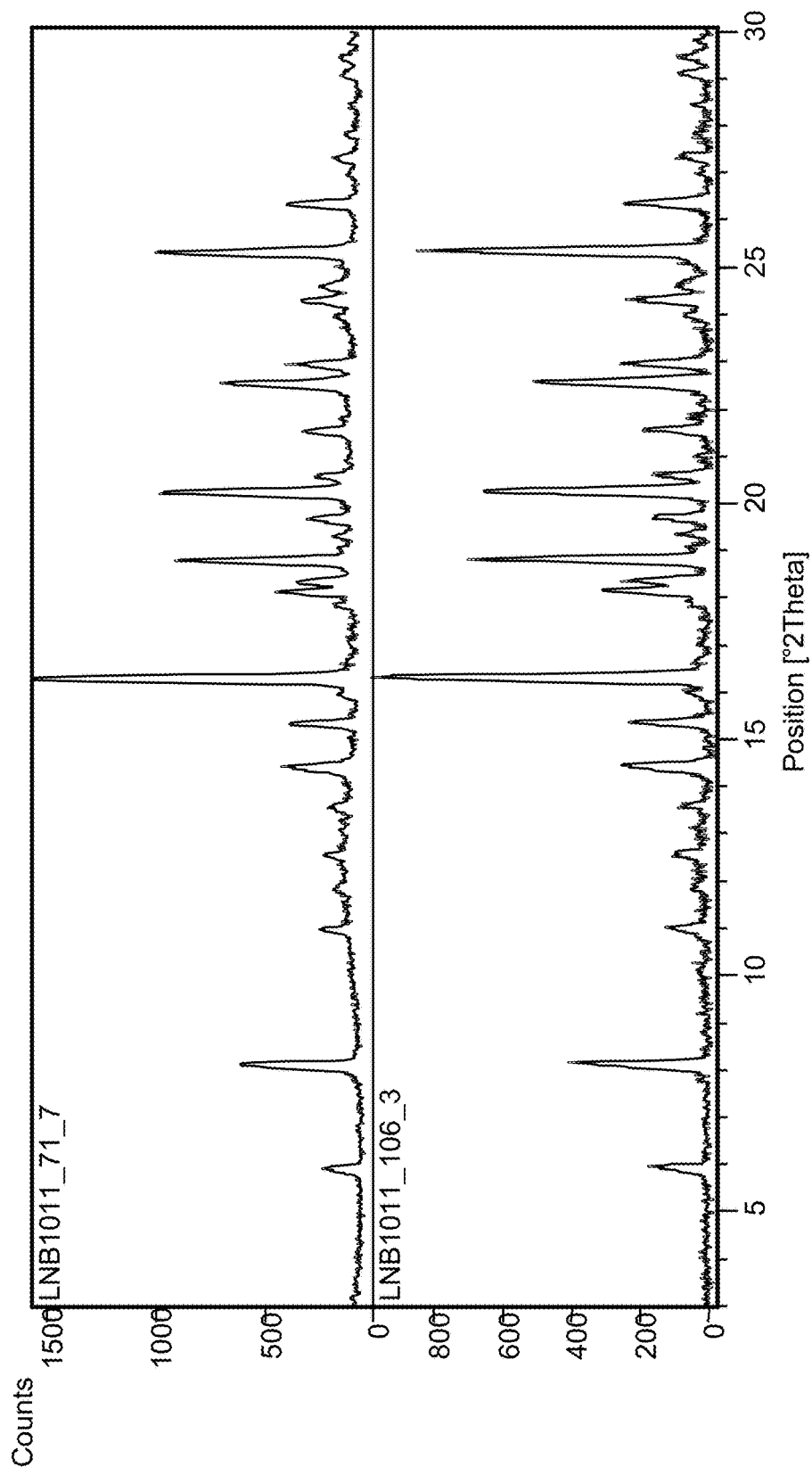
FIG. 12 depicts the XRPD pattern for Form C of Compound 1.
Figure 13:
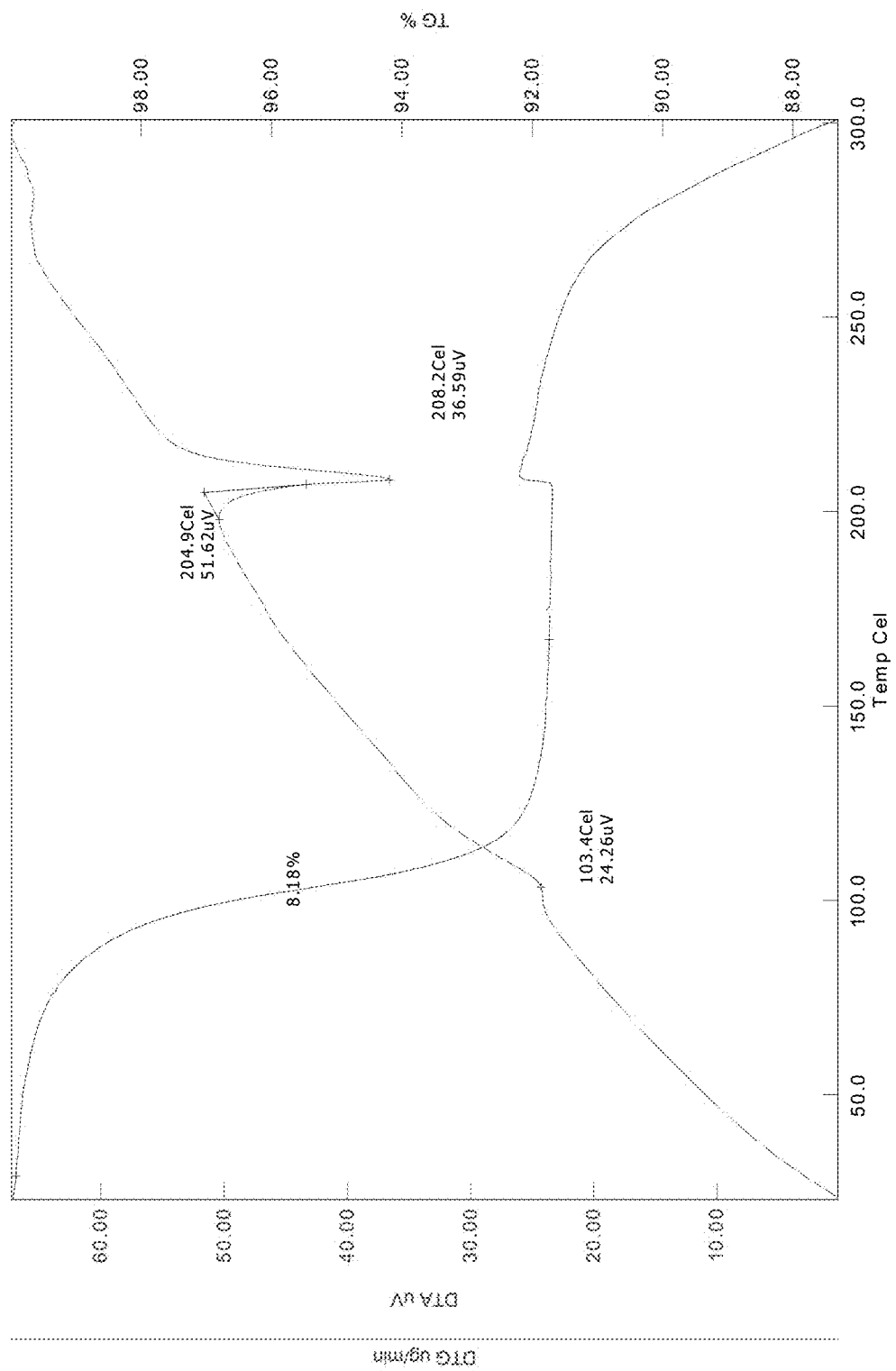
FIG. 13 depicts the TGA/DTA pattern for Form C of Compound 1.
Figure 14:
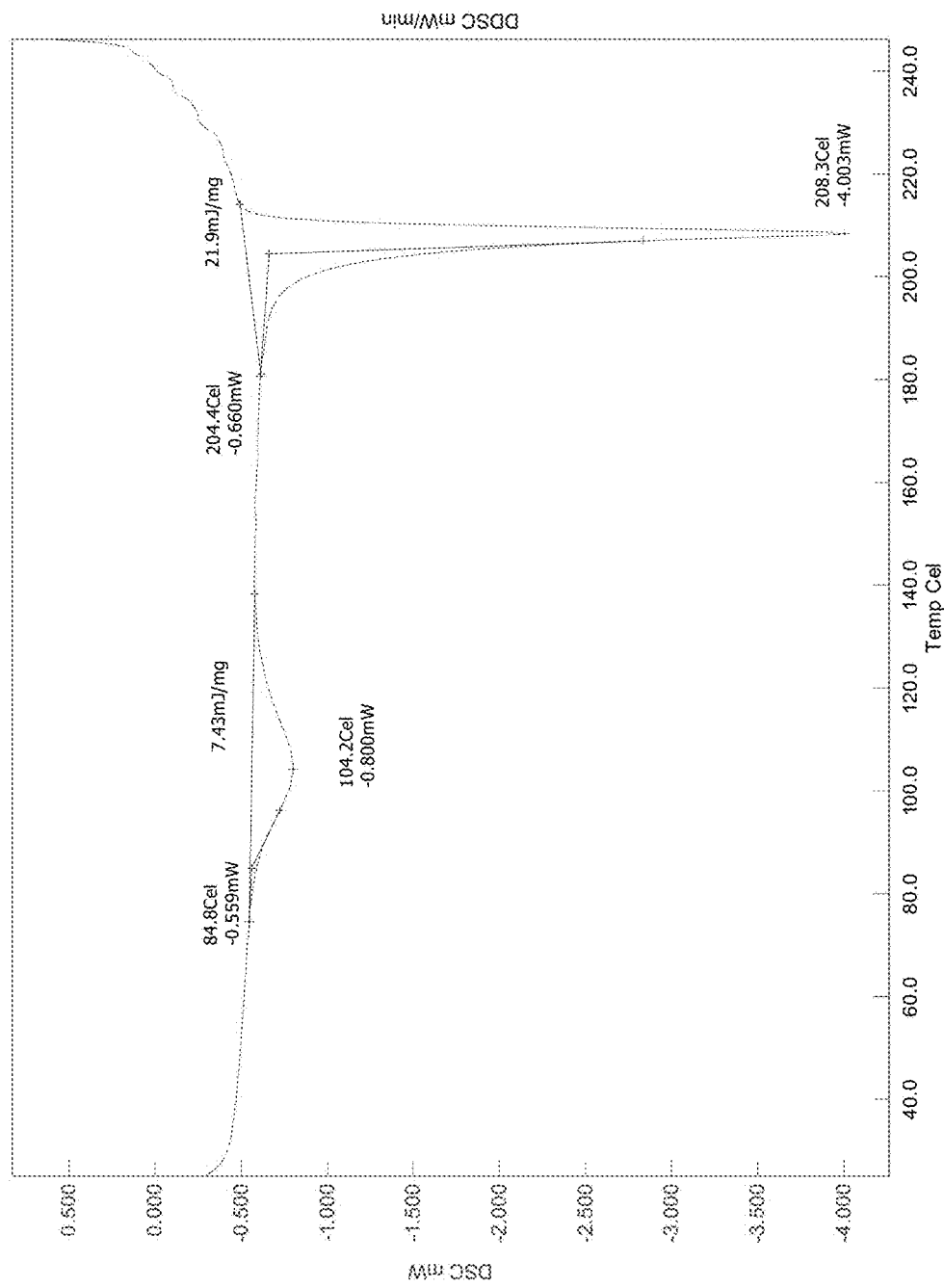
FIG. 14 depicts the DSC pattern for Form C of Compound 1.
Figure 15:
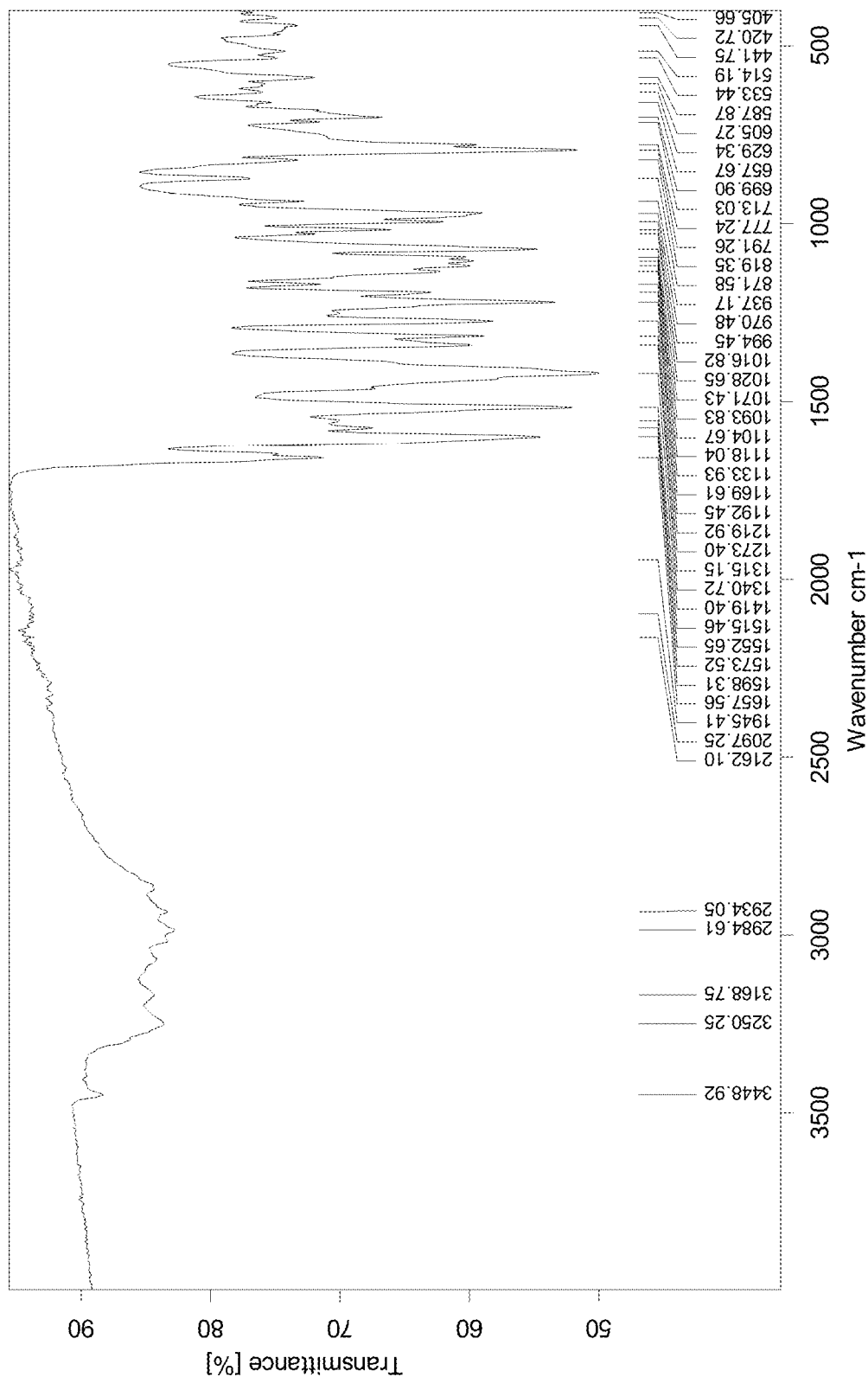
FIG. 15 depicts the IR spectrum for Form C of Compound 1.
Figure 16:
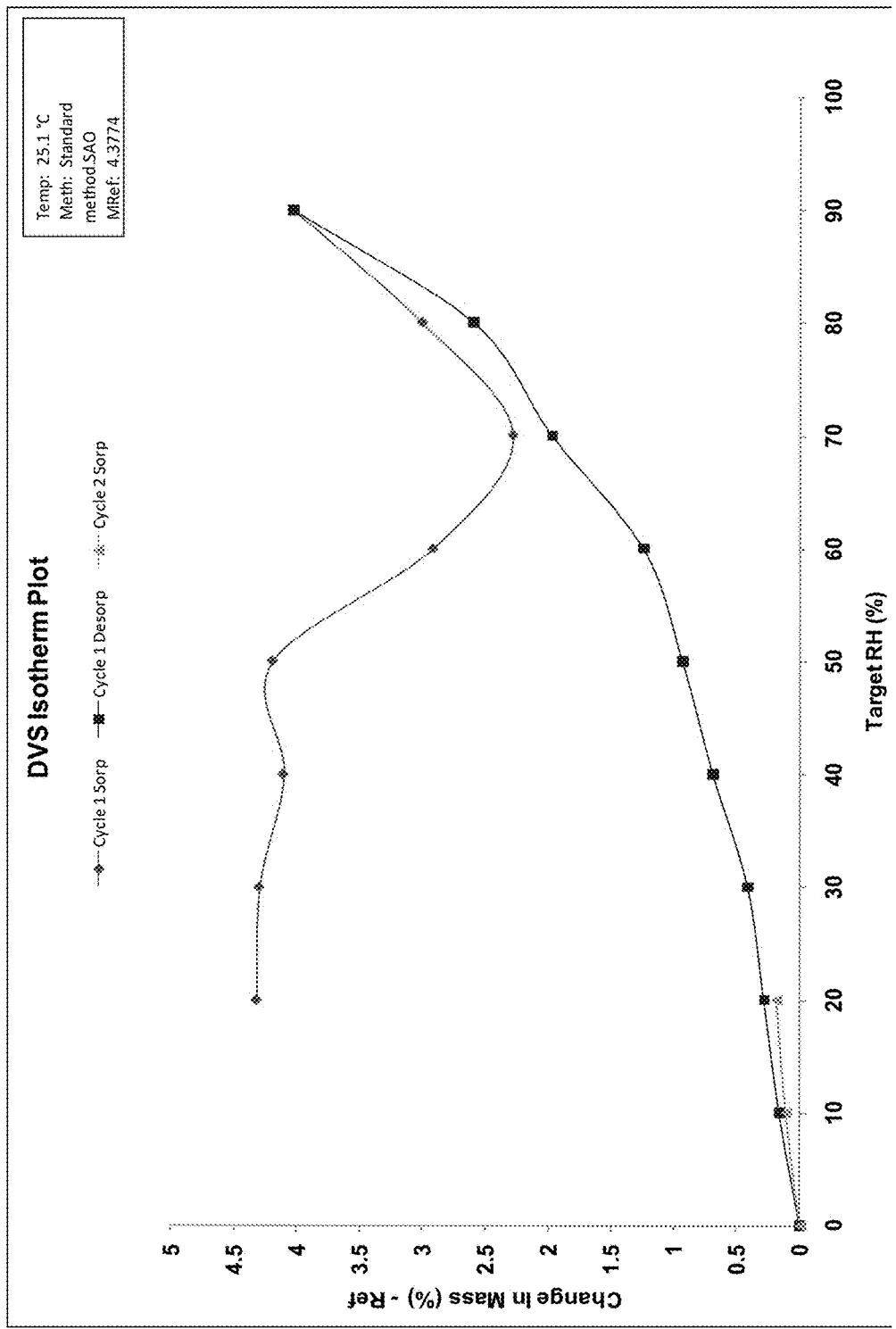
FIG. 16 depicts the DVS pattern for Form C of Compound 1.

According to one aspect, Form C of Compound 1 has a powder X-ray diffraction pattern substantially similar to that depicted in FIG. 12. According to another aspect, Form C of Compound 1 has a thermogravimetric analysis pattern substantially similar to that depicted in FIG. 13. Accordingly to yet another aspect, Form C of Compound 1 has a differential scanning calorimetry pattern substantially similar to that depicted in FIG. 14. According to a further embodiment, Form C of Compound 1 has a infrared spectrum substantially similar to that depicted in FIG. 15. According to another embodiment, Form C of Compound 1 has a dynamic vapour sorption pattern substantially similar to that depicted in FIG. 16. Form C of Compound 1 can be characterized by substantial similarity to two or more of these figures simultaneously.

In certain embodiments, Compound 1 is a 1,4-dioxane solvate crystal form. In some embodiments, the present invention provides a 1,4-dioxane solvate polymorphic form of Compound 1 referred to herein as Form D.

In certain embodiments, the present invention provides Form D of Compound 1. According one embodiment, Form D of Compound 1 is characterized by one or more peaks in its powder X-ray diffraction pattern selected from those at about 18.40, about 19.31, about 20.14, about 20.53 and about 25.25 degrees 2-theta. In some embodiments, Form D of Compound 1 is characterized by two or more peaks in its powder X-ray diffraction pattern selected from those at about 18.40, about 19.31, about 20.14, about 20.53 and about 25.25 degrees 2-theta. In certain embodiments, Form D of Compound 1 is characterized by three or more peaks in its powder X-ray diffraction pattern selected from those at about 18.40, about 19.31, about 20.14, about 20.53 and about 25.25 degrees 2-theta. In particular embodiments, Form D of Compound 1 is characterized by substantially all of the peaks in its X-ray powder diffraction pattern selected from those at about 13.51, 16.97, 17.86, 18.40, 19.31, 20.14, 20.53, 21.04, 22.50, 24.98 and 25.25 degrees 2-theta. In an exemplary embodiment, Form D of Compound 1 is characterized by substantially all of the peaks in its X-ray powder diffraction pattern selected from those at about:

| °2-Theta |
| --- |
| 3.03 |
| 3.30 |
| 5.49 |
| 6.60 |
| 6.86 |
| 7.21 |
| 7.56 |
| 8.93 |
| 9.87 |
| 10.11 |
| 10.68 |
| 11.36 |
| 12.22 |
| 13.51 |
| 14.61 |
| 14.92 |
| 15.26 |
| 16.15 |
| 16.45 |
| 16.61 |
| 16.97 |
| 17.86 |
| 18.40 |
| 18.77 |
| 19.31 |
| 20.14 |
| 20.53 |
| 21.04 |
| 21.52 |
| 22.50 |
| 23.80 |
| 24.98 |
| 25.25 |
| 25.64 |
| 26.35 |
| 26.60 |
| 26.82 |
| 27.21 |
| 28.19 |

| °2-Theta |
| --- |
| 28.90 |
| 29.86 |

Figure 19:
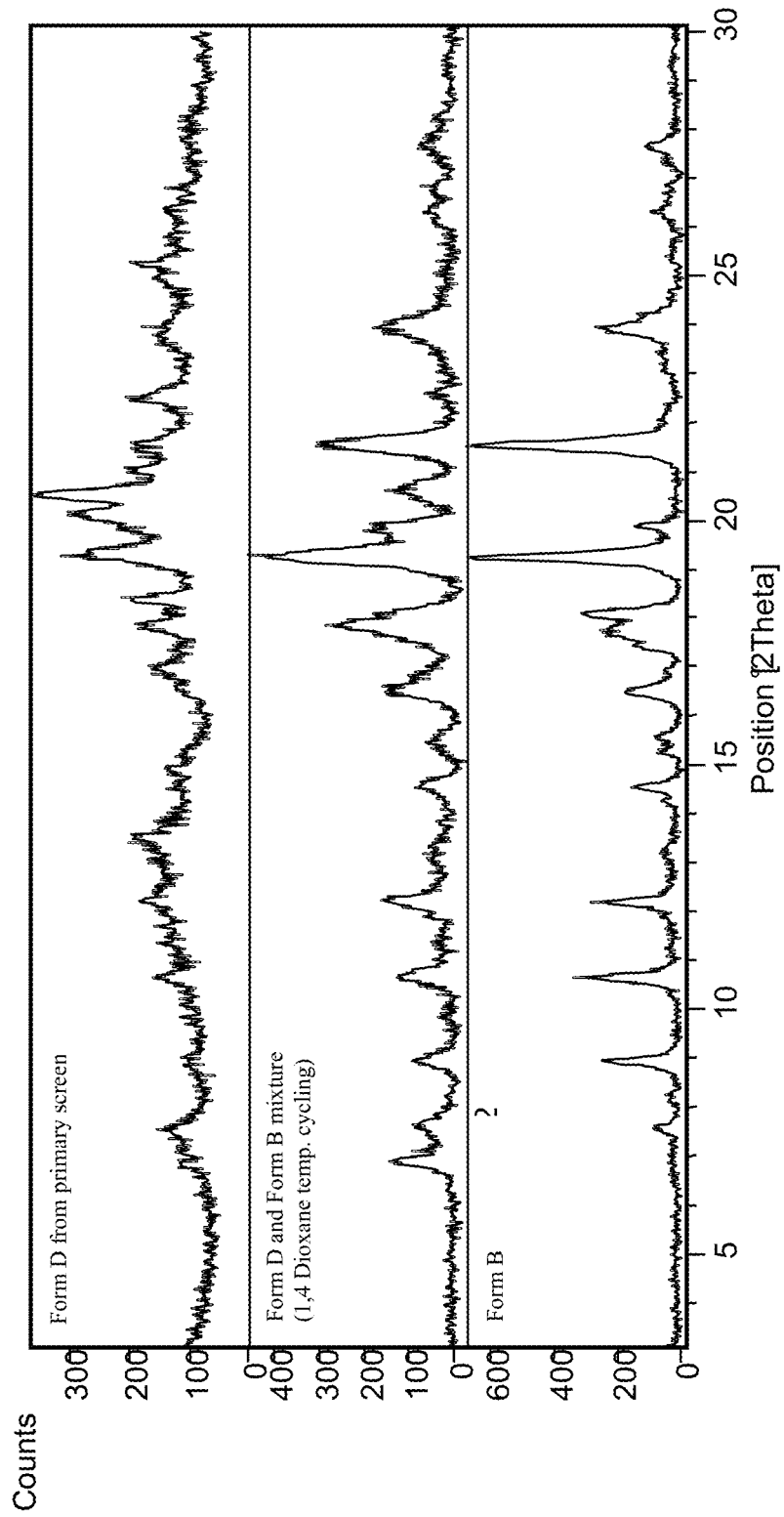
FIG. 19 depicts the XRPD pattern for Form D of Compound 1, which is present in a mixture with Form B.
Figure 20A:
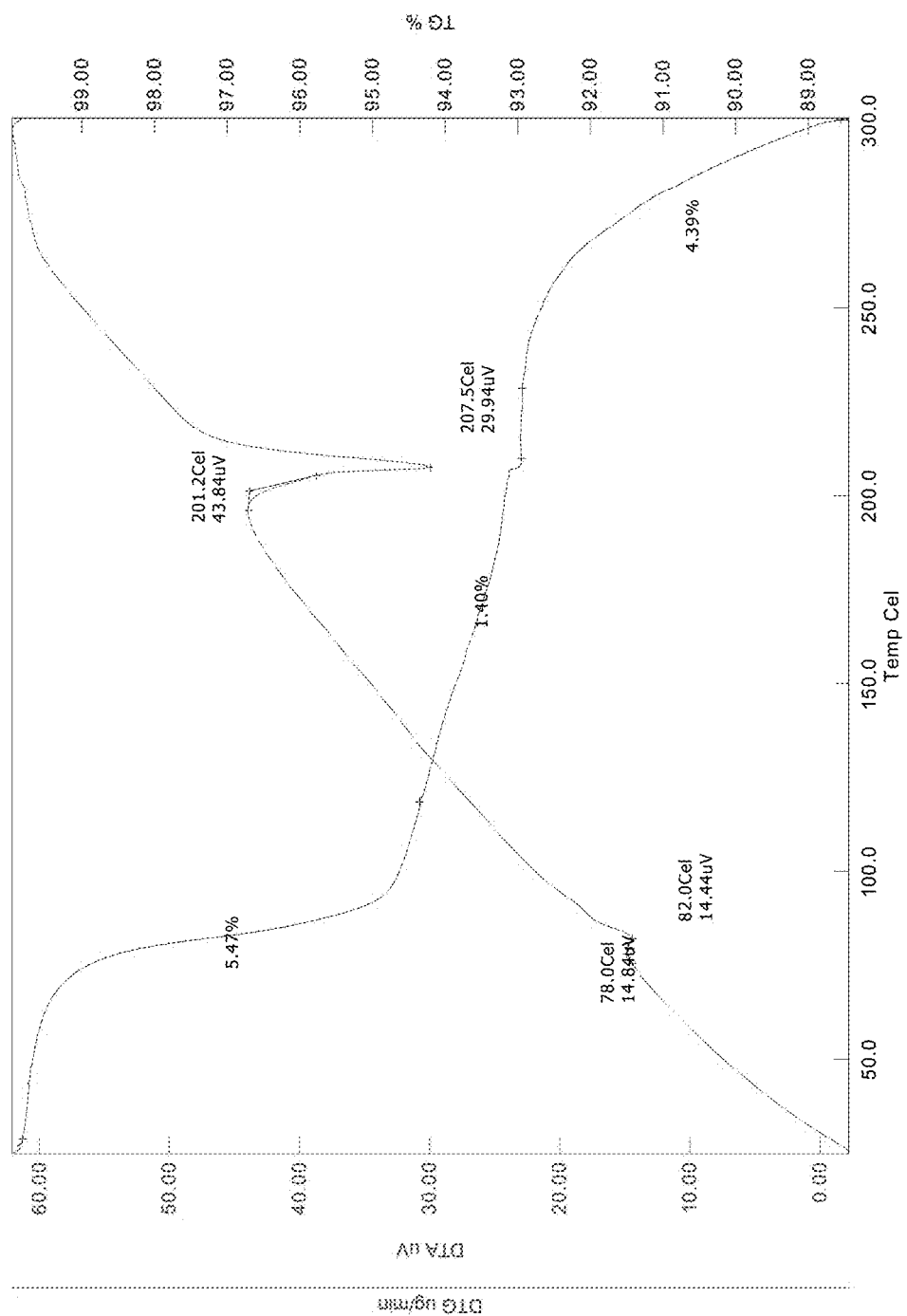
FIGS. 20A and B depict TGA/DTA patterns for Form D of Compound 1.
Figure 20B:
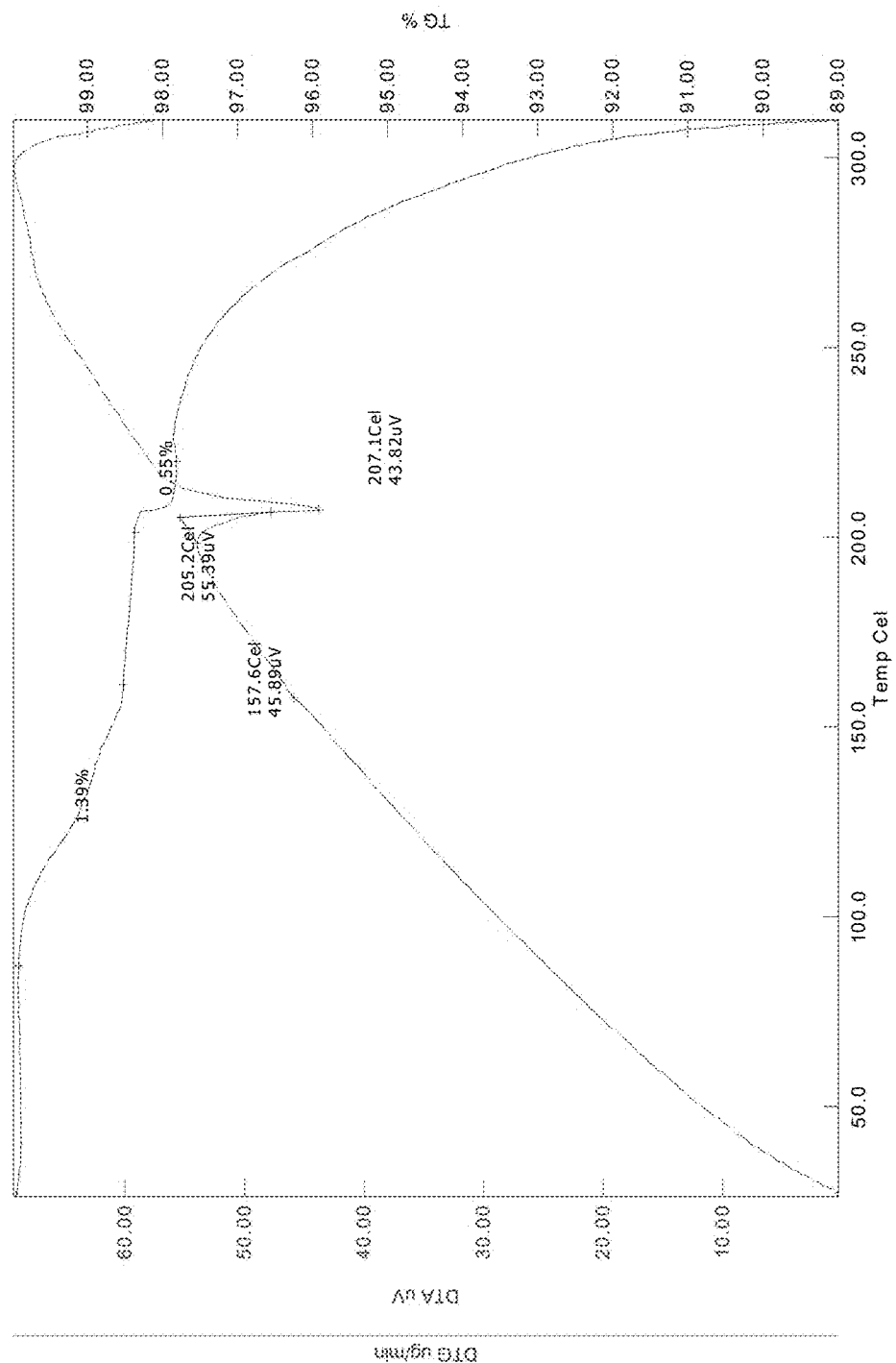
Figure 21:
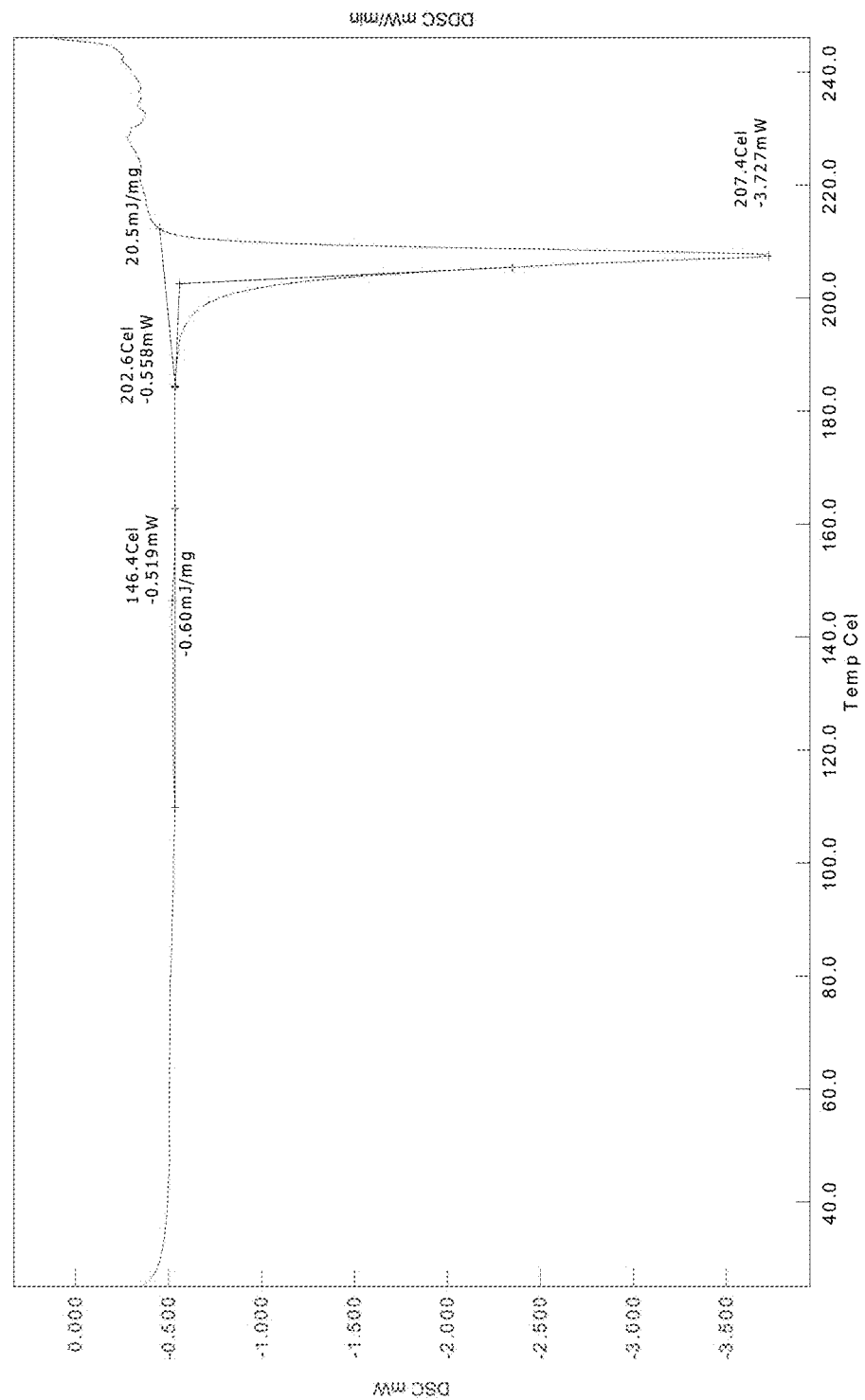
FIG. 21 depicts the DSC pattern for Form D of Compound 1.
Figure 22:
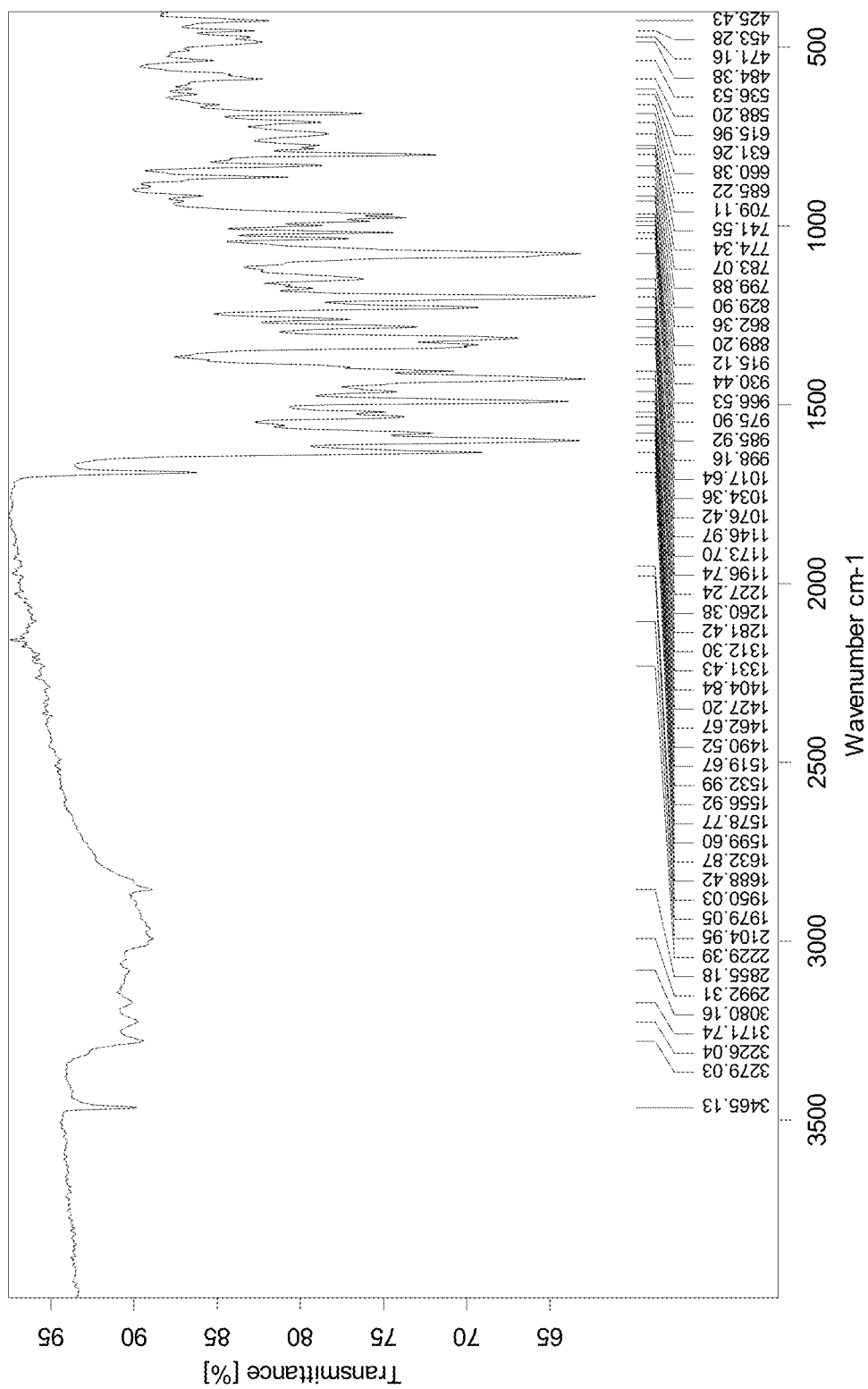
FIG. 22 depicts the IR spectrum for Form D of Compound 1.
Figure 23:
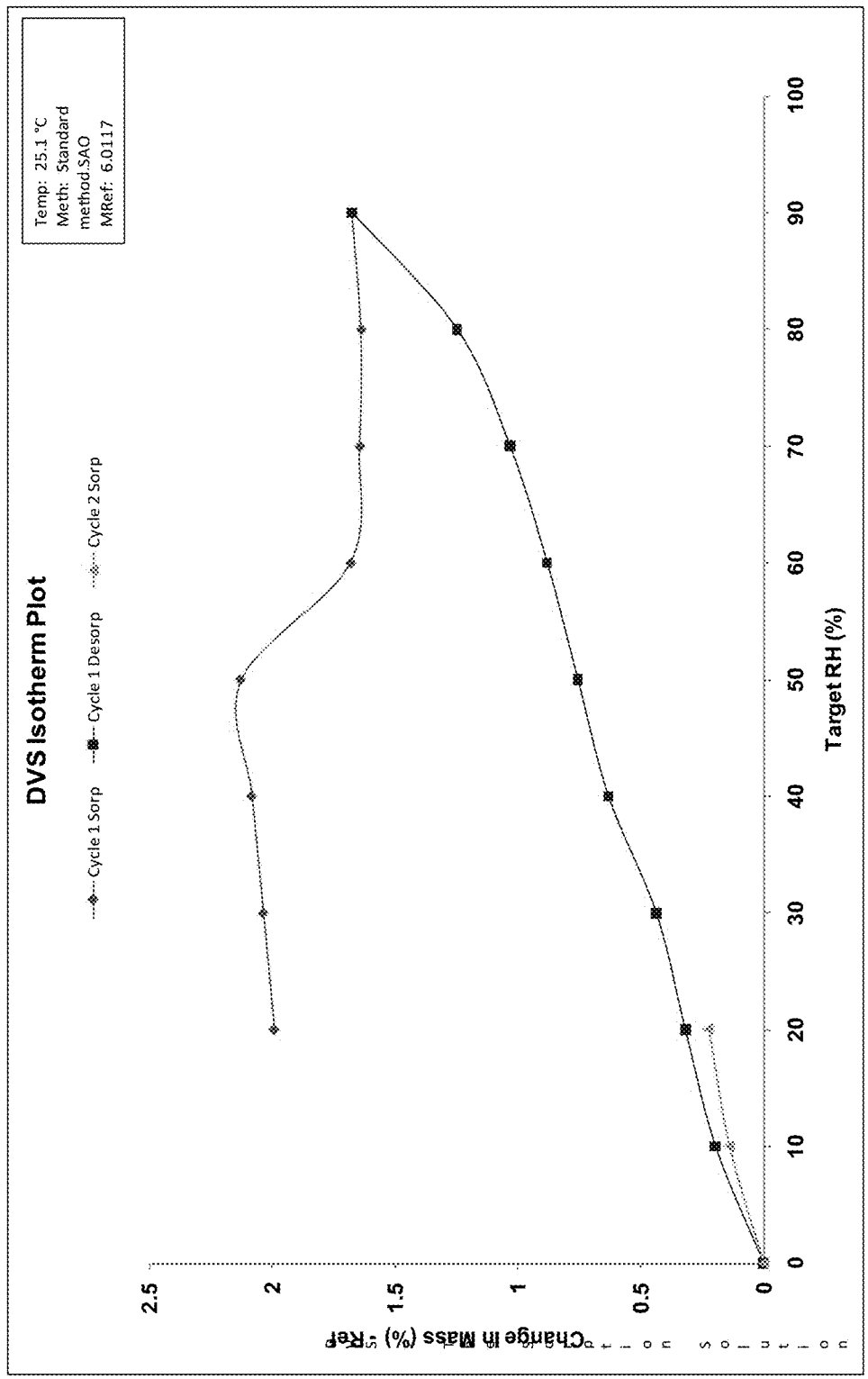
FIG. 23 depicts the DVS pattern for Form D of Compound 1.

According to one aspect, Form D of Compound 1 has a powder X-ray diffraction pattern substantially similar to that depicted in FIG. 19. According to another aspect, Form D of Compound 1 has a thermogravimetric analysis pattern substantially similar to that depicted in FIG. 20A or 20B. Accordingly to yet another aspect, Form D of Compound 1 has a differential scanning calorimetry pattern substantially similar to that depicted in FIG. 21. According to a further embodiment, Form D of Compound 1 has an infrared spectrum substantially similar to that depicted in FIG. 22. According to another embodiment, Form D of Compound 1 has a dynamic vapour sorption pattern substantially similar to that depicted in FIG. 23. Form D of Compound 1 can be characterized by substantial similarity to two or more of these figures simultaneously.

In certain embodiments, Compound 1 is a methyl ethyl ketone (MEK) crystal form. In some embodiments, the present invention provides a MEK solvate polymorphic form of Compound 1 referred to herein as Form E.

In certain embodiments, the present invention provides Form E of Compound 1. According one embodiment, Form E of Compound 1 is characterized by one or more peaks in its powder X-ray diffraction pattern selected from those at about 5.78, about 12.57, about 15.34, about 19.10 and about 24.80 degrees 2-theta. In some embodiments, Form E of Compound 1 is characterized by two or more peaks in its powder X-ray diffraction pattern selected from those at about 5.78, about 12.57, about 15.34, about 19.10 and about 24.80 degrees 2-theta. In certain embodiments, Form E of Compound 1 is characterized by three or more peaks in its powder X-ray diffraction pattern selected from those at about 5.78, about 12.57, about 15.34, about 19.10 and about 24.80 degrees 2-theta. In particular embodiments, Form E of Compound 1 is characterized by substantially all of the peaks in its X-ray powder diffraction pattern selected from those at about 5.78, 12.38, 12.57, 14.14, 15.34, 18.22, 19.10, 20.05, 24.36 and 24.80 degrees 2-theta. In an exemplary embodiment, Form E of Compound 1 is characterized by substantially all of the peaks in its X-ray powder diffraction pattern selected from those at about:

| °2-Theta |
| --- |
| 3.96 |
| 5.78 |
| 7.32 |
| 8.05 |
| 9.06 |
| 9.34 |
| 10.09 |
| 10.66 |
| 11.67 |
| 12.38 |
| 12.57 |
| 13.92 |
| 14.14 |
| 15.34 |
| 15.66 |
| 16.28 |
| 16.84 |
| 17.56 |
| 17.97 |
| 18.22 |
| 18.84 |
| 19.10 |
| 20.05 |
| 20.81 |
| 21.04 |
| 22.23 |
| 23.12 |
| 24.36 |
| 24.80 |
| 26.45 |
| 27.20 |
| 28.68 |
| 29.37 |
| 29.70 |
| 30.13 |
| 30.70 |
| 32.37 |
| 33.06 |
| 33.43 |
| 34.37 |
| 35.75 |
| 39.30 |
| 41.13 |
| 47.08 |

Figure 25:
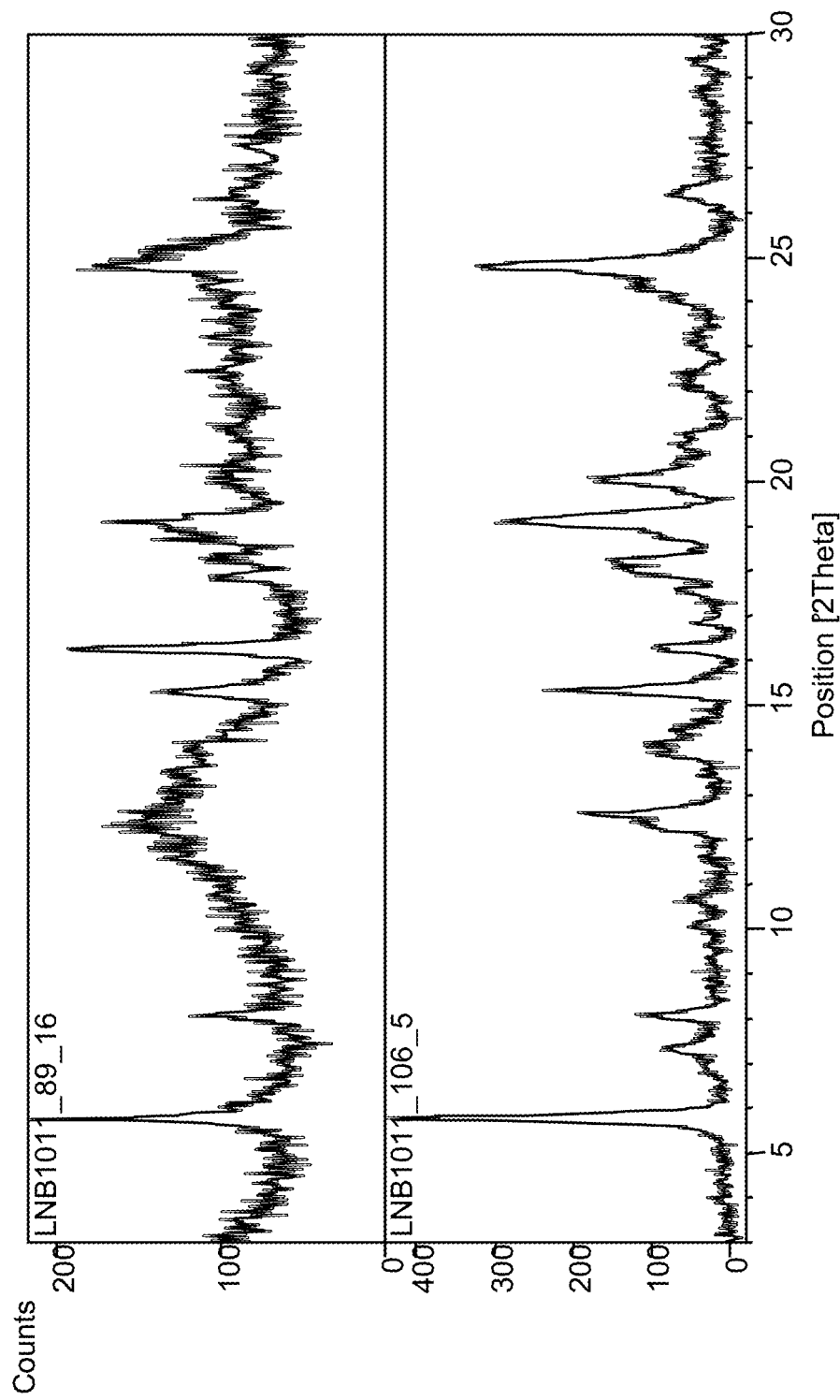
FIG. 25 depicts the XRPD pattern for Form E of Compound 1.
Figure 26:
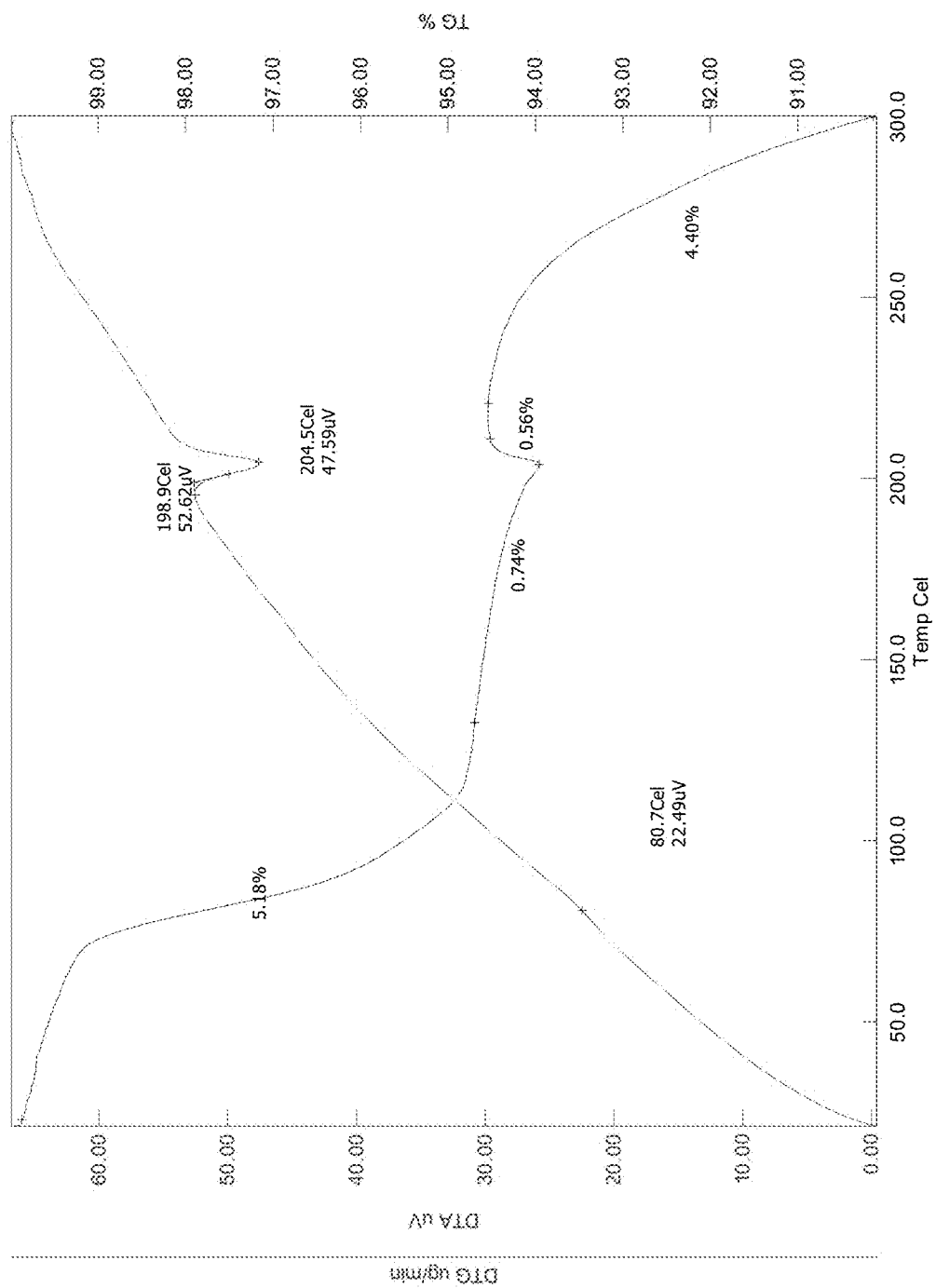
FIG. 26 depicts the TGA/DTA pattern for Form E of Compound 1.
Figure 27:
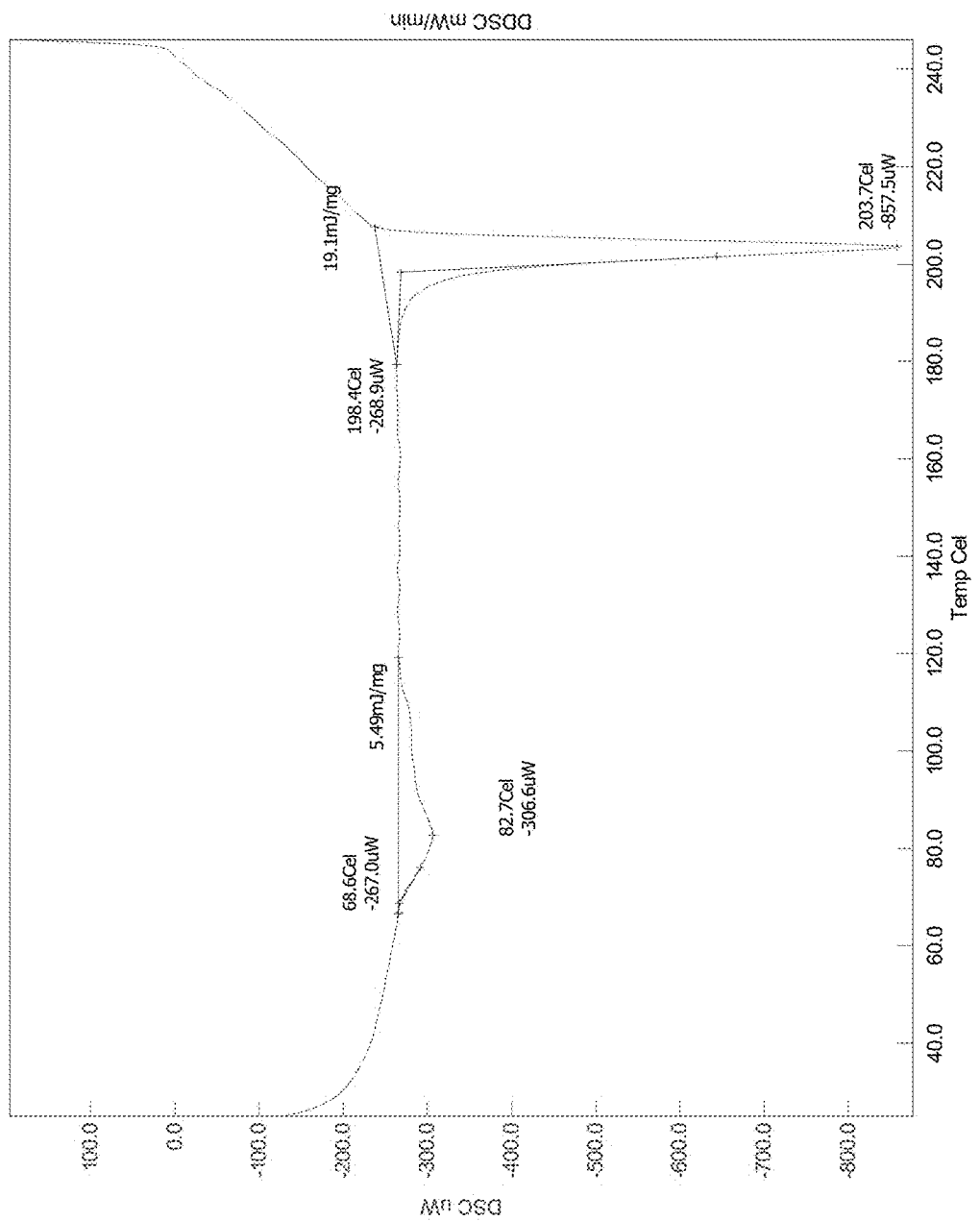
FIG. 27 depicts the DSC pattern for Form E of Compound 1.
Figure 28:
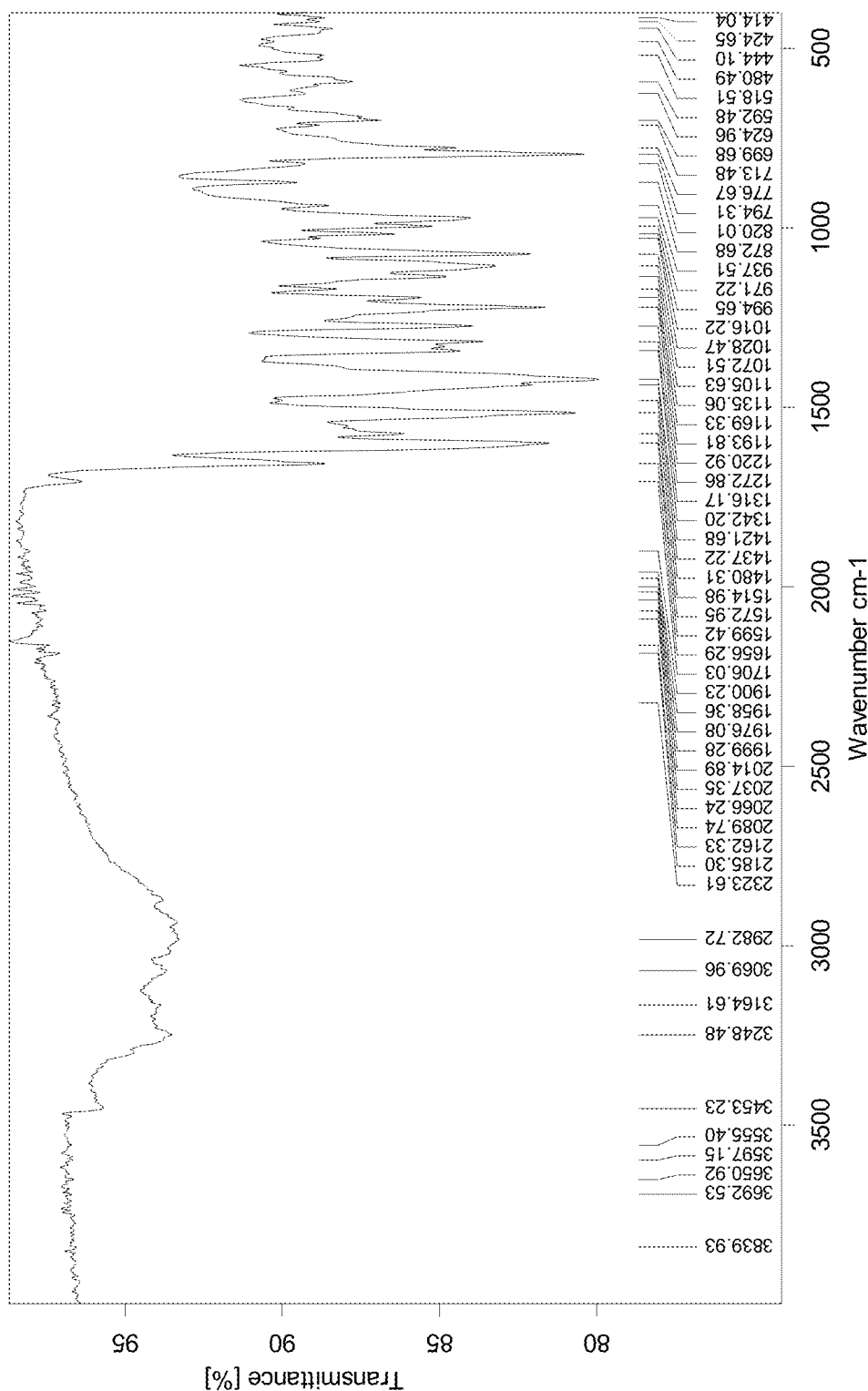
FIG. 28 depicts the IR spectrum for Form E of Compound 1.
Figure 29:
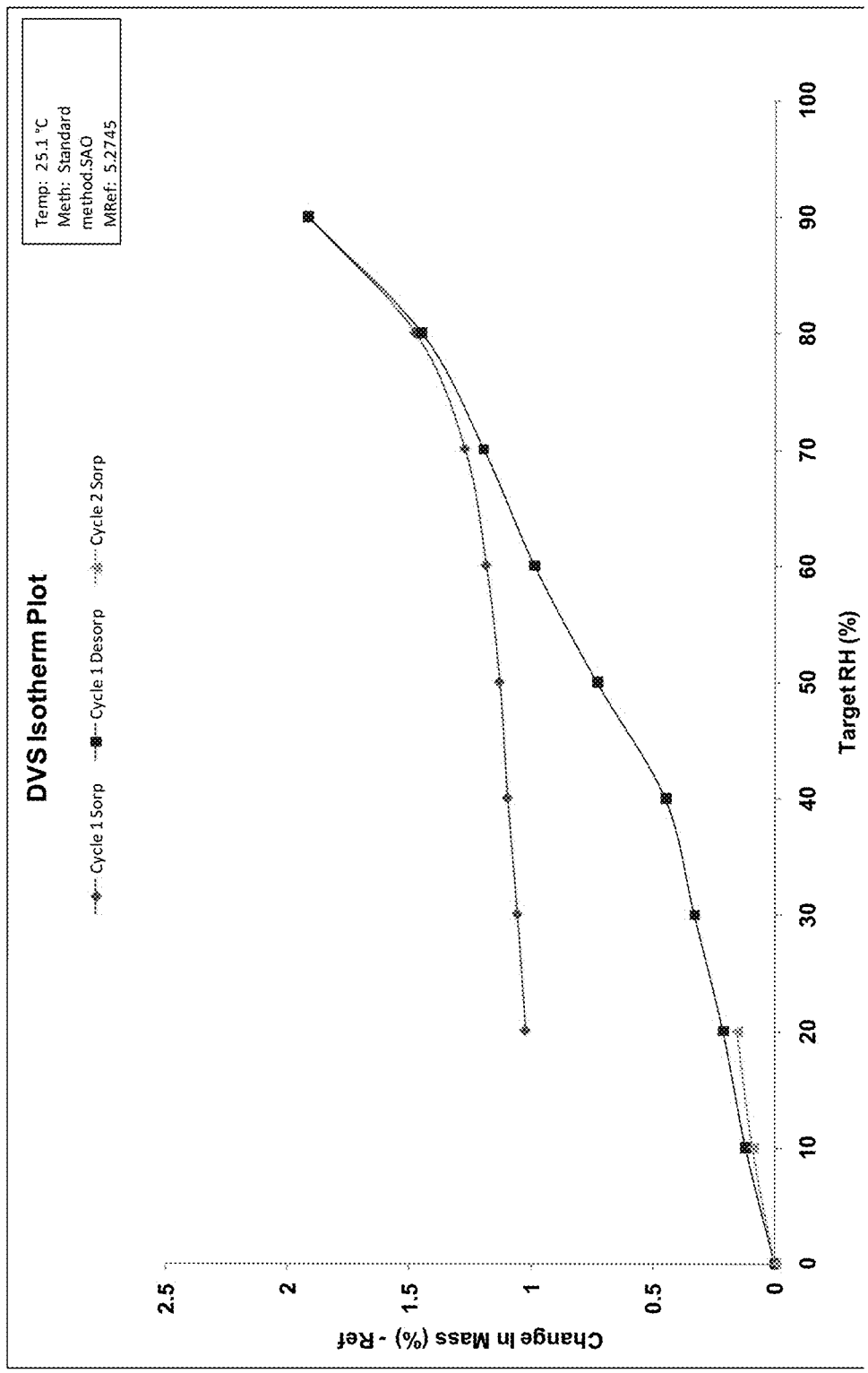
FIG. 29 depicts the DVS pattern for Form E of Compound 1.

According to one aspect, Form E of Compound 1 has a Powder X-ray diffraction pattern substantially similar to that depicted in FIG. 25. According to another aspect, Form E of Compound 1 has a thermogravimetric analysis pattern substantially similar to that depicted in FIG. 26. Accordingly to yet another aspect, Form E of Compound 1 has a differential scanning calorimetry pattern substantially similar to that depicted in FIG. 27. According to a further embodiment, Form E of Compound 1 has a infrared spectrum substantially similar to that depicted in FIG. 28. According to another embodiment, Form E of Compound 1 has a dynamic vapour sorption pattern substantially similar to that depicted in FIG. 29. Form E of Compound 1 can be characterized by substantial similarity to two or more of these figures simultaneously.

In certain embodiments, Compound 1 is a N-methyl-2-pyrrolidone (NMP) solvate crystal form. It has been found that Compound 1 can exist in at least two distinct NMP crystal forms, or polymorphs. In some embodiments, the present invention provides a NMP solvate polymorphic form of Compound 1 referred to herein as Form F. In other embodiments, the present invention provides a NMP solvate polymorphic form of Compound 1 referred to herein as Form G.

In certain embodiments, the present invention provides Form F of Compound 1. According one embodiment, Form F of Compound 1 is characterized by one or more peaks in its powder X-ray diffraction pattern selected from those at about 15.51, about 16.86, about 18.80, about 20.97 and about 23.32 degrees 2-theta. In some embodiments, Form F of Compound 1 is characterized by two or more peaks in its powder X-ray diffraction pattern selected from those at about 15.51, about 16.86, about 18.80, about 20.97 and about 23.32 degrees 2-theta. In certain embodiments, Form F of Compound 1 is characterized by three or more peaks in its powder X-ray diffraction pattern selected from those at about 15.51, about 16.86, about 18.80, about 20.97 and about 21.32 degrees 2-theta. In particular embodiments, Form F of Compound 1 is characterized by substantially all of the peaks in its X-ray powder diffraction pattern selected from those at about 5.64, 10.32, 12.97, 13.54, 15.51, 16.39, 16.86, 18.80, 19.16, 20.97, 23.32 and 24.55 degrees 2-theta. In an exemplary embodiment, Form F of Compound 1 is characterized by substantially all of the peaks in its X-ray powder diffraction pattern selected from those at about:

| °2-Theta |
|---|
| 3.68 |
| 3.87 |
| 5.10 |
| 5.64 |
| 5.81 |
| 7.34 |
| 8.21 |
| 9.81 |
| 10.32 |
| 12.97 |
| 13.54 |
| 14.12 |
| 15.00 |
| 15.51 |
| 16.39 |
| 16.86 |
| 17.36 |
| 18.80 |
| 19.16 |
| 19.68 |
| 20.08 |
| 20.97 |
| 21.93 |
| 22.64 |
| 23.32 |
| 23.87 |
| 24.55 |
| 25.25 |
| 25.71 |
| 26.22 |
| 26.40 |
| 26.64 |
| 27.07 |
| 27.76 |
| 28.98 |
| 30.11 |
| 30.95 |
| 31.16 |
| 31.46 |
| 34.04 |
| 34.56 |
| 35.72 |
| 36.70 |
| 37.60 |
| 38.68 |
| 39.55 |
| 40.14 |
| 40.87 |
| 41.96 |
| 44.15 |
| 44.69 |
| 45.38 |
| 48.22 |

Figure 32:
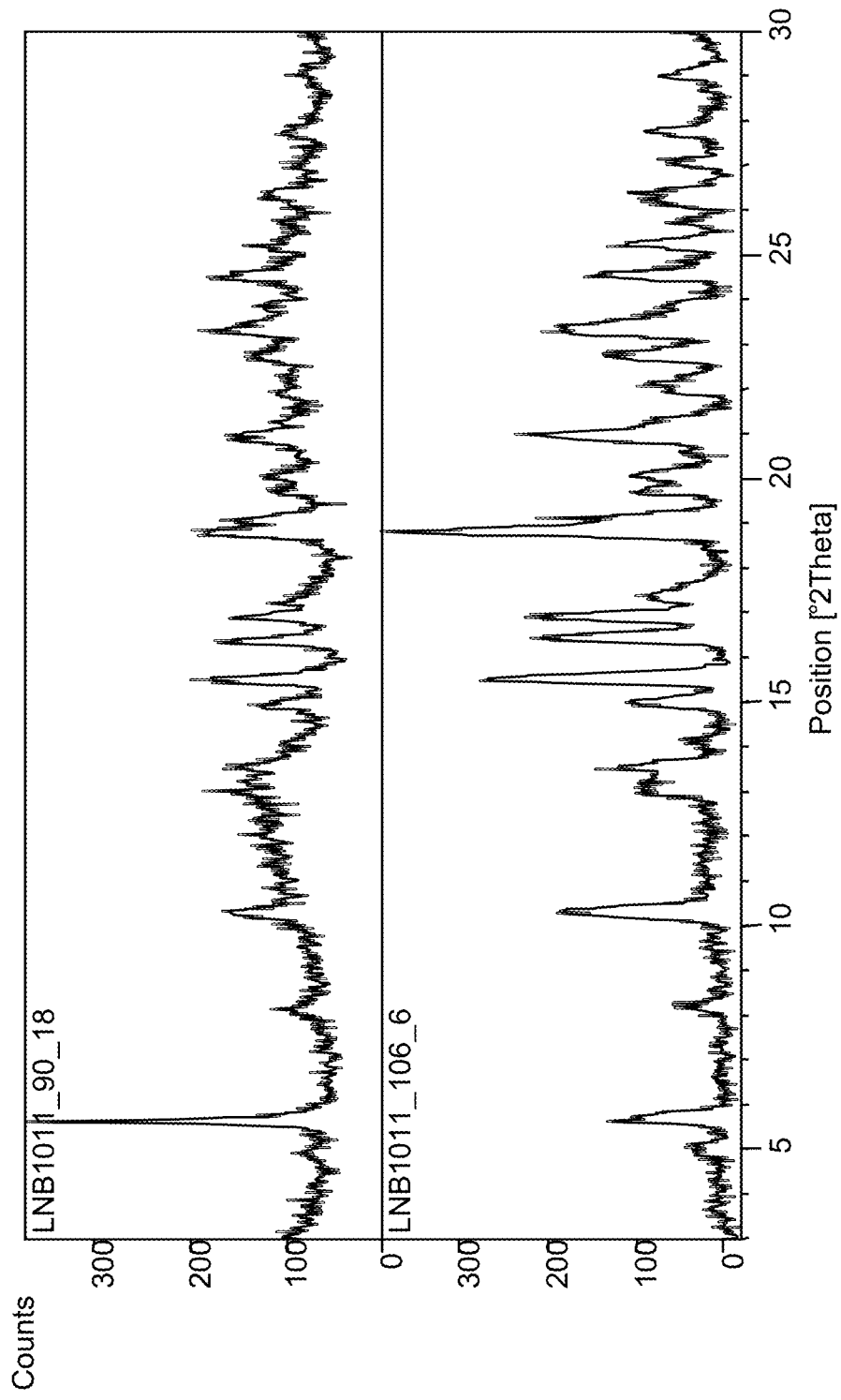
FIG. 32 depicts the XRPD pattern for Form F of Compound 1.
Figure 33:
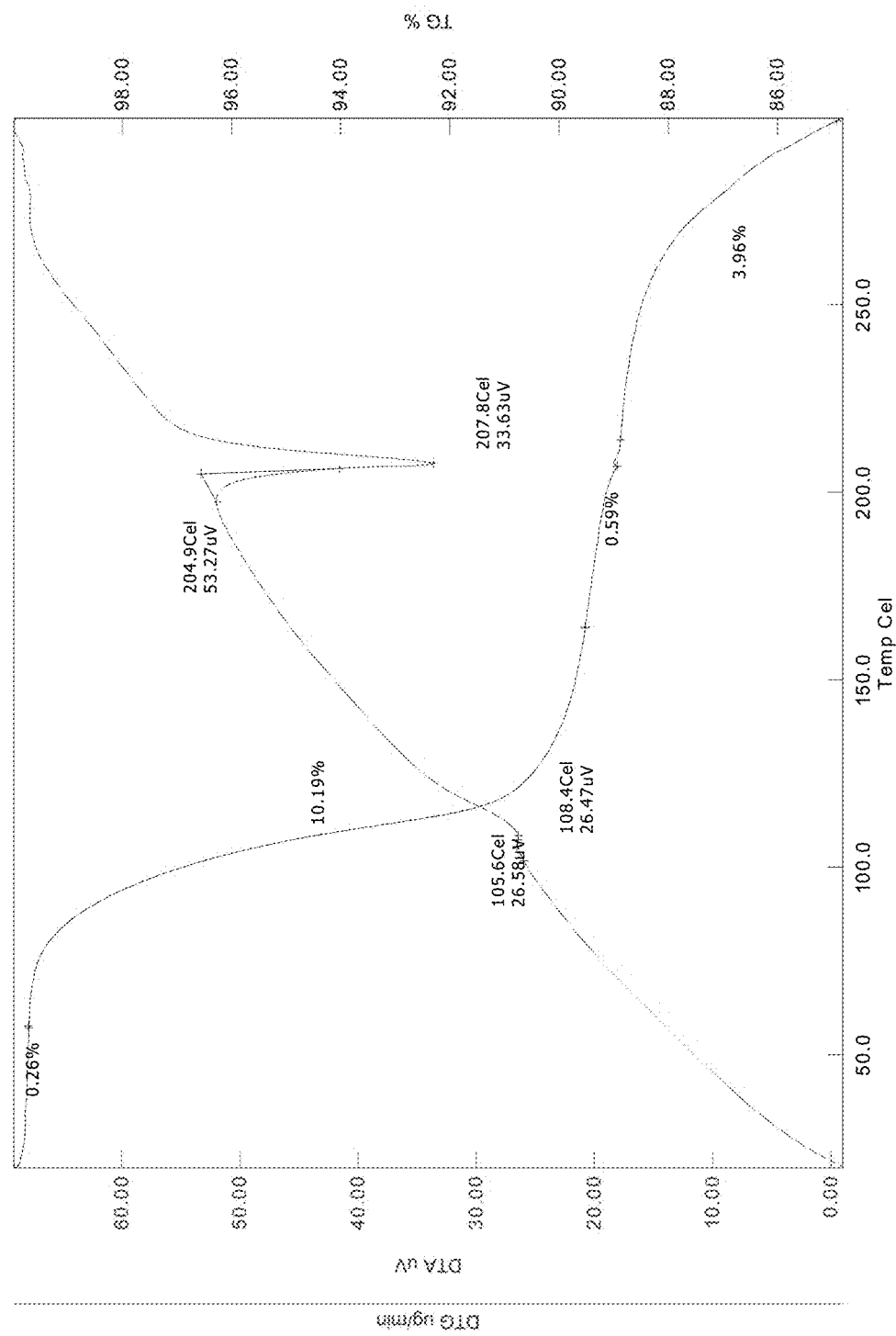
FIG. 33 depicts the TGA/DTA pattern for Form F of Compound 1.
Figure 34:
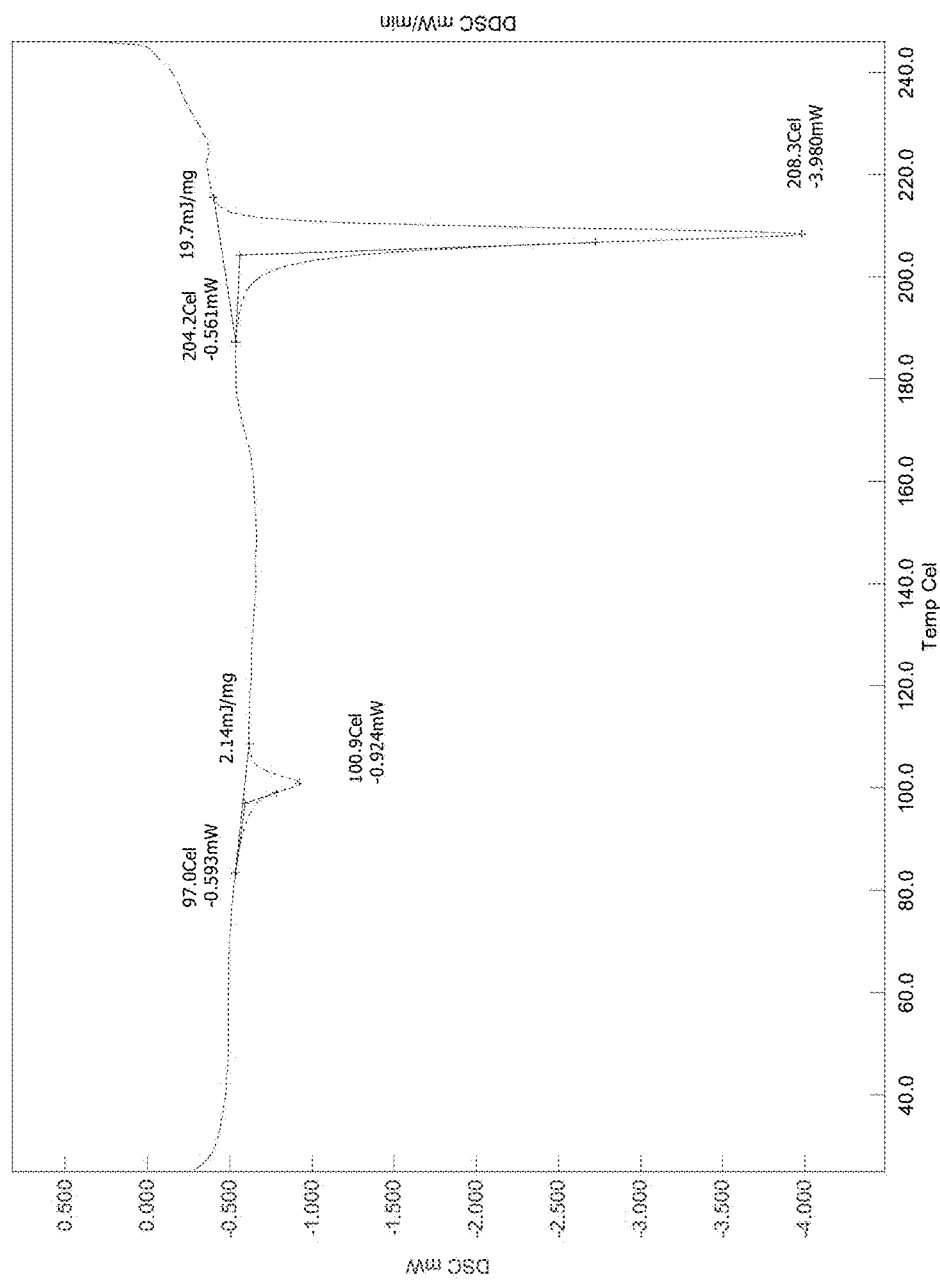
FIG. 34 depicts the DSC pattern for Form F of Compound 1.
Figure 35:
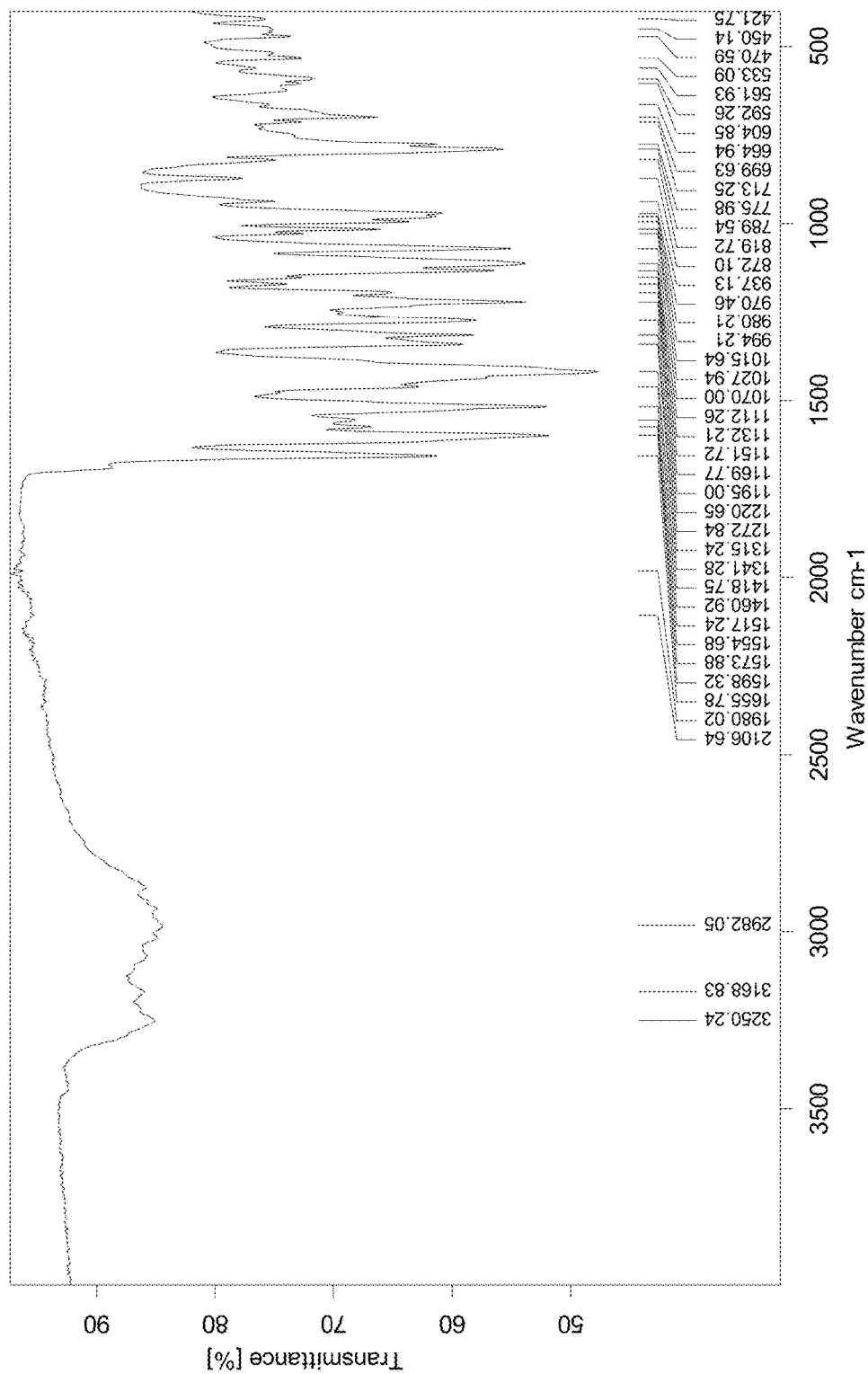
FIG. 35 depicts the IR spectrum for Form F of Compound 1.
Figure 36:
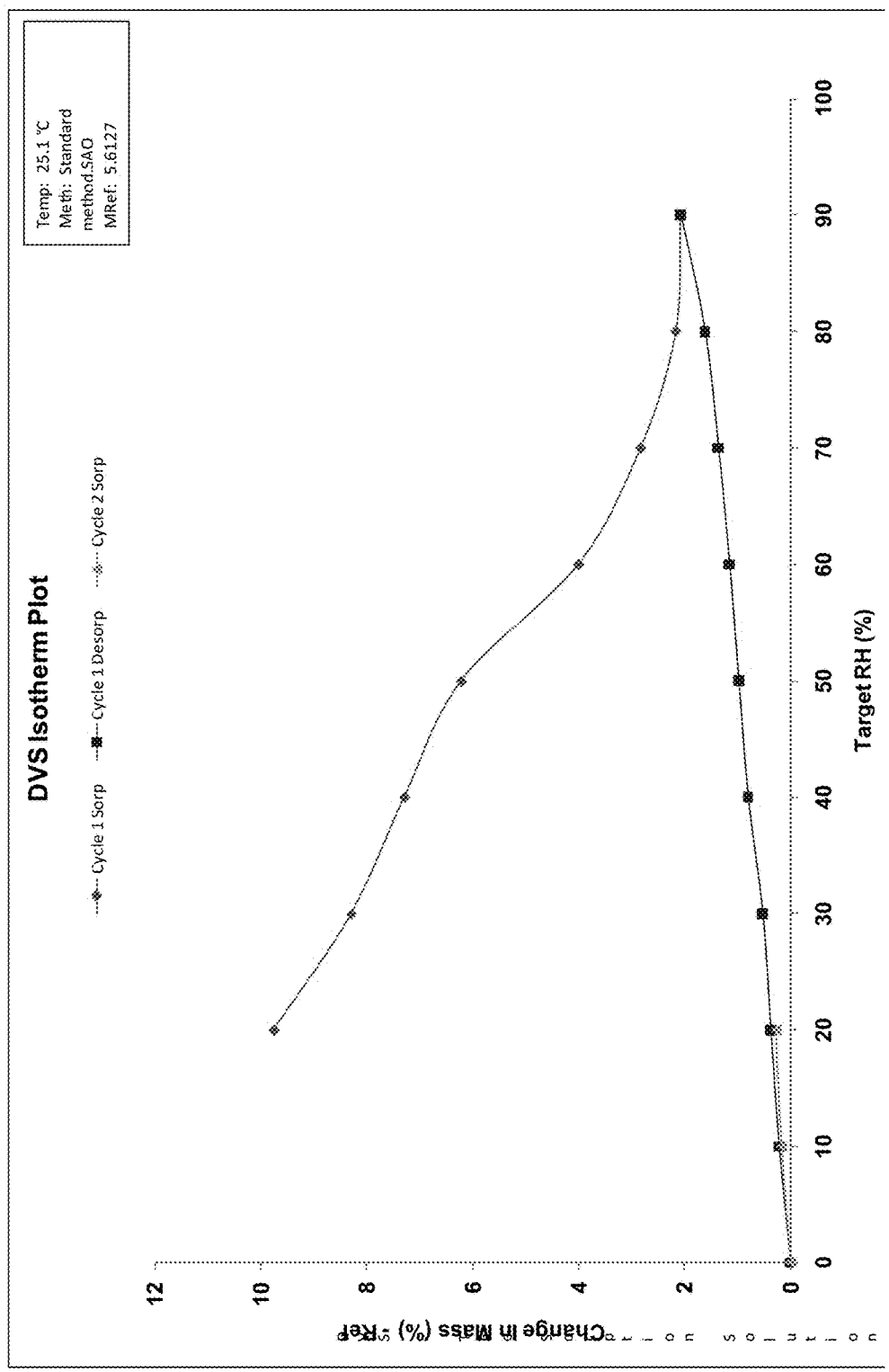
FIG. 36 depicts the DVS pattern for Form F of Compound 1.

According to one aspect, Form F of Compound 1 has a powder X-ray diffraction pattern substantially similar to that depicted in FIG. 32. According to another aspect, Form F of Compound 1 has a thermogravimetric analysis pattern substantially similar to that depicted in FIG. 33. Accordingly to yet another aspect, Form F of Compound 1 has a differential scanning calorimetry pattern substantially similar to that depicted in FIG. 34. According to a further embodiment, Form F of Compound 1 has a infrared spectrum substantially similar to that depicted in FIG. 35. According to another embodiment, Form F of Compound 1 has a dynamic vapour sorption pattern substantially similar to that depicted in FIG. 36. Form F of Compound 1 can be characterized by substantial similarity to two or more of these figures simultaneously.

In certain embodiments, the present invention provides Form G of Compound 1. According to another embodiment, Form G of Compound 1 is characterized by one or more peaks in its powder X-ray diffraction pattern selected from those at about 6.79, about 17.86, about 19.43, about 19.98 and about 22.35 degrees 2-theta. In some embodiments, Form G of Compound 1 is characterized by two or more peaks in its powder X-ray diffraction pattern selected from those at about 6.79, about 17.86, about 19.43, about 19.98 and about 22.35 degrees 2-theta. In further embodiments, Form G of Compound 1 is characterized by three or more peaks in its powder X-ray diffraction pattern selected from those at about 6.79, about 17.86, about 19.43, about 19.98 and about 22.35 degrees 2-theta. In particular embodiments, Form G of Compound 1 is characterized by substantially all of the peaks in its X-ray powder diffraction pattern selected from those at about 6.79, 6.89, 16.50, 17.86, 19.43, 19.98, 22.35, 23.77 and 24.06 degrees 2-theta. In an exemplary embodiment, Form G of Compound 1 is characterized by substantially all of the peaks in its X-ray powder diffraction pattern selected from those at about:

| °2-Theta |
|---|
| 3.70 |
| 4.38 |
| 6.79 |
| 6.89 |
| 8.60 |
| 9.85 |
| 12.28 |
| 13.48 |
| 14.52 |
| 15.35 |
| 16.08 |
| 16.50 |
| 17.16 |
| 17.86 |
| 18.67 |
| 19.43 |
| 19.98 |
| 20.66 |
| 21.06 |
| 21.56 |
| 22.35 |
| 23.77 |
| 24.06 |
| 25.03 |
| 26.06 |
| 26.22 |
| 26.79 |
| 27.56 |
| 28.07 |
| 28.74 |
| 29.18 |
| 29.59 |
| 30.08 |
| 30.43 |
| 31.29 |
| 32.36 |
| 32.68 |
| 33.49 |
| 34.40 |
| 34.82 |
| 35.27 |
| 36.01 |
| 36.40 |
| 37.02 |
| 38.03 |
| 38.48 |
| 39.37 |
| 39.94 |
| 41.00 |
| 41.97 |
| 42.64 |

| °2-Theta |
| --- |
| 43.69 |
| 44.91 |
| 45.35 |
| 46.20 |
| 47.43 |
| 48.53 |
| 48.75 |
| 49.48 |

Figure 39:
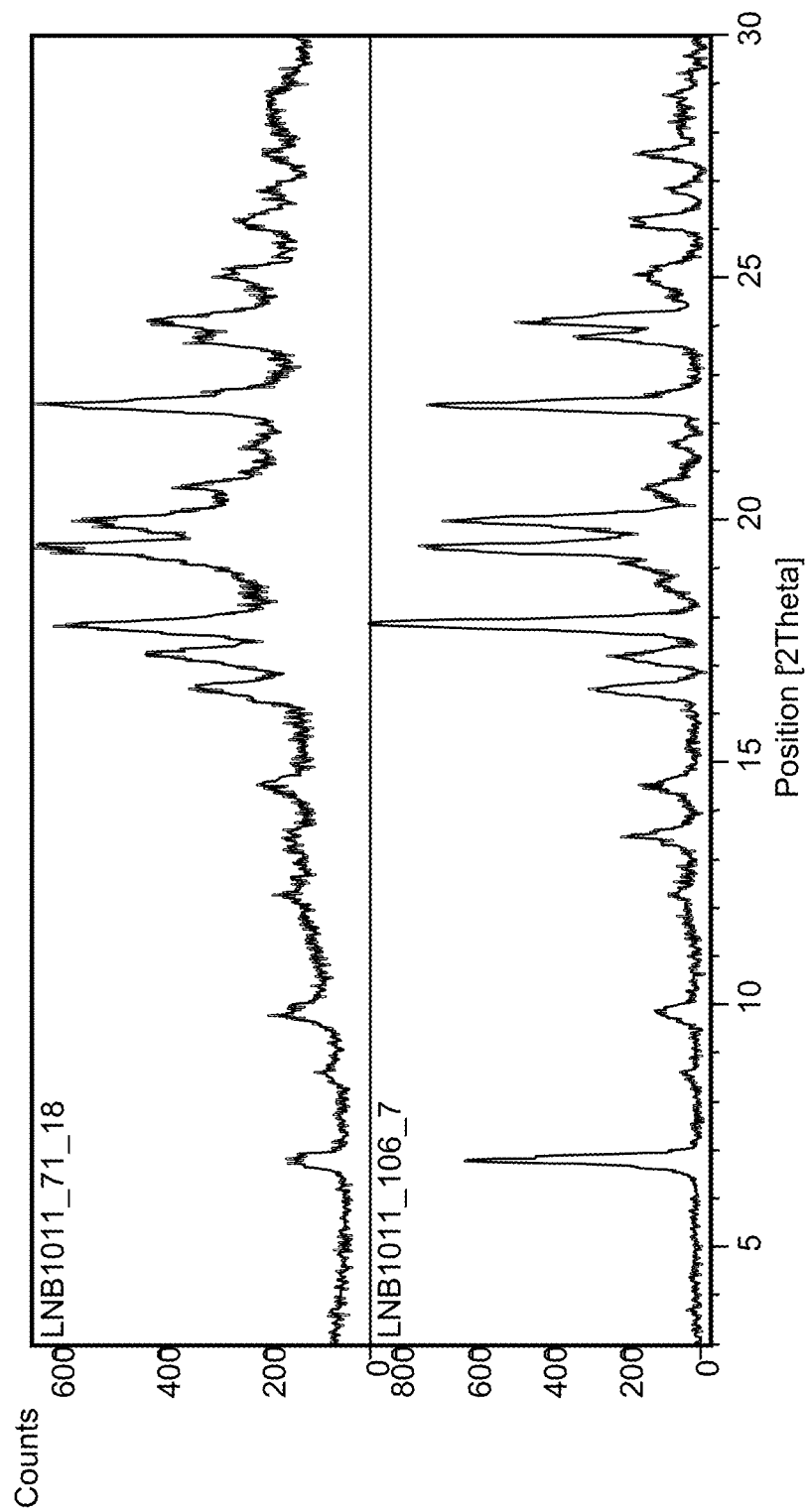
FIG. 39 depicts the XRPD pattern for Form C of Compound 1.
Figure 40A:
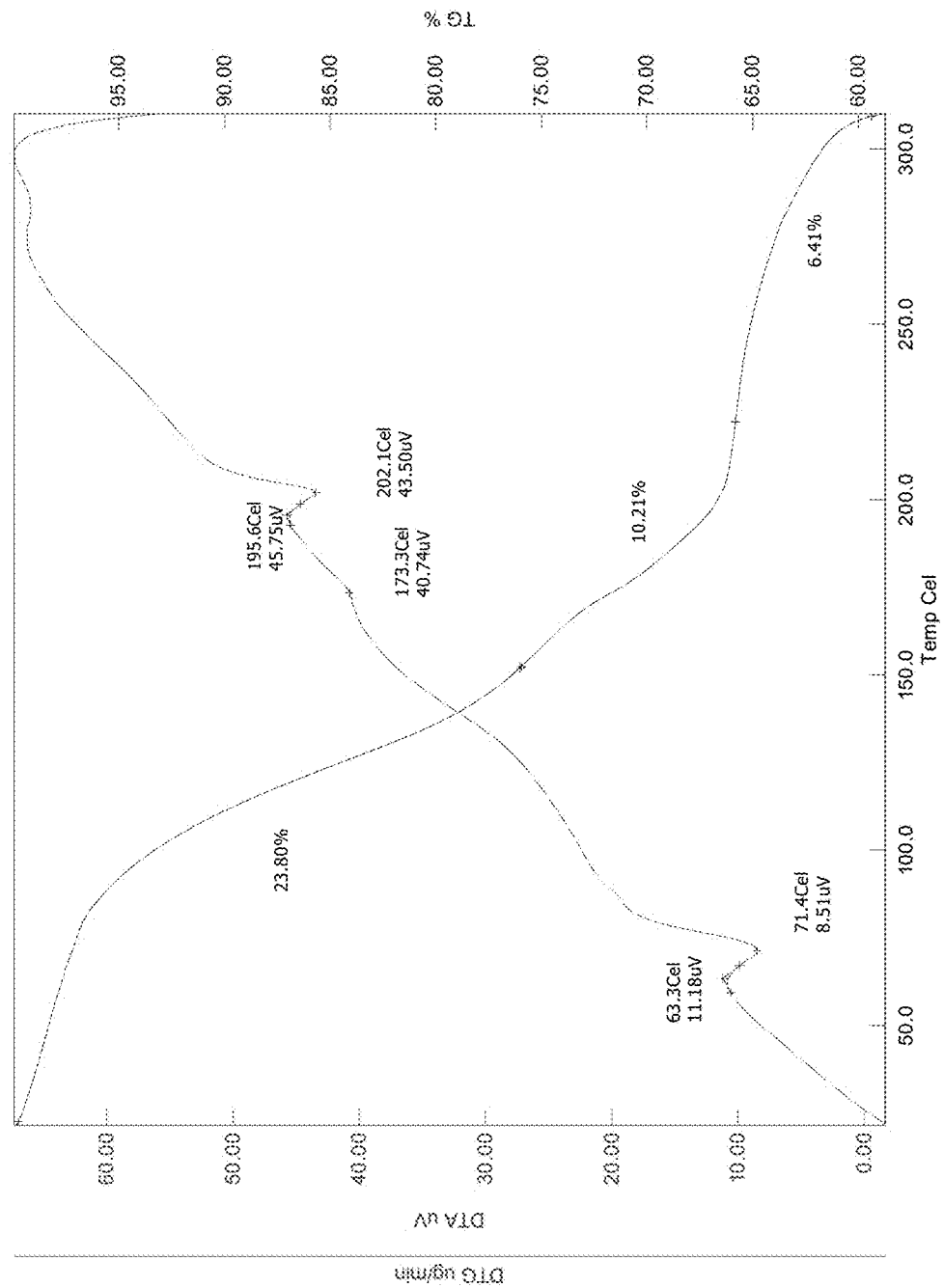
FIGS. 40A, 40B and 40C depict TGA/DTA patterns for Form G of Compound 1.
Figure 40B:
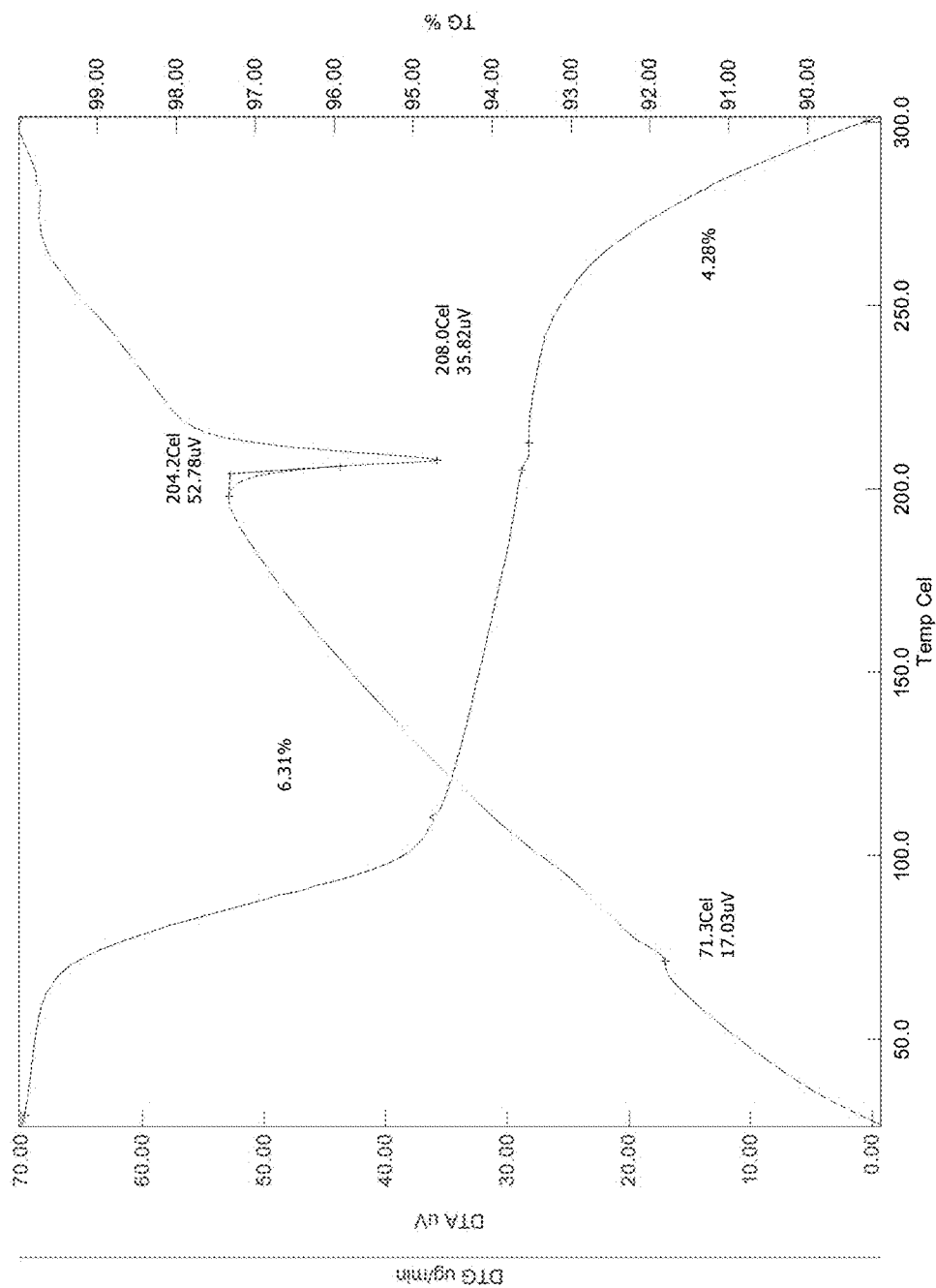
Figure 40C:
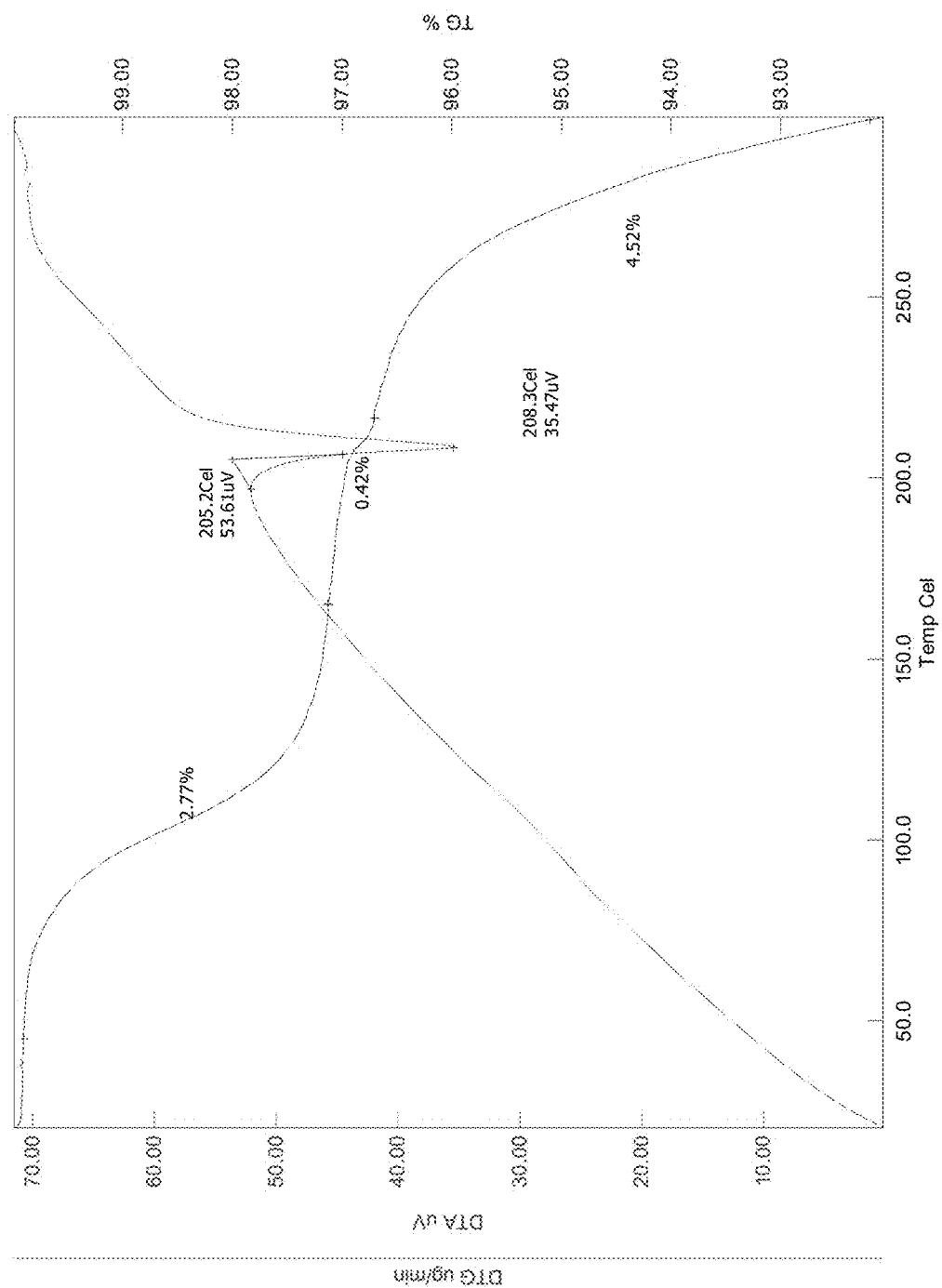
Figure 41:
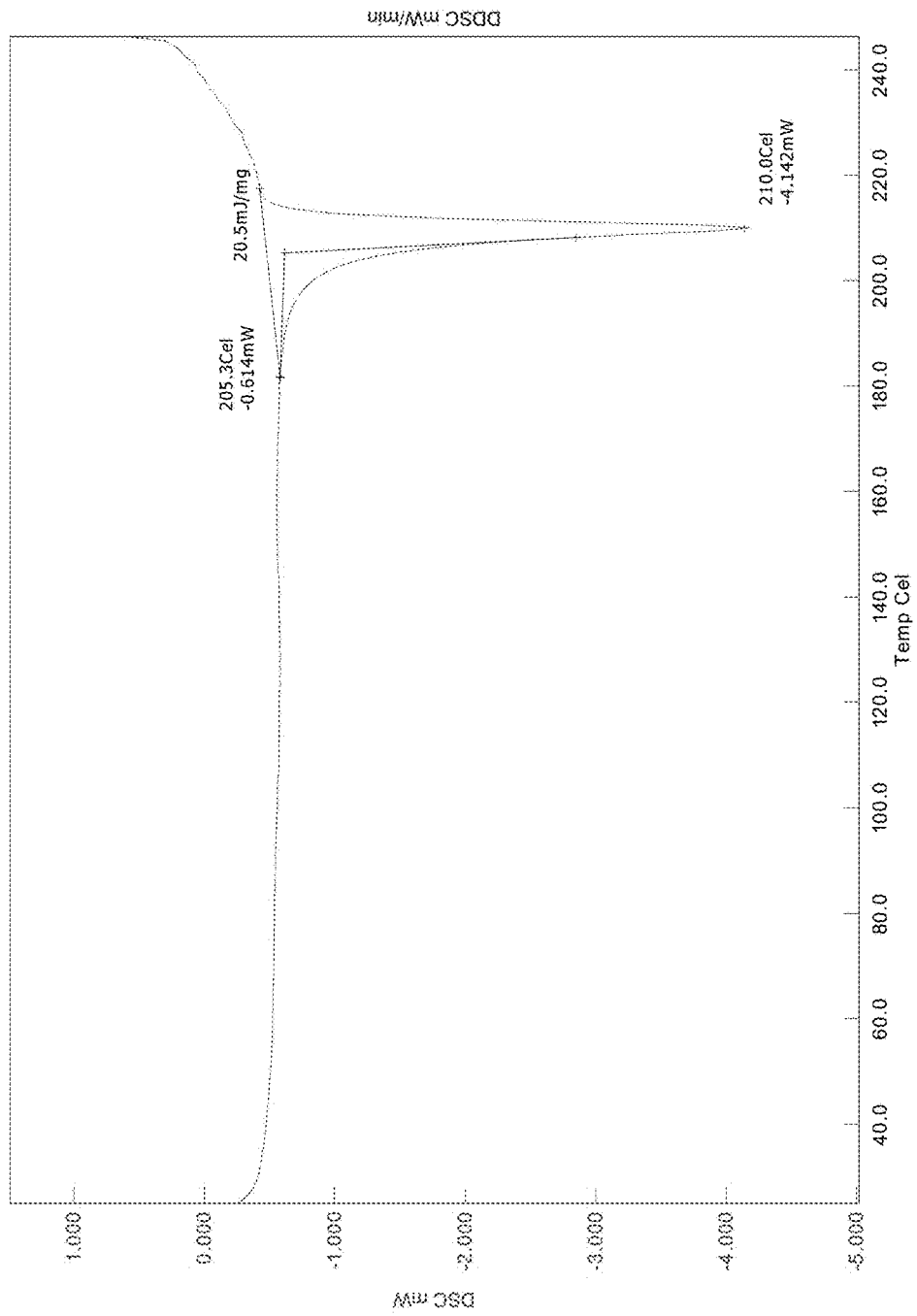
FIG. 41 depicts the DSC pattern for Form G of Compound 1.
Figure 42:
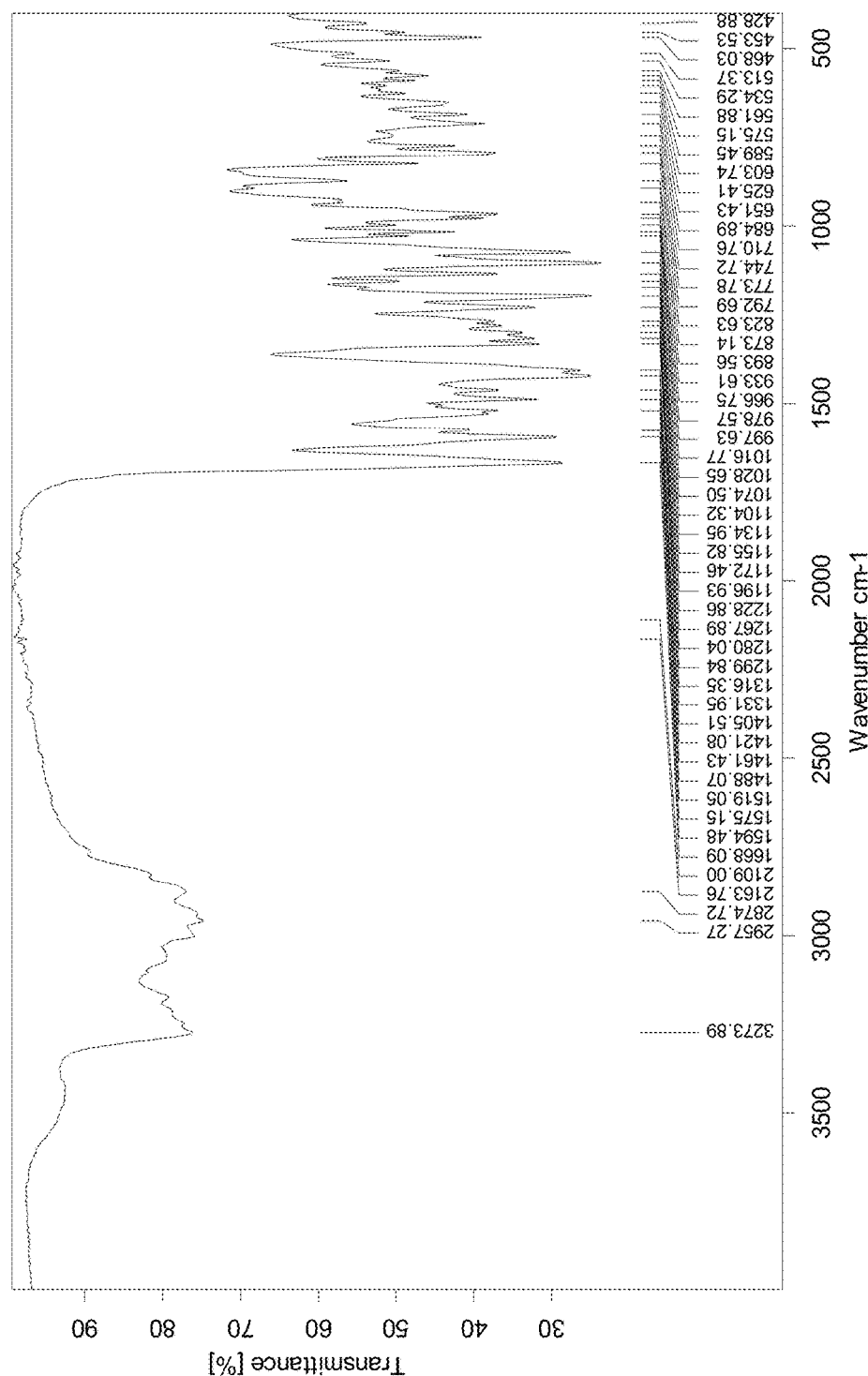
FIG. 42 depicts the IR spectrum for Form G of Compound 1.
Figure 43:
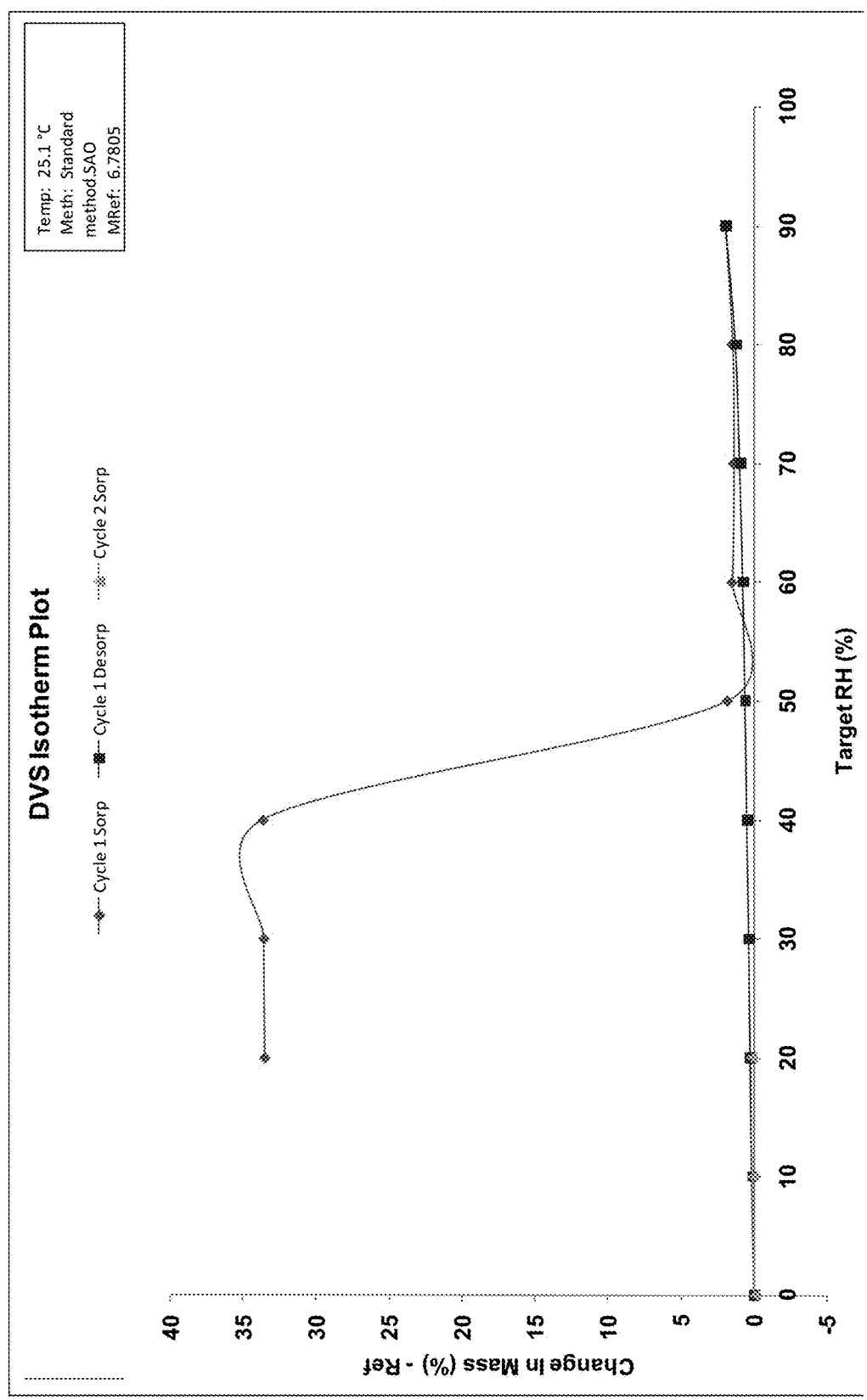
FIG. 43 depicts the DVS pattern for Form G of Compound 1.

According to one aspect, Form G of Compound 1 has a powder X-ray diffraction pattern substantially similar to that depicted in FIG. 39. According to another aspect, Form G of Compound 1 has a thermogravimetric analysis pattern substantially similar to that depicted in any of FIG. 40A, 40B or 40C. Accordingly to yet another aspect, Form G of Compound 1 has a differential scanning calorimetry pattern substantially similar to that depicted in FIG. 41. According to a further embodiment, Form G of Compound 1 has an infrared spectrum substantially similar to that depicted in FIG. 42. According to another embodiment, Form G of Compound 1 has a dynamic vapour sorption pattern substantially similar to that depicted in FIG. 43. Form G of Compound 1 can be characterized by substantial similarity to two or more of these figures simultaneously.

In certain embodiments, Compound 1 is a hydrated crystal form. It has been found that Compound 1 can exist in at least two distinct hydrated crystal forms, or polymorphs. In some embodiments, the present invention provides a hydrated polymorphic form of Compound 1 referred to herein as Form H. In some embodiments, the present invention provides a hydrated polymorphic form of Compound 1 referred to herein as Form I.

In certain embodiments, the present invention provides Form H of Compound 1. According one embodiment, Form H of Compound 1 is characterized by one or more peaks in its powder X-ray diffraction pattern selected from those at about 10.82, about 11.08, about 18.45, about 22.85 and about 25.06 degrees 2-theta. In some embodiments, Form H of Compound 1 is characterized by two or more peaks in its powder X-ray diffraction pattern selected from those at about 10.82, about 11.08, about 22.85 and about 25.06 degrees 2-theta. In certain embodiments, Form H of Compound 1 is characterized by three or more peaks in its powder X-ray diffraction pattern selected from those at about 10.82, about 11.08, about 18.45, about 22.85 and about 25.06 degrees 2-theta. In particular embodiments, Form H of Compound 1 is characterized by substantially all of the peaks in its X-ray powder diffraction pattern selected from those at about 10.14, 10.82, 11.08, 18.45, 22.85, 24.33, 25.06 and 26.54 degrees 2-theta. In an exemplary embodiment, Form H of Compound 1 is characterized by substantially all of the peaks in its X-ray powder diffraction pattern selected from those at about:

| °2-Theta |
| --- |
| 3.56 |
| 5.34 |
| 6.42 |
| 8.57 |
| 8.82 |
| 9.79 |
| 10.14 |
| 10.82 |

| °2-Theta |
| --- |
| 11.08 |
| 11.92 |
| 13.60 |
| 14.22 |
| 15.50 |
| 16.28 |
| 16.55 |
| 17.25 |
| 18.07 |
| 18.45 |
| 19.16 |
| 20.02 |
| 20.42 |
| 21.56 |
| 22.85 |
| 23.31 |
| 24.33 |
| 25.06 |
| 25.91 |
| 26.02 |
| 26.54 |
| 27.36 |
| 27.45 |
| 27.79 |
| 28.31 |
| 29.15 |
| 29.45 |

Figure 46:
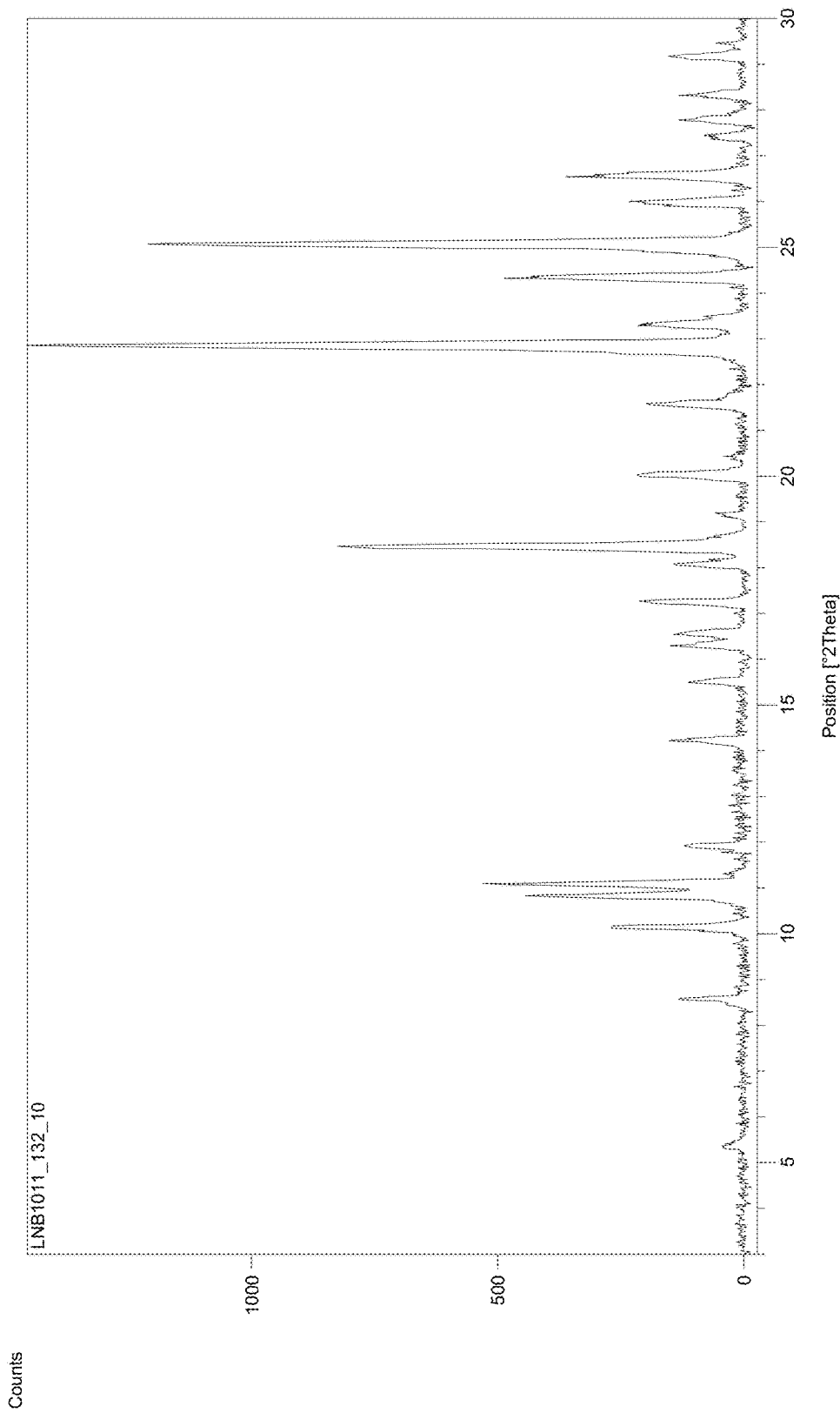
FIG. 46 depicts the XRPD pattern for Form H of Compound 1.
Figure 47:
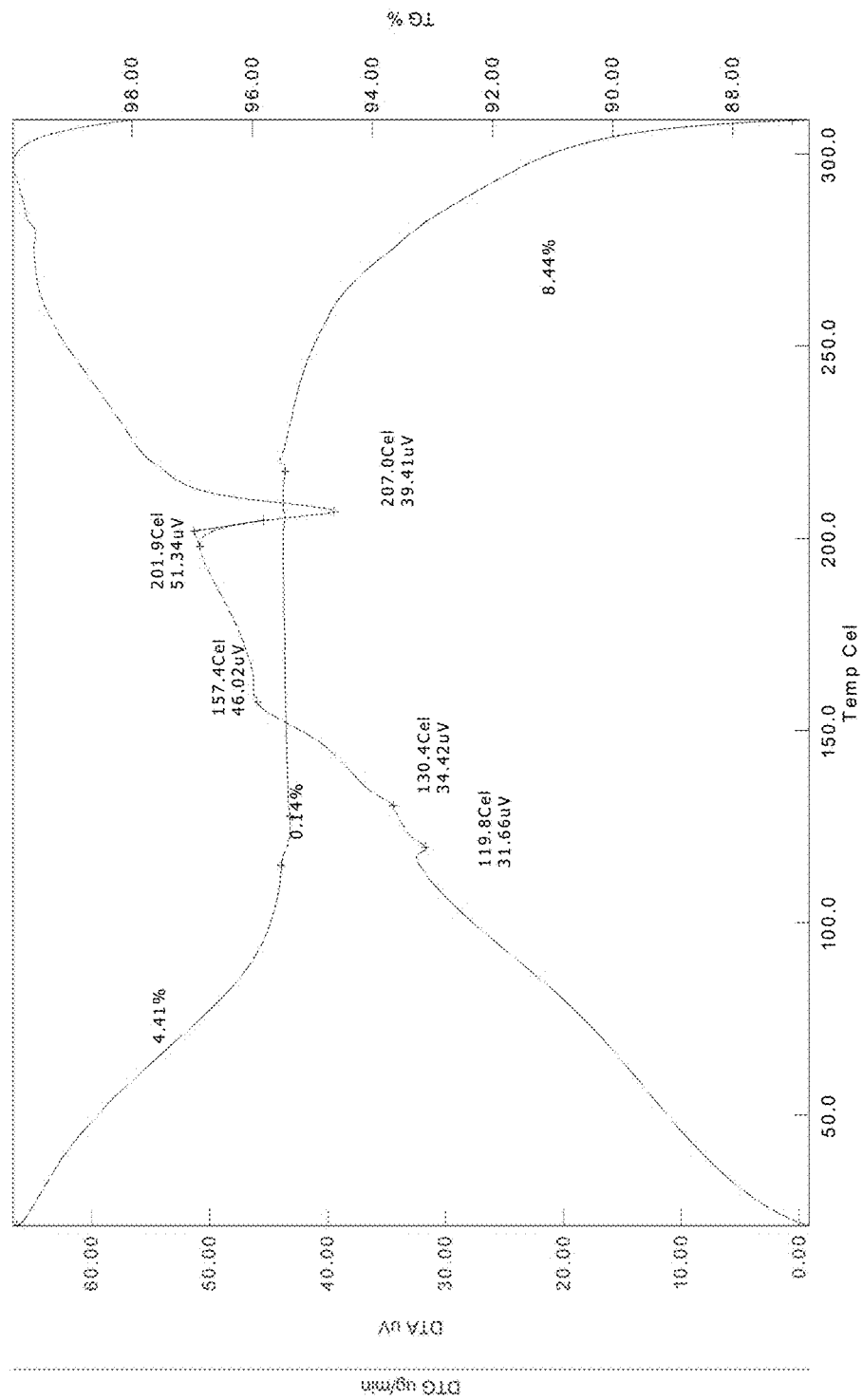
FIG. 47 depicts the TGA/DTA pattern for Form H of Compound 1.
Figure 49:
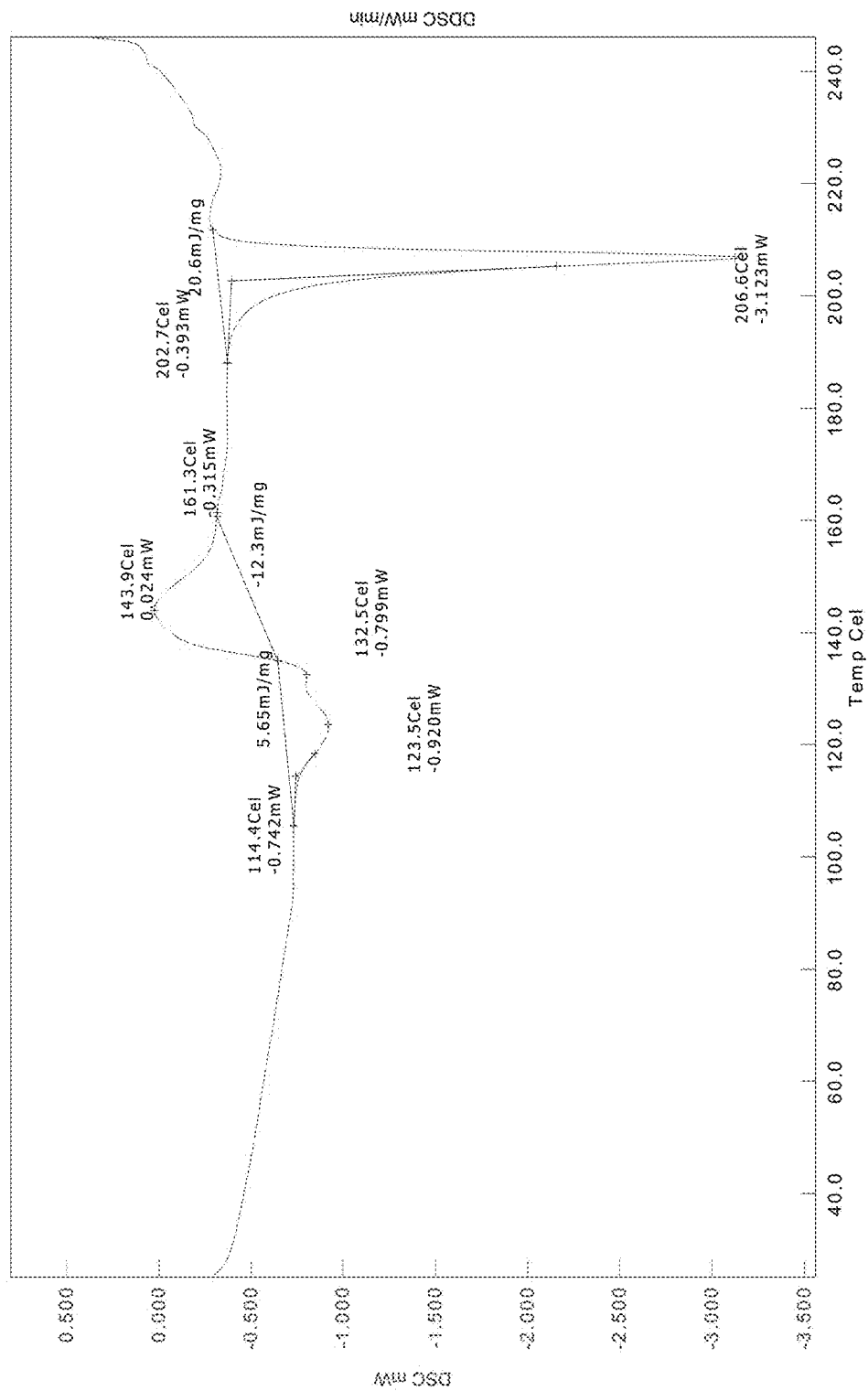
FIG. 49 depicts the DSC pattern for Form H of Compound 1.

According to one aspect, Form H of Compound 1 has a powder X-ray diffraction pattern substantially similar to that depicted in FIG. 46. According to another aspect, Form H of Compound 1 has a thermogravimetric analysis pattern substantially similar to that depicted in FIG. 47. Accordingly to yet another aspect, Form H of Compound 1 has a differential scanning calorimetry pattern substantially similar to that depicted in FIG. 49. In some embodiments, Form H of Compound 1 has a thermogravimetric analysis pattern substantially similar to that depicted in FIG. 50 or FIG. 51. Form H of Compound 1 can be characterized by substantial similarity to two or more of these figures simultaneously.

In certain embodiments, the present invention provides Form I of Compound 1. According to one embodiment, Form I of Compound 1 is characterized by one or more peaks in its powder X-ray diffraction pattern selected from those at about 6.13, about 12.22, about 15.91, about 18.35, about 18.88, and about 21.90 degrees 2-theta. In some embodiments, Form I of Compound 1 is characterized by two or more peaks in its powder X-ray diffraction pattern selected from those at about 6.13, about 12.22, about 15.91, about 18.35, about 18.88, and about 21.90 degrees 2-theta. In some embodiments, Form I of Compound 1 is characterized by three or more peaks in its powder X-ray diffraction pattern selected from those at about 6.13, about 12.22, about 15.91, about 18.35, about 18.88, and about 21.90 degrees 2-theta. In some embodiments, Form I of Compound 1 is characterized by four or more peaks in its powder X-ray diffraction pattern selected from those at about 6.13, about 12.22, about 15.91, about 18.35, about 18.88, and about 21.90 degrees 2-theta. In some embodiments, Form I of Compound 1 is characterized by substantially all of the peaks in its powder X-ray diffraction pattern selected from those at about 6.13, about 12.22, about 15.91, about 18.35, about 18.88, and about 21.90 degrees 2-theta. In some embodiments, Form I of Compound 1 is characterized by substantially all of the peaks selected from those at about:

| °2-Theta |
| --- |
| 5.39 |
| 6.13 |
| 7.65 |
| 9.33 |
| 10.18 |
| 12.22 |
| 12.72 |
| 12.98 |
| 14.56 |
| 15.08 |
| 15.31 |
| 15.91 |
| 16.47 |
| 18.35 |
| 18.88 |
| 19.65 |
| 20.36 |
| 21.16 |
| 21.90 |
| 22.64 |
| 23.26 |
| 23.75 |
| 24.55 |
| 24.95 |
| 25.78 |
| 27.95 |
| 28.92 |
| 29.47 |

Figure 52:
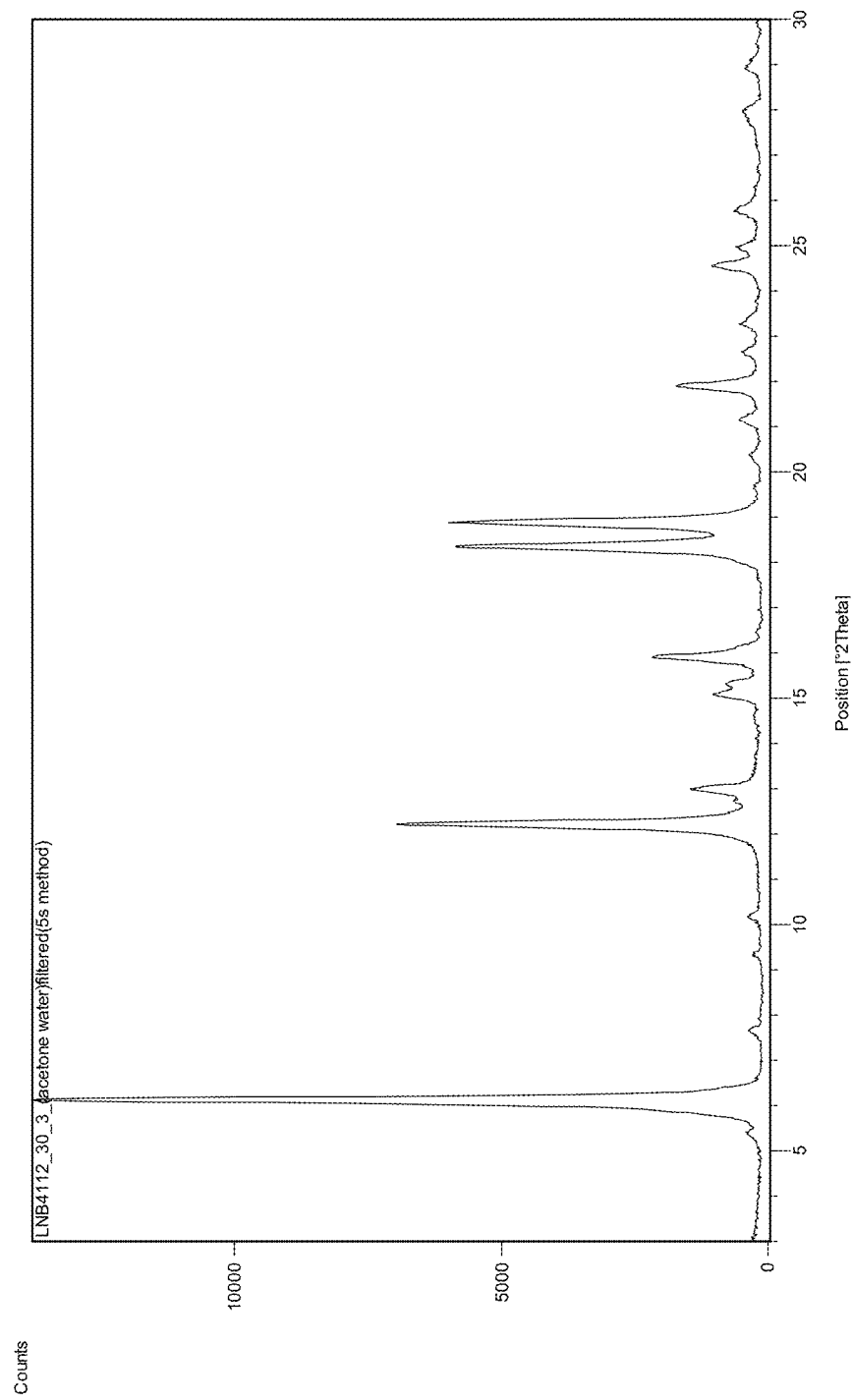
FIG. 52 depicts the XRPD for Form I of Compound 1.

According to one aspect, Form I of Compound 1 has a X-ray powder diffraction pattern substantially similar to that depicted in FIG. 52. In some embodiments, Form I of Compound 1 has an infrared spectrum substantially similar to that depicted in FIG. 53. In some embodiments, Form I of Compound 1 has a $^1$H NMR spectrum substantially similar to that depicted in FIG. 54. According to another aspect, Form I of Compound 1 has a thermogravimetric analysis pattern substantially similar to that depicted in FIG. 55 or FIG. 56. Accordingly to yet another aspect, Form I of Compound 1 has a differential scanning calorimetry pattern substantially similar to that depicted in FIG. 57. In some embodiments, Form I of Compound 1 has an dynamic vapour sorption substantially similar to that depicted in FIG. 58. Form I of Compound 1 can be characterized by substantial similarity to two or more of these figures simultaneously.

It will be appreciated that any of the above-described polymorph forms can be characterized, for example, by reference to any of the peaks in their respective X-ray diffraction patterns. Accordingly, in some embodiments, a polymorph described herein is characterized by one, two, three, four, five, six, seven, eight, nine, ten, eleven, twelve, thirteen, fourteen, fifteen, sixteen, seventeen, eighteen, nineteen, twenty or more XRPD peaks (°2θ). According to another embodiment, the present invention provides compound 1 as an amorphous solid. Amorphous solids are well known to one of ordinary skill in the art and are typically prepared by such methods as lyophilization, melting, and precipitation from supercritical fluid, among others.
General Methods of Providing Compound 1:

Compound 1 is prepared according to the methods described in detail in the '061 application, the entirety of which is hereby incorporated herein by reference. The various solid forms of Compound 1 can be prepared by dissolving compound 1 in various suitable solvents and then causing Compound 1 to return to the solid phase. Specific combinations of solvents and conditions under which Compound 1 return to the solid phase are discussed in greater detail in the Examples.

A suitable solvent may solubilize Compound 1, either partially or completely. Examples of suitable solvents useful in the present invention are a protic solvent, a polar aprotic solvent, or mixtures thereof. In certain embodiments, suitable solvents include an ether, an ester, an alcohol, a ketone, or a mixture thereof. In certain embodiments, the suitable solvent is methanol, ethanol, isopropanol, or acetone wherein said solvent is anhydrous or in combination with water, methyl tert-butyl ether (MTBE) or heptane. In other embodiments, suitable solvents include tetrahydrofuran, 1,4-dioxane, dimethylformamide, dimethylsulfoxide, glyme, diglyme, methyl ethyl ketone, N-methyl-2-pyrrolidone, methyl t-butyl butyl ether, t-butanol, n-butanol, and acetonitrile. In another embodiment, the suitable solvent is anhydrous ethanol. In some embodiments, the suitable solvent is MTBE.

According to another embodiment, the present invention provides a method for preparing a solid form of Compound 1, comprising the steps of dissolving Compound 1 with a suitable solvent and optionally heating to form a solution thereof; and isolating Compound 1.

As described generally above, Compound 1 is dissolved in a suitable solvent, optionally with heating. In certain embodiments Compound 1 is dissolved at about 50 to about 60° C. In other embodiments, Compound 1 is dissolved at about 50 to about 55° C. In still other embodiments, Compound 1 is dissolved at the boiling temperature of the solvent. In other embodiments, Compound 1 is dissolved without heating (e.g., at ambient temperature, approximately 20-25° C.).

In certain embodiments, Compound 1 precipitates from the mixture. In another embodiment, Compound 1 crystallizes from the mixture. In other embodiments, Compound 1 crystallizes from solution following seeding of the solution (i.e., adding crystals of Compound 1 to the solution).

Crystalline Compound 1 can precipitate out of the reaction mixture, or be generated by removal of part or all of the solvent through methods such as evaporation, distillation, filtration (e.g., nanofiltration, ultrafiltration), reverse osmosis, absorption and reaction, by adding an anti-solvent (e.g., water, MTBE and/or heptane), by cooling (e.g., crash cooling) or by different combinations of these methods.

As described generally above, Compound 1 is optionally isolated. It will be appreciated that Compound 1 may be isolated by any suitable physical means known to one of ordinary skill in the art. In certain embodiments, precipitated solid Compound 1 is separated from the supernatant by filtration. In other embodiments, precipitated solid Compound 1 is separated from the supernatant by decanting the supernatant.

In certain embodiments, precipitated solid Compound 1 is separated from the supernatant by filtration.

In certain embodiments, isolated Compound 1 is dried in air. In other embodiments isolated Compound 1 is dried under reduced pressure, optionally at elevated temperature.
Uses, Formulation and Administration
Pharmaceutically Acceptable Compositions According to another embodiment, the invention provides a composition comprising Compound 1 and a pharmaceutically acceptable carrier, adjuvant, or vehicle. The amount of Compound 1 in compositions of this invention is such that it is effective to measurably inhibit a protein kinase, particularly an EGFR kinase, or a mutant thereof, in a biological sample or in a patient. In certain embodiments, a composition of this invention is formulated for administration to a patient in need of such composition. In some embodiments, a composition of this invention is formulated for oral administration to a patient.

The term "patient", as used herein, means an animal, preferably a mammal, and most preferably a human.

The term "pharmaceutically acceptable carrier, adjuvant, or vehicle" refers to a non-toxic carrier, adjuvant, or vehicle that does not destroy the pharmacological activity of the compound with which it is formulated. Pharmaceutically acceptable carriers, adjuvants or vehicles that may be used in the compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, Vitamin E polyethylene glycol succinate (d-alpha tocopheryl polyethylene glycol 1000 succinate), sodium carboxymethylcellulose, polyacrylates, waxes, polyethylene-polyoxypropylene-block polymers, and wool fat.

Compositions of the present invention may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously. Sterile injectable forms of the compositions of this invention may be an aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium.

For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

Pharmaceutically acceptable compositions of this invention may be orally administered in any orally acceptable dosage form including, but not limited to, capsules, tablets, aqueous and non-aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is typically combined with emulsifying and suspending agents. If desired, certain sweetening, flavoring or coloring agents may also be added.

Alternatively, pharmaceutically acceptable compositions of this invention may be administered in the form of suppositories for rectal administration. These can be prepared by mixing the anent with a suitable non-irritating excipient that is solid at room temperature but liquid at rectal temperature and therefore will melt in the rectum to release the drug. Such materials include cocoa butter, beeswax and polyethylene glycols.

Pharmaceutically acceptable compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, provided pharmaceutically acceptable compositions may be formulated in a suitable ointment containing the active component suspended or dissolved in one or more carriers. Carriers for topical administration of Compound 1 include, but are not limited to, mineral oil, liquid petrolatum white petrolatum propylene glycol, polyoxyethylene, polyoxypropylene compound, emulsifying wax and water. Alternatively, provided pharmaceutically acceptable compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, provided pharmaceutically acceptable compositions may be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutically acceptable compositions may be formulated in an ointment such as petrolatum.

Pharmaceutically acceptable compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

In some embodiments, pharmaceutically acceptable compositions of this invention are formulated for oral administration.

The amount of Compound 1 that may be combined, with the carrier materials to produce a composition in a single dosage form will vary depending upon the host treated, the particular mode of administration. In certain embodiments, provided compositions are formulated so that a dosage of between 0.01-100 mg/kg body weight/day of Compound 1 can be administered to a patient receiving these compositions.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated.

Uses of Compounds and Pharmaceutically Acceptable Compositions

Compound 1 and compositions described herein are generally useful for the inhibition of protein kinase activity of one or more enzymes. Examples of kinases that are inhibited by Compound 1 and compositions described herein and against which the methods described herein are useful include EGFR kinase or a mutant thereof. It has been found that Compound 1 is a selective inhibitor of at least one mutation of EGFR, as compared to wild-type ("WT") EGFR. In certain, embodiments, an at least one mutation of EGFR is T790M. In certain embodiments, the at least one mutation of EGFR is a deletion mutation. In some embodiments, the at least one mutation of EGFR is an activating mutation. In certain embodiments, Compound 1 selectively inhibits at least one resistant mutation and at least one activating mutation as compared to WT EGFR. In some embodiments, Compound 1 selectively inhibits at least one deletion mutation and/or at least one point mutation, and is sparing as to WT EGFR inhibition.

A mutation of EGFR can be selected from T790M (resistant or oncogenic), L858R (activating), delE746-A750 (activating), G719S (activating), or a combination thereof.

As used herein, the term "selectively inhibits," as used in comparison to inhibition of WT EGFR, means that Compound 1 inhibits at least one mutation of EGFR (i.e., at least one deletion mutation, at least one activating mutation, at least one resistant mutation, or a combination of at least one deletion mutation and at least one point mutation) in at least one assay described herein (e.g., biochemical or cellular). In some embodiments, the term "selectively inhibits," as used in comparison to WT EGFR inhibition means that Compound 1 is at least 50 times more potent, at least 45 times, at least 40, at least 35, at least 30, at least 25, or at least 20 times more potent as an inhibitor of at least one mutation of EGFR, as defined and described herein, as compared to WT EGFR.

As used herein, the term "sparing as to WT EGFR" means that a selective inhibitor of at least one mutation of EGFR, as defined and described above and herein, inhibits EGFR at the upper limit of detection of at least one assay, such as those described in the '061 application (e.g., biochemical or cellular as described in detail in Examples 56-58). In vitro assays include assays that determine inhibition of the phosphorylation activity and/or the subsequent functional consequences, or ATPase activity of activated EGFR (WT or mutant). Alternate in vitro assays quantitate the ability of the inhibitor to bind to EGFR (WT or mutant). Inhibitor binding may be measured by radiolabeling the inhibitor prior to binding, isolating the inhibitor/EGFR (WT or mutant) complex and determining the amount of radiolabel bound. Alternatively, inhibitor binding may be determined by running a competition experiment where new inhibitors are incubated with EGFR (WT or mutant) bound to known radioligands. In some embodiments, the term "sparing as to WT EGFR" means that Compound 1 inhibits WT EGFR with an $IC_{50}$ of at least 10 µM, at least 9 µM, at least 8 µM, at least 7 µM, at least 6 µM, at least 5 µM, at least 3 µM, at least 2 µM, or at least 1 µM.

In certain embodiments, Compound 1 selectively inhibits (a) at least one activating mutation; and (b) T790M; and (c) is sparing as to WT. In some embodiments, an at least one activating mutation is a deletion mutation. In some embodiments, an at least one activating mutation is a point mutation. In some embodiments, an activating mutation is delE746-A750. In some embodiments, an activating mutation is L858R. In some embodiments, an activating mutation is G719S.

In some embodiments, the at least one mutation of EGFR is L858R and/or T790M.

Without wishing to be bound by any particular theory, it is believed that administration of Compound 1 to a patient having at least one activating mutation may preempt formation of the T790M resistance mutation. Thus, in certain embodiments, the present invention provides a method for inhibiting an activating mutation in a patient comprising administering to the patient Compound 1 or composition thereof, as described herein.

One of ordinary skill in the art will appreciate that certain patients have an oncogenic form of the T790M mutation, i.e., the T790M mutation is present prior to administrating any EGFR kinase inhibitor to a patient and is therefore oncogenic. Accordingly, in some embodiments, the present invention provides a method for inhibiting oncogenic T790M in a patient comprising administering to the patient a provided compound or composition thereof, as described herein.

In certain embodiments, the amount of Compound 1 in a composition is effective to measurably inhibit at least one mutant of EGFR selectively as compared to WT EGFR and other protein kinases (e.g., ErbB2, ErbB4, a TEC-kinase, and/or JAK3), in a biological sample or in a patient.

As used herein, the terms "treatment," "treat," and "treating" refer to reversing, alleviating, delaying the onset of, or inhibiting the progress of a disease or disorder, or one or more symptoms thereof, as described herein. In some embodiments, treatment may be administered after one or more symptoms have developed. In other embodiments, treatment may be administered in the absence of symptoms. For example, treatment may be administered to a susceptible individual prior to the onset of symptoms (e.g., in light of a history of symptoms and/or in light of genetic or other susceptibility factors). Treatment may also be continued after symptoms have resolved, for example to prevent or delay their recurrence.

Compound 1 is an inhibitor of at least one mutant of EGFR and is therefore useful for treating one or more disorders associated with activity of one of more EGFR mutants (e.g., a deletion mutation, an activating mutation, a resistant mutation, or combination thereof). Thus, in certain embodiments, the present invention provides a method for treating a mutant EGFR-mediated disorder comprising the step of administering to a patient in need thereof. Compound 1, or pharmaceutically acceptable composition thereof.

As used herein, the term "mutant EGFR-mediated" disorders or conditions as used herein means any disease or other deleterious condition in which at least one mutant of EGFR is known to play a role. In certain embodiments, an at least one mutant of EGFR is T790M. In some embodiments, the at least one mutant of EGFR is a deletion mutation. In certain embodiments, the at least one mutant of EGFR is an activating mutation. In some embodiments, the at least one mutant of EGFR is L858R and/or T790M. In certain embodiments, Compound 1 selectively inhibits (a) at least one activating mutation, (b) T790M, and (c) is sparing as to WT. In some embodiments, an at least one activating mutation is a deletion mutation. In some embodiments, an at least one activating mutation is a point mutation. In some embodiments, an activating mutation is delE746-A750. In some embodiments, an activating mutation is L858R. In some embodiments, an activating mutation is G719S.

Accordingly, another embodiment of the present invention relates to treating or lessening the severity of one or more diseases in which at least one mutant of EGFR is known to play a role. Specifically, the present invention relates to a method of treating or lessening the severity of a disease or condition selected from a proliferative disorder, wherein said method comprises administering to a patient in need thereof a compound or composition according to the present invention.

In some embodiments, the present invention provides a method for treating or lessening the severity of one or more disorders selected from a cancer. In some embodiments, the cancer is associated with a solid tumor. In certain embodiments, the cancer is breast cancer, glioblastoma, lung cancer, cancer of the head and neck, colorectal cancer, bladder cancer, or non-small cell lung cancer. In some embodiments, the present invention provides a method for treating or lessening the severity of one or more disorders selected from squamous cell carcinoma, salivary gland carcinoma, ovarian carcinoma, or pancreatic cancer.

In certain embodiments, the present invention provides a method for treating or lessening the severity of neurofibromatosis type I (NF1), neurofibromatosis type II (NF2) Schwann cell neoplasms (e.g. MPNST's), or Schwannomas.

Compound 1 and compositions thereof, according to the method of the present invention, may be administered using any amount and any route of administration effective for treating or lessening the severity of a cancer. The exact amount required will vary from subject to subject, depending on the species, age, and general condition of the subject, the severity of the infection, the particular agent, its mode of administration, and the like. Compound 1 is preferably formulated in dosage unit form for case of administration and uniformity of dosage. The expression "dosage unit form" as used herein refers to a physically discrete unit of agent appropriate for the patient to be treated. It will be understood, however, that the total daily usage of the compounds and compositions of the present invention will be decided by the attending physician within the scope of sound medical judgment. The specific effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors well known in the medical arts.

Pharmaceutically acceptable compositions of this invention can be administered to humans and other animals orally, rectally, parenterally, intracisternally, intravaginally, intraperitoneally, topically (as by powders, ointments, or drops), bucally, as an oral or nasal spray, or the like, depending on the severity of the infection being treated. In certain embodiments, Compound 1 may be administered orally or parenterally at dosage levels of about 0.01 mg/kg to about 50 mg/kg and preferably from about 0.5 mg/kg to about 25 mg/kg, of subject body weight per day, one or more times a day, to obtain the desired therapeutic effect.

Liquid dosage forms for oral administration include, but are not limited to, pharmaceutically acceptable emulsions, microemulsions, solutions, suspensions, syrups and elixirs. In addition to Compound 1, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, polyethylene glycol, (e.g., PEG 200, PEG 400, PEG 1000, PEG 2000), propylene glycol, 1,3-butylene glycol, dimethylformamide, oils (in particular, cottonseed, groundnut, corn, germ, olive, castor, and sesame oils), glycerol, tetrahydrofurfuryl alcohol, Vitamin E polyethylene glycol succinate (d-alpha tocopheryl polyethylene glycol 1000 succinate), polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents. The liquid forms above can also be filled into a soft or hard capsule to form a solid dosage form. Suitable capsules can be formed from, for example, gelatin, starch and cellulose derivatives (e.g., hydroxycellulose, hydropropylmethylcellulose).

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

Injectable formulations can be sterilized, for example, by filtration through a bacterial-retaining filler, or by incorporating sterilizing agents in the form of sterile solid compositions which can be dissolved or dispersed in sterile water or other sterile injectable medium prior to use.

In order to prolong the effect of Compound 1 of the present invention, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly(orthoesters) and poly(anhydrides). Depot injectable formulations are also prepared by entrapping the compound in liposomes or microemulsions that are compatible with body tissues.

Compositions for rectal or vaginal administration are preferably suppositories which can be prepared by mixing Compound 1 of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, Compound 1 is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled capsules using such excipients as lactose or milk sugar as well as high molecular weight polyethylene glycols and the like.

Compound 1 can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of Compound 1 include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, and eye drops are also contemplated as being within the scope of this invention. Additionally, the present invention contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

According to another embodiment, the invention relates to a method of inhibiting at least one mutant of EGFR (e.g., a deletion mutation, an activating mutation, a resistant mutations, or combination thereof) activity in a biological sample comprising the step of contacting said biological sample with Compound 1, or a composition comprising the compound. In certain embodiments, the invention relates to a method of irreversibly inhibiting at least one mutant of EGFR (e.g., a deletion mutation, an activating mutation, a resistant mutation, or combination thereof) activity in a biological sample comprising the step of contacting the biological sample with Compound 1, or a composition comprising the compound.

In certain embodiments, Compound 1 selectively inhibits in a biological sample (a) at least one activating mutation, (b) T790M, and (c) is sparing as to WT. In some embodiments, an at least one activating mutation is a deletion mutation. In some embodiments, an at least one activating mutation is a point mutation. In some embodiments, an activating mutation is delE746-A750. In some embodiments, an activating mutation is L858R. In some embodiments, an activating mutation is G719S.

The term "biological sample", as used herein, includes, without limitation, cell cultures or extracts thereof; biopsied material obtained from a mammal or extracts thereof; and blood, saliva, urine, feces, semen, tears, or other body fluids or extracts thereof.

Inhibition of at least one mutant of EGFR (e.g., a deletion mutation, an activating mutation, a resistant mutation, or combination thereof) activity in a biological sample is useful for a variety of purposes that are known to one of skill in the art. Examples of such purposes include, but are not limited to, blood transfusion, organ transplantation, biological specimen storage, and biological assays.

Another embodiment of the present invention relates to a method of inhibiting at least one mutant of EGFR (e.g., a deletion mutation, an activating mutation, a resistant mutation, or combination thereof) activity in a patient comprising the step of administering to the patient Compound 1 or a composition comprising the compound. In certain embodiments, the present invention provides a method for inhibiting (a) at least one activating mutation, and (b) T790M in a patient, and (c) is sparing as to WT, wherein the method comprises administering to the patient Compound 1 or composition thereof. In some embodiments, an at least one activating mutation is a deletion mutation. In some embodiments, an at least one activating mutation is a point mutation. In some embodiments, the present invention provides a method for inhibiting at least one mutant of EGFR in a patient, wherein an activating mutation is delE746-A750. In some embodiments, the present invention provides a method for inhibiting at least one mutant of EGFR in a patient, wherein an activating mutation is L858R. In some embodiments, the present invention provides a method for inhibiting at least one mutant of EGFR in a patient, wherein an activating mutation is G719S.

According to another embodiment, the invention relates to a method of inhibiting at least one mutant of EGFR (e.g., a deletion mutation, an activating mutation, a resistant mutation, or combination thereof) activity in a patient comprising the step of administering to the patient Compound 1 or a composition comprising the compound. According to certain embodiments, the invention relates to a method of irreversibly inhibiting at least one mutant of EGFR activity (e.g., a deletion mutation, an activating mutation, a resistant mutation, or combination thereof) in a patient comprising the step of administering to said patient Compound 1 or a composition comprising the compound. In certain embodiments, the present invention provides a method for irreversibly inhibiting (a) at least one activating mutation, and (b) T790M in a patient, and (c) is sparing as to WT, wherein said method comprises administering to the patient Compound 1 or composition thereof. In some embodiments, an irreversibly inhibited at least one activating mutation is a deletion mutation. In some embodiments, an irreversibly inhibited at least one activating mutation is a point mutation. In some embodiments, the present invention provides a method for irreversibly inhibiting at least one mutant of EGFR in a patient, wherein an activating mutation is delE746-A750. In some embodiments, the present invention provides a method for irreversibly inhibiting at least one mutant of EGFR in a patient, wherein an activating mutation is L858R. In some embodiments, the present invention provides a method for irreversibly inhibition at least one mutant of EGFR in a patient, wherein an activating mutation is G719S.

In other embodiments, the present invention provides a method for treating a disorder mediated by one or more of at least one mutant of EGFR (e.g., a deletion mutation, an activating mutation, a resistant mutation, or combination thereof) in a patient in need thereof, comprising the step of administering to said patient Compound 1 or pharmaceutically acceptable composition thereof. Such disorders are described in detail herein.

Depending upon the particular condition, or disease, to be treated, additional therapeutic agents, which are normally administered to treat that condition, may also be present in the compositions of this invention or as part of a treatment regimen including Compound 1. As used herein, additional therapeutic agents that are normally administered to treat a particular disease, or condition, are known as "appropriate for the disease or condition being treated."

For example, Compound 1 or a pharmaceutically acceptable composition thereof is administered in combination with chemotherapeutic agents to treat proliferative diseases and cancer. Examples of known chemotherapeutic agents include, but are not limited to, Adriamycin, dexamethasone, vincristine, cyclophosphamide, fluorouracil, topotecan, taxol, interferons, platinum derivatives, taxane (e.g., paclitaxel), vinca alkaloids (e.g., vinblastine), anthracyclines (e.g., doxorubicin), epipodophyllotoxins (e.g., etoposide), cisplatin, an mTOR inhibitor (e.g., a rapamycin), methotrexate, actinomycin D, dolastatin 10, colchicine, emetine, trimetrexate, metoprine, cyclosporine, daunorubicin, teniposide, amphotericin, alkylating agents (e.g., chlorambucil), 5-fluorouracil, camptothecin, cisplatin, metronidazole, and Gleevec™, among others. In other embodiments, Compound 1 is administered in combination with a biologic agent, such as Avastin or VECTIBIX.

In certain embodiments, Compound 1 or a pharmaceutically acceptable composition thereof is administered in combination with an antiproliferative or chemotherapeutic agent selected from any one or more of abarelix, aldesleukin, alemtuzumab, alitretinoin, allopurinol, altretamine, amifostine, anastrozole, arsenic trioxide, asparaginase, azacitidine, BCG Live, bevacuzimab, fluorouracil, bexarotene, bleomycin, bortezomib, busulfan, calusterone, capecitabine, camptothecin, carboplatin, carmustine, celecoxib, cetuximab, chlorambucil, cladribine, clofarabine, cyclosphosphamide, cytarabine, dactinomycin, darbepoetin alfa, daunorubicin, denileukin, dexrazoxane, docetaxel, doxorubicin (neutral), doxorubicin hydrochloride, dromostanolone propionate, epirubicin, epoctin alfa, erlotinib, estramustine, etoposide phosphate, etoposide, exemestane, filgrastim, floxuridine fludarabine, fulvestrant, gefitinib, gemcitabine, gemtuzumab, goserelin acetate, histrelin acetate, hydroxyurea, ibritumomab, idarubicin, ifosfamide, imatinib mesylate, interferon alfa-2a, interferon alfa-2b, irinotecan, lenalidomide, letrozole, leucovorin, leuprolide acetate, levamisole, lomustine, megestrol acetate, melphalan, mercaptopurine, 6-MP, mesna, methotrexate, methoxsalen, mitomycin C, mitotane; mitoxantrone, nandrolone, nelarabine, nofetumomab, oprelvekin, oxaliplatin, paclitaxel, palifermin, pamidronate, pegademase, pegaspargase, pegfilgrastim, pemetrexed disodium, pentostatin, pipobroman, plicamycin, porfimer sodium, procarbazine, quinacrine, rasburicase, rituximab, sargramostim, sorafenib, streptozocin, sunitinib maleat, talc, tamoxifen, temozolomide, teniposide, VM-26, testolactone, thioguanine, 6-TG, thiotepa, topotecan, toremifine, tostitumomab, trastuzumab, tretinoin, ATRA, uracil mustard, valrubicin, vinblastine, vincristine, vinorelbine, zoledronate, or zoledronic acid.

Other examples of agents the inhibitors of this invention may also be combined with include, without limitation: treatments for Alzheimer's Disease such as donepezil hydrochloride (Aricept®) and rivastigmine (Exelon®); treatments for Parkinson's Disease such as L-DOPA/carbidopa, entacapone, ropinrole, pramipexole, bromocriptine, pergolide, trihexephendyl, and amantadine; agents for treating Multiple Sclerosis (MS) such as beta interferon (e.g., Avonex® and Rebif®), glatiramer acetate (Copaxone®), and mitoxantrone; treatments for asthma such as albuterol and montelukast (Singulair®); agents for treating schizophrenia such as zyprexa, risperdal, seroquel, and haloperidol; anti-inflammatory agents such as corticosteroids, TNF blockers, IL-1 RA, azathioprine, cyclophosphamide, and sulfasalazine; immunomodulatory and immunosuppressive agents such as cyclosporin, tacrolimus, rapamycin, mycophenolate mofetil, interferons, corticosteroids, cyclophophamide, azathioprine, and sulfasalazine; neurotrophic factors such as acetylcholinesterase inhibitors, MAO inhibitors, interferons, anticonvulsants, ion channel blockers, riluzole, and anti-Parkinsonian agents; agents for treating cardiovascular disease such as beta-blockers, ACE inhibitors, diuretics, nitrates, calcium channel blockers, and statins; agents for treating liver disease such as corticosteroids, cholestyramine, interferons, and anti-viral agents; agents for treating blood disorders such as corticosteroids, anti-leukemic agents, and growth factors; and agents for treating immunodeficiency disorders such as gamma globulin.

In certain embodiments, Compound 1 or a pharmaceutically acceptable composition thereof is administered in combination with a monoclonal antibody or an siRNA therapeutic.

The additional agents may be administered separately from a Compound 1-containing composition, as part of a multiple dosage regimen. Alternatively, those agents may be part of a single dosage form, mixed together with Compound 1 in a single composition. If administered as part of a multiple dosage regime, the two active agents may be submitted simultaneously, sequentially or within a period of time from one another (e.g., one hour, two hours, six hours, twelve hours, one day, one week, two weeks, one month).

As used herein, the terms "combination," "combined," and related terms refer to the simultaneous or sequential administration of therapeutic agents in accordance with this invention. For example, Compound 1 may be administered with another therapeutic agent simultaneously or sequentially in separate unit dosage forms or together in a single unit dosage form. Accordingly, the present invention provides a single unit dosage form comprising Compound 1, an additional therapeutic agent, and a pharmaceutically acceptable carrier, adjuvant, or vehicle.

The amount of Compound 1 and additional therapeutic agent (in those compositions which comprise an additional therapeutic agent as described above) that may be combined with the carrier materials to produce a single dosage form will vary depending upon the host treated and the particular mode of administration. Preferably, compositions of this invention should be formulated so that a dosage of between 0.01-100 mg/kg body weight/day of Compound 1 can be administered.

In those compositions that include an additional therapeutic agent, that additional therapeutic agent and Compound 1 may act synergistically. Therefore, the amount of additional therapeutic agent in such compositions may be less than that required in a monotherapy utilizing only that therapeutic agent. In such compositions, a dosage of between 0.01-1,000 μg/kg body weight/day of the additional therapeutic agent can be administered.

The amount of additional therapeutic agent present in the compositions of this invention will be no more than the amount that would normally be administered in a composition comprising that therapeutic agent as the only active agent. Preferably the amount of additional therapeutic agent in the presently disclosed compositions will range from about 50% to 100% of the amount normally present in a composition comprising that agent as the only therapeutically active agent.

Compound 1 or pharmaceutical compositions thereof may also be incorporated into compositions for coating an implantable medical device, such as prostheses, artificial valves, vascular grafts, stents and catheters. Vascular stents, for example, have been used to overcome restenosis (re-narrowing of the vessel wall after injury). However, patients using stents or other implantable devices risk clot formation or platelet activation. These unwanted effects may be prevented or mitigated by pre-coating the device with a pharmaceutically acceptable composition comprising a kinase inhibitor. Implantable devices coated with Compound 1 are another embodiment of the present invention.

All features of each of the aspects of the invention apply to all other aspects mutatis mutandis.

In order that the invention described herein may be more fully understood, the following examples are set forth. It should be understood that these examples are for illustrative purposes only and are not to be construed as limiting this invention in any manner.

EXEMPLIFICATION

As depicted in the Examples below, in certain exemplary embodiments, compounds are prepared according to the following general procedures. It will be appreciated that, although the general methods depict the synthesis of certain compounds of the present invention, the following general methods, and other methods known to one of ordinary skill in the art, can be applied to all compounds and subclasses and species of each of these compounds, as described herein.

Preparation of Compound 1

The synthesis of Compound 1 is described in detail at Example 3 of the '061 application.

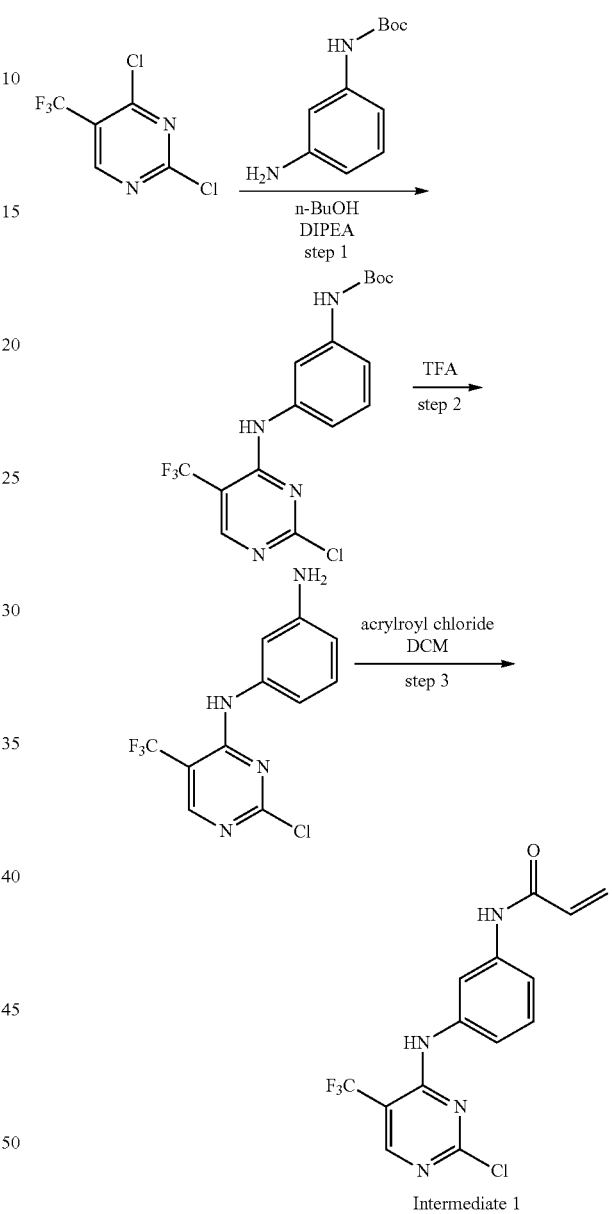

Intermediate 1

Step 1:

In a 25 mL 3-neck round-bottom flask previously equipped with a magnetic stirrer, Thermo pocket and CaCl$_2$ guard tube, N-Boc-1,3-diaminobenzene (0.96 g) and n-butanol (9.00 mL) were charged. The reaction mixture was cooled to 0° C., 2,4-Dichloro-5-trifluoromethylpyrimidine (1.0 g) was added dropwise to the above reaction mixture at 0° C. Diisopropylethylamine (DIPEA) (0.96 mL) was dropwise added to the above reaction mixture at 0° C. and the reaction mixture was stirred for 1 hr at 0° C. to 5° C. Finally, the reaction mixture was allowed to warm to room temperature. The reaction mixture was stirred for another 4 hrs at room temperature. Completion of reaction was monitored by TLC using hexane:ethyl acetate (7:3). The solid precipitated out was filtered off and washed with 1-butanol (2 mL). The solid was dried under reduced pressure at 40° C. for 1 hr. $^1$H NMR (DMSO-d6, 400 MHz) δ 1.48 (S, 9H), 7.02 (m, 1H), 7.26 (m, 2H), 7.58 (S, 1H), 8.57 (S, 1H), 9.48 (S, 1H), 9.55 (S, 1H).

Step 2:

To the above crude (3.1 g) in dichloromethane (DCM) (25 mL) was added trifluoroacetic acid (TFA) (12.4 mL) slowly at 0° C. The reaction mixture was allowed to warm to room temperature. The reaction mixture was stirred for another 10 min at room temperature. The crude was concentrated under reduced pressure.

Step 3:

The concentrated crude was dissolved in DIPEA (2.0 mL) and dichloromethane (25 mL), and then cooled to −30° C. To the reaction mixture was slowly added acryloyl chloride (0.76 g) at −30° C. The reaction mass was warmed to room temperature stirred at room temperature for 1.0 hr. The reaction was monitored on TLC using hexane:ethyl acetate (7:3) as mobile phase. The reaction was completed after 1 hr. Step 3 yielded intermediate 1.

Step 4:

To obtain a salt of compound 1, a mixture of intermediate 1 (16 mg) and 2-methoxy-4-(4-acetylpiperazinyl)aniline in dioxane (1.0 mL) with catalytic trifluoroacetic acid was stirred overnight at 50° C. The crude was concentrated under reduced pressure and purified using HPLC (TFA modifier) to give compound 1 as a TFA salt. $^1$H NMR (DMSO-d$_6$, 400 MHz) δ 10.2 (S, 1H), 8.2 (br, 1H), 8.30 (S, 1H), 7.73 (br, 1H), 7.52 (d, J=7.8 Hz, 1H), 7.45 (d, J=7.8 Hz, 1H), 7.26 (J=8.2 Hz, 1H), 7.14 (be, 1H), 6.60 (S, 1H), 6.42 (dd, J=11.4, 16.9 Hz, 1H), 6.24 (d, J=16.9 Hz, 1H), 5.75 (d, J=11.4 Hz, 1H), 3.76 (S, 3H), 3.04 (br, 4H), 2.04 (S, 3H); calculated mass for $C_{27}H_{28}F_3N_7O_3$: 555.2, found: 556.2 (M+H$^+$).

Step 5:

To obtain the free base form of Compound 1 from the TFA salt, the salt was added to DCM and cooled to 0° C. $Na_2CO_3$ solution (9.6% w/w) was added at 0° C. The mixture was warmed to 20° C. and stirred for 35 min. The pH of the aqueous layer was >8. The layers were separated. Extraction of the aqueous layer was performed using DCM. The organic layers were combined and washed with brine. The organic layer was collected and evaporated to yield a solid of Compound 1.

General Procedures

X-ray powder diffraction (XRPD) analysis was carried out on a Siemens D5000, scanning the samples between 3 and 30 or 50° 2-theta. For samples <100 mg, ca. 5-10 mg of sample was gently compressed onto a glass slide which fitted into the sample holder. For samples >100 mg, ca. 100 mg of sample was gently compressed into a plastic sample holder, so that the sample surface was smooth and just above the level of the sample holder. Measurements were made as follows:

| | |
|---|---|
| step size | 0.02 °2-theta |
| scan step time | 1 s |
| offset | 0 °2-theta |
| divergence slit type | fixed |
| divergence slit size | 2.0000° |
| receiving slit size | 0.2 mm |
| temperature | 20° C. |
| anode material | copper |
| K-Alpha1 | 1.54060 Angstroms |
| K-Alpha2 | 1.54443 Angstroms |
| K-Beta | 1.39225 Angstroms |
| K-A2/K-A1 Ratio | 0.50000 |
| Geneator settings | 40 mA, 40 kV |
| goniometer radius | 217.50 |

In polarized light microscopy (PLM), the presence of crystallinity (birefringence) was determined using an Olympus BX50 polarising microscope, equipped with a Motic camera and image capture software (Motic images Plus 2.0). All images were recorded using the 20× objective, unless otherwise stated.

For thermogravimetric analysis (TGA), approximately 5-10 mg of material was accurately weighed into an open aluminium pan and loaded into a simultaneous thermogravimetric/differential thermal analyser (TG/DTA) and held at room temperature. The sample was then heated at a rate of 10° C./min from 25° C. to 300° C. during which time the change in sample weight was recorded along with any differential thermal events (DTA), Nitrogen was used as the purge gas, at a flow rate of 100 cm$^3$/min.

For differential scanning calorimetry (DSC), approximately 5-10 mg of material was weighed into an aluminium DSC pan and sealed non-hermetically with a pierced aluminium lid. The sample pan was then loaded into a Seiko DSC6200 (equipped with a cooler) cooled and held at 25° C. Once a stable heat-flow response was obtained, the sample and reference were heated to ca. 260° C. at scan rate of 10° C./min and the resulting heat flow response monitored.

$^1$H-NMR experiments were performed on a Bruker AV400 ($^1$H frequency: 400 MHz). $^1$H experiments of each sample were performed in deuterated DMSO and each sample was prepared to ca. 10 mg concentration.

For dynamic vapour sorption (DVS), approximately 10 mg of sample was placed into a wire mesh vapour sorption balance pan and loaded into a DVS-1 dynamic vapour sorption balance by Surface Measurement Systems. The sample was subjected to a ramping profile from 20-90% relative humidity (RH) at 10% increments, maintaining the sample at each step until a stable weight had been achieved (99.5% step completion). After completion of the sorption cycle, the sample was dried using the same procedure, but all the way down to 0% RH and finally taken back to the starting point of 20% RH. The weight change during the sorption/desorption cycles were plotted, allowing for the hygroscopic nature of the sample to be determined.

Infrared spectroscopy (IR) was carried out on a Bruker ALPHA P spectrometer. Sufficient material was placed onto the centre of the plate of the spectrometer and the spectra were obtained using the following parameters: resolution—4 cm$^{-1}$, background scan time—16 scans, sample scan time—16 scans, data collection 4000 to 400 cm$^{-1}$, result spectrum—transmittance.

For Karl Fischer (KF) Coulometric titration, 10-15 mg of solid material was accurately weighed into a vial. The solid was then manually introduced into the titration cell of a Mettler Toledo C30 Compact Titrator. The vial was back-weighed after the addition of the solid and the weight of the added solid entered on the instrument. Titration was initiated once the sample had fully dissolved in the cell. The water content was calculated automatically by the instrument as a percentage and the data printed.

Reverse-phase gradient high performance liquid chromatography (HPLC) was performed on an Agilent 1100 instrument fitted with a C18, 3.0×100 mm×3.5 μm column. The detection wavelength was 240 nm.

A Sotax AT7 dissolution bath (USP 2, EP 2 apparatus) was used for the dissolution study in which paddles were used to stir the media. All tests were carried out at 37° C. and a paddle speed of 100 rpm.

Samples of each form were exposed to an environment of 40° C./75% RH for 1 week and 2 week periods to determine stability. Resulting solids were analysed by XRPD and HPLC to establish if any changes had occurred.

Slurries of all each polymorphic form were created in deionised water and shaken for ca. 24 hours. The resulting solid was then analysed by HPLC to determine the concentration of material dissolved.

Example 1

Preparation of Form A ca. 120 mg of Compound 1 was weighed into a vial and slurried in ca. 2 ml of acetonitrile. This was temperature cycled between ca. 0° C. and ambient (ca. 22° C.) whilst stirring in 2 hour cycles for a period of 2-3 days. Overnight, the sample was kept at ca. 2-5° C. Solid material was isolated and left to dry under vacuum for 7 days.

XRPD analysis (FIG. 1) showed the material to be crystalline. PLM analysis (not shown) indicated very fine, birefringent needle-like crystals. TGA/DTA (FIG. 2) showed a 0.4% weight loss from the outset to ca. 150° C. likely due to unbound solvent. No significant weight losses seen prior to degradation. DSC analysis (FIG. 3) showed a single endotherm at onset ca. 203.2° C. (peak 207.5° C.) due to the melt. IR analysis (FIG. 4) corresponds with the input freebase material. $^1$H NMR (not shown) carried out in deuterated DMSO showed a spectrum which corresponded with the input freebase. Acetonitrile does not appear to be present. DVS analysis (FIG. 5) showed a water uptake of 0.87% between 20 and 70% RH, indicating a non-hygroscopic material. Post DVS XRPD indicated that the material remained Form A (data not shown). No polymorphic form changes were evident. Some loss in crystallinity was observed. KF analysis did not detect the presence of water. HPLC purity analysis indicated a purity of ca. 97.6%. Form A could not be detected by HPLC analysis for the aqueous solubility. The aqueous solubility is therefore poor.

XRPD analysis after 1 week storage (open container) at 40° C./75% RH showed the material to still be consistent with Form A, with some loss in crystallinity. HPLC analysis indicated a purity of ca. 97.5%. XRPD analysis after 2 week storage (open container) at 40° C./75% RH showed the material to still be consistent with Form A, however, it became poorly crystalline. HPLC analysis indicated a purity of ca. 96.3%.

Example 2

Preparation of Form B ca. 120 mg of Compound 1 was weighed into a vial and slurried in ca. 2 ml tetrahydrofuran. This was temperature cycled between ca. 0° C. and ambient (ca. 22° C.) whilst stirring in 2 hour cycles for a period of 2-3 days. Overnight, the sample was kept at ca. 2-5° C. Solid material was isolated and left to dry under vacuum at ambient for 7 days and at 40° C. for a further 2 days.

XRPD analysis (FIG. 6) showed the material produced to be crystalline. PLM analysis (not shown) indicated birefringent, rod-like crystals. TGA/DTA (FIG. 7) showed no significant weight losses prior to degradation after drying for 7 days at ambient under vacuum, and a further 2 days at 40° C. DSC analysis (FIG. 8) showed an endotherm at onset 153.6° C. (peak 157.6°) directly followed by an exotherm at peak 161.3° C. indicating a polymorphic transition. A further small endotherm is present at peak 186.0° C., followed by a final endotherm at onset 203.9° C. (peak 207.9° C.) which appears to correspond with the Form A melt. IR analysis (FIG. 9) showed a significant number of differences and shifts in comparison to Form A. $^1$H NMR (not shown) carried out in deuterated DMSO showed a spectrum which corresponded with the input freebase. Traces of THF appear to be present. DVS analysis (FIG. 10) showed a water uptake of 0.74% between 20 and 70% RH, indicating a non-hygroscopic material. Post DVS XRPD (not shown) indicated that the material remained Form B. No polymorphic form changes were evident. KF (not shown) analysis indicated the presence of ca. 0.97% water. HPLC purity analysis indicated a purity of ca. 97.0%. Form B could not be detected by HPLC analysis for the aqueous solubility. The aqueous solubility is therefore poor.

XRPD analysis after 1 week storage (open container) at 40° C./75% RH showed the material to be predominantly amorphous. HPLC analysis indicated a purity of ca. 96.8%. XRPD analysis after 2 week storage (open container) at 40° C./75% RH showed the material to be predominantly amorphous. HPLC analysis indicated a purity of ca. 95.9%.

Figure 11:
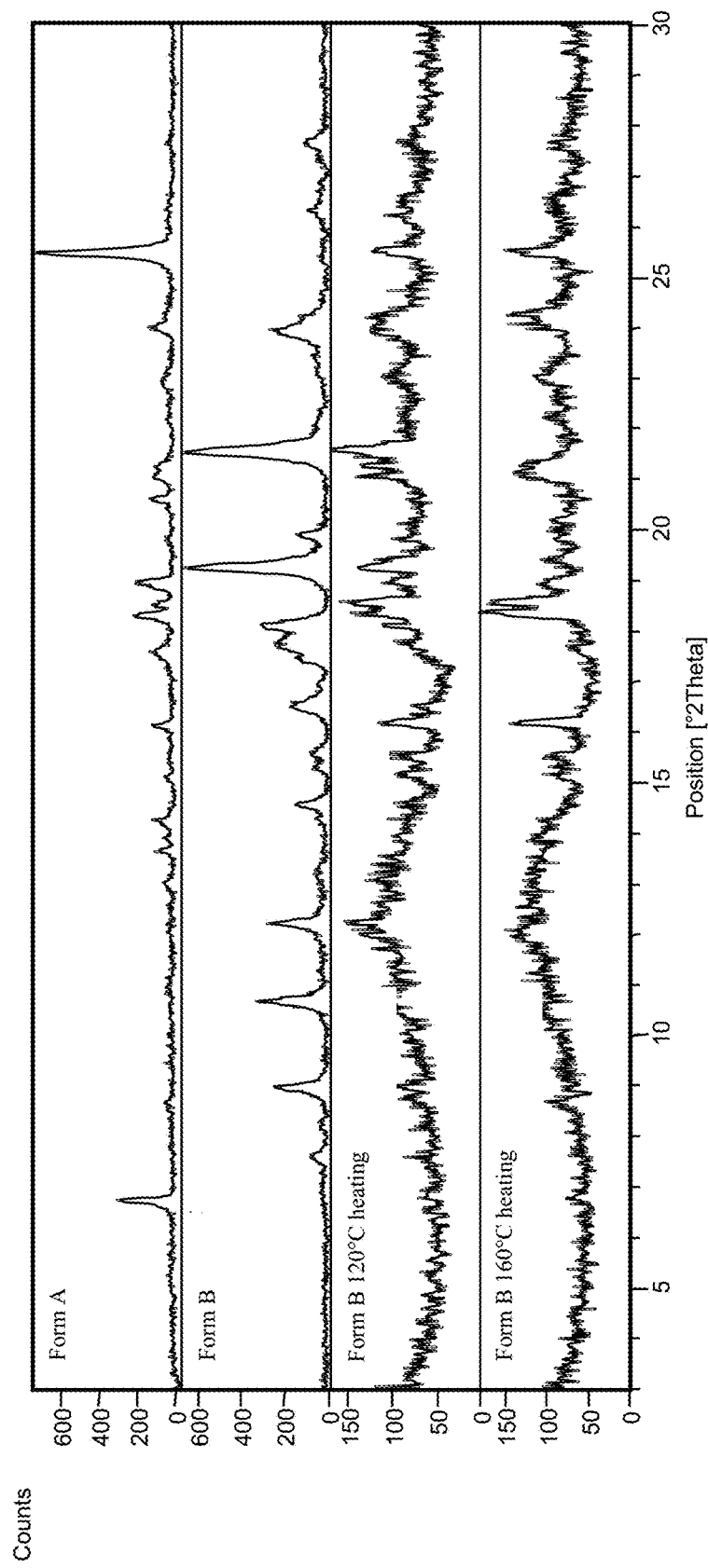
FIG. 11 depicts the change in the XRPD pattern for Form B of Compound 1 when heated to 120° C. and 160° C., respectively, as compared to Forms A and B at ambient temperature.

In order to determine the relationship between Forms A and B, a sample of Form B was heated to 120° C. and then XRPD analysis was carried out. The XRPD showed a mixture of Form B and Form A, indicating that as Form B is heated, it starts to convert to Form A. Form B was also heated to 160° C. (temperature above phase transition seen in DSC) and then XRPD analysis was carried out which indicated that the material converted predominantly to Form A at this temperature. The comparative XRPD results are shown in FIG. 11.

Example 3

Preparation of Form C ca. 120 mg of Compound 1 was weighed into a vial and slurried in ca. 100 µl of DMF. This was temperature cycled between ca. 0° C. and ambient (ca. 22° C.) whilst stirring in 2 hour cycles. After ca. 2 hours, a further 300 µl of DMF was added. The temperature cycling was continued for a period of 2-3 days. Overnight, the sample was kept at ca. 2-5° C. Solid material was isolated and left to dry under vacuum at ambient for 7 days and at 40° C. for a further 2 days.

XRPD analysis (FIG. 12) showed the material to be crystalline. PLM analysis (not shown) indicated birefringent, rod-like crystals. TGA/DTA (FIG. 13) showed a weight loss of ca. 8.2%. (11.6 wt % DMF required for a mono solvate) after drying for 7 days at ambient under vacuum and a further 2 days at 40° C. DSC analysis (FIG. 14) showed a broad endotherm between 85-125° C., corresponding with the weight loss in the TGA. A final endotherm is seen at onset ca. 204.4° C. (peak 208.3° C.) corresponding with the Form A melt. IR analysis (FIG. 15) showed some differences and shifts in comparison with Form A. $^1$H NMR (not shown) carried out in deuterated DMSO showed a spectrum which corresponds with the input freebase with some DMF present (ca. 3:1 API:DMF). DVS analysis (FIG. 16) corresponded with the TGA data where the material is seen to contain solvent, which is lost as the relative humidity is increased. Post DVS XRPD (not shown) indicated that the material converted to Form A during DVS analysis. KF analysis (not shown) indicated the presence of ca. 0.01% water. HPLC purity analysis indicated a purity of ca. 97.3%. Form C could not be detected by HPLC analysis for the aqueous solubility. The solubility is therefore poor.

Figure 17:
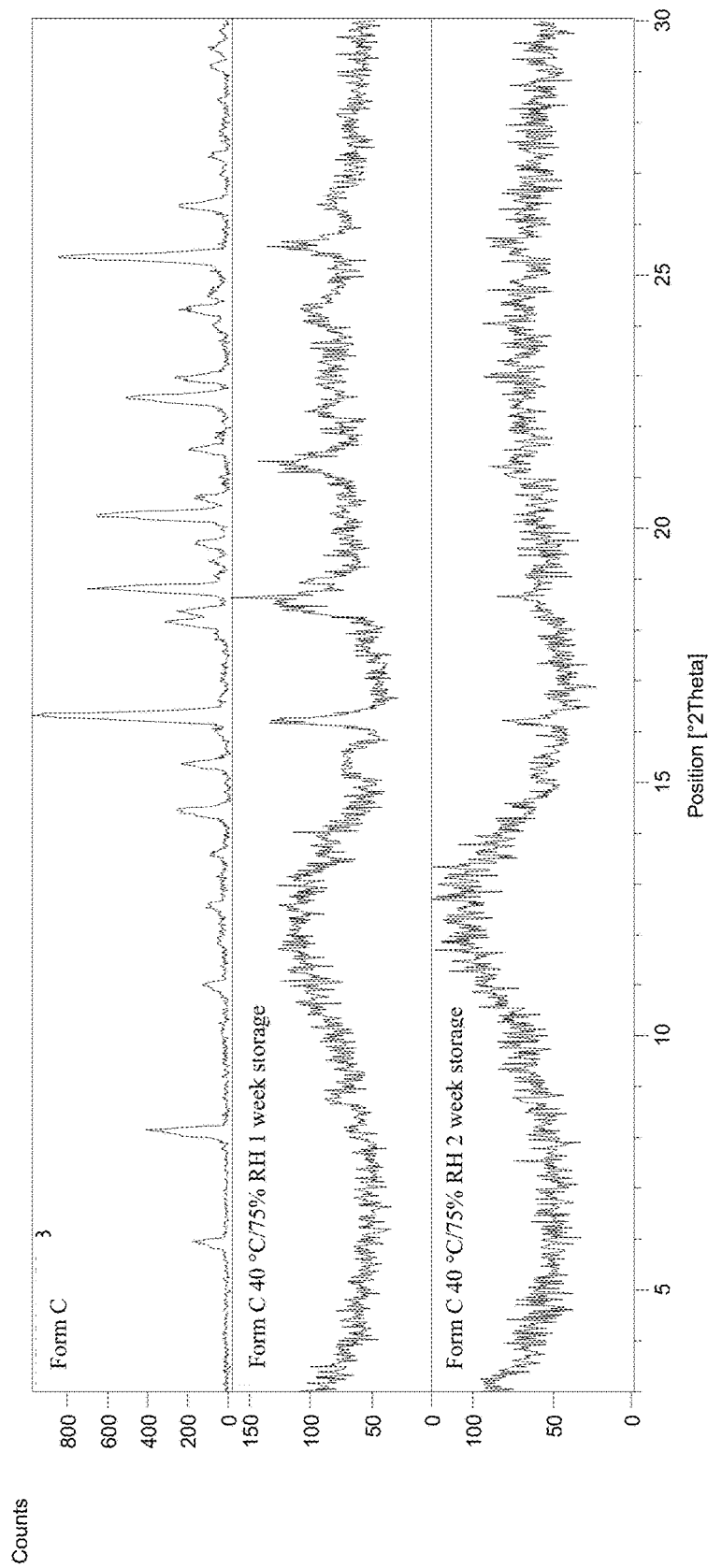
FIG. 17 depicts the change in the XRPD pattern for Form C of Compound 1 when stored at 40° C./75% RH for 1 week or 2 weeks, respectively, as compared to the initial forms of Form A and Form C.

XRPD analysis after 1 week storage (open container) at 40° C./75% RH showed the material converted to Form A with some loss in crystallinity. HPLC analysis indicated a purity of ca. 97.1%. XRPD analysis after 2 week storage (open container) at 40° C./75% RH showed the material to be poorly crystalline with the peaks present corresponding with Form A. HPLC analysis indicated a purity of ca. 96.8%. The comparative XRPD results are shown in FIG. 17.

Figure 18:
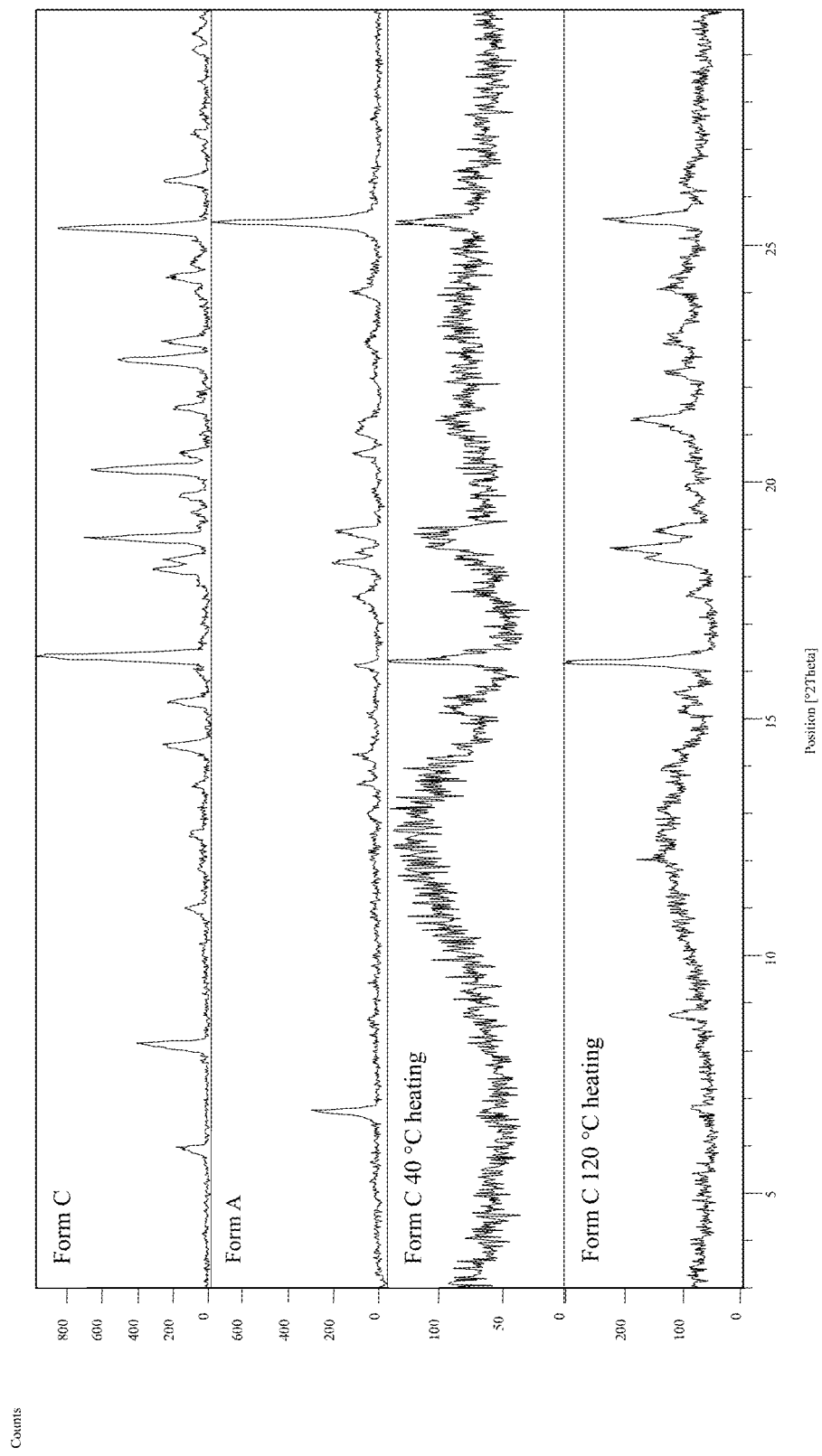
FIG. 18 depicts the change in the XRPD pattern for Form C of Compound 1 when heated to 40° C. and 120° C., as compared to Forms A and C prior to drying.

To determine whether Form C remains the same after losing the solvent present, a sample of Form C was heated to 120° C. (i.e., just past the temperature at which the solvent is removed) and then XRPD analysis was carried out. The XRPD showed that the material had converted to Form A. Similarly, after drying at ambient temperature under vacuum for 7 days and then for a further 2 days at 40° C., Form C showed some loss in crystallinity and converted to Form A. The comparative XRPD results are shown in FIG. 18.

Example 4

Preparation of Form D ca. 120 mg of Compound 1 was weighed into a vial and slurried in ca. 2 ml of 1,4-dioxane. This was temperature cycled between ca. 0° C. and ambient (ca. 22° C.) whilst stirring in 2 hour cycles for a period of 2-3 days. Overnight, the sample was kept at ca. 2-5° C. Solid material was isolated and left to dry under vacuum at ambient for 7 days and at 40° C. for a further 2 days.

XRPD analysis showed that the preparation of Form D provided above resulted in a mixture of Form B and Form D (FIG. 19). PLM analysis indicated birefringent, rod-like crystals (not shown). TGA/DTA (FIG. 20A) showed a weight loss of ca. 5.5% between 60-100° C. after drying for 7 days at ambient under vacuum. After drying for 7 days at ambient under vacuum, and a further 2 days at 40° C., the TGA (FIG. 20B) showed a weight loss of ca. 1.4% between 100-150° C. DSC analysis after 40° C. drying (FIG. 21) showed a very small exotherm at ca. 146° C. A final endotherm was then seen at onset ca. 202.6° C. (peak 207.4° C.) corresponding with the Form A melt. IR analysis (FIG. 22) corresponded with the spectrum of Form B, with small 1,4-dioxane peaks present. $^1$H-NMR (not shown) carried out in deuterated DMSO after 7 days of drying at ambient temperature under vacuum showed a spectrum which corresponds with the input free base with some 1,4-dioxane present (ca. 2:1 API:1,4-Dioxane). DVS analysis (FIG. 23) corresponded with the TGA data where the material is seen to contain solvent which is lost as the relative humidity is increased. Post DVS XRPD (not shown) indicated that the material converted completely to Form B during DVS analysis. KF analysis (not shown) indicated the presence of ca. 1.1% water. HPLC purity analysis indicated a purity of ca. 96.6%. Form D could not be detected by HPLC analysis for the aqueous solubility. The solubility is therefore extremely poor.

Figure 24:
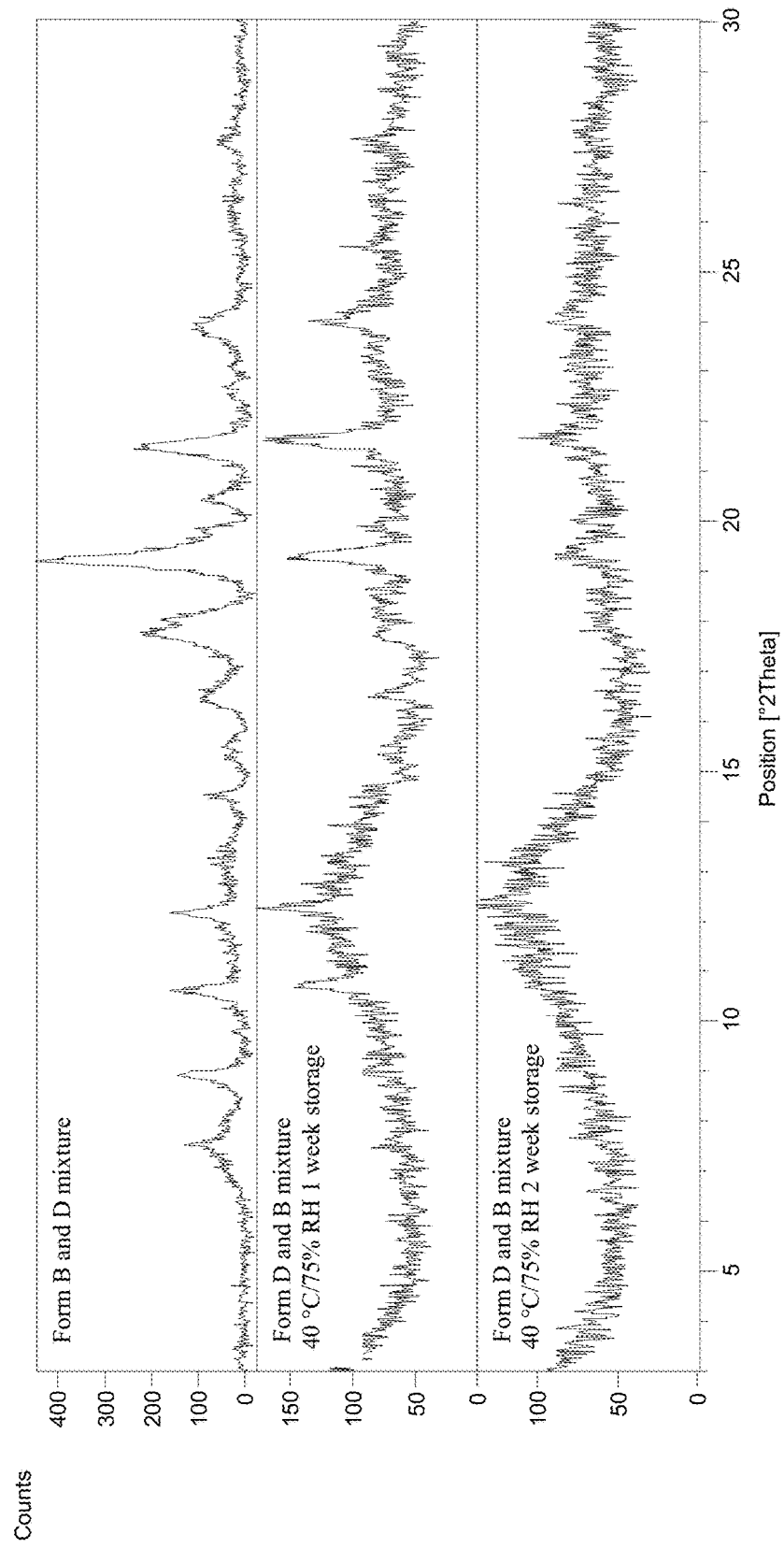
FIG. 24 depicts the change in the XRPD pattern for Form D of Compound 1 when stored 40° C./75% RH for 1 week or 2 weeks, respectively, as compared to the initial forms of Form A and Form B.

XRPD analysis after 1 week storage (open container) at 40° C./75% RH showed the material converted completely to Form B with some loss in crystallinity. HPLC analysis indicated a purity of ca. 96.5%. XRPD analysis after 2 week storage (open container) at 40° C./75% RH showed the material to be poorly crystalline with the peaks present corresponding with Form B. HPLC analysis indicated a purity of ca. 95.5%. The comparative XRPD results are shown in FIG. 24.

Example 5

Preparation of Form E ca. 120 mg of Compound 1 was weighed it to a vial and ca. 12 ml of MEK was then added in attempts to dissolve the material. A very thin slurry resulted and this was then filtered to obtain a saturated solution. The solution was placed at ca. −18° C. for crash cooling for 2-3 days. Solid material was isolated and left to dry under vacuum at ambient for 7 days and at 40° C. for a further 2 days.

XRPD analysis (FIG. 25) showed the material to be crystalline. PLM analysis (not shown) indicated birefringent, thin, rod-like crystals. TGA/DTA (FIG. 26) showed a weight loss of ca. 5.2% between ca. 70-110° C. after drying for 7 days at ambient under vacuum. DSC analysis (FIG. 27) showed a broad endotherm between 70-110° C., corresponding with the weight loss in the TGA. A final endotherm is seen at onset ca. 198.4° C. (peak 203.3° C.). IR analysis (FIG. 28) showed some small shifts in comparison with Form A. $^1$H-NMR (not shown) carried out in deuterated DMSO after 7 days of drying at ambient under vacuum showed a spectrum which corresponds with the input free base with a non-stoichiometric amount of MEK present. DVS analysis (FIG. 29) showed a water uptake of 0.25% between 20 and 70% RH. Post DVS XRPD (not shown) indicated that the material converted to Form A during DVS analysis. KF analysis (not shown) indicated the presence of ca. 1.2% water. HPLC purity analysis indicated a purity of ca 97.8%. Form E could not be detected by HPLC analysis for the aqueous solubility. The solubility is therefore extremely poor.

Figure 30:
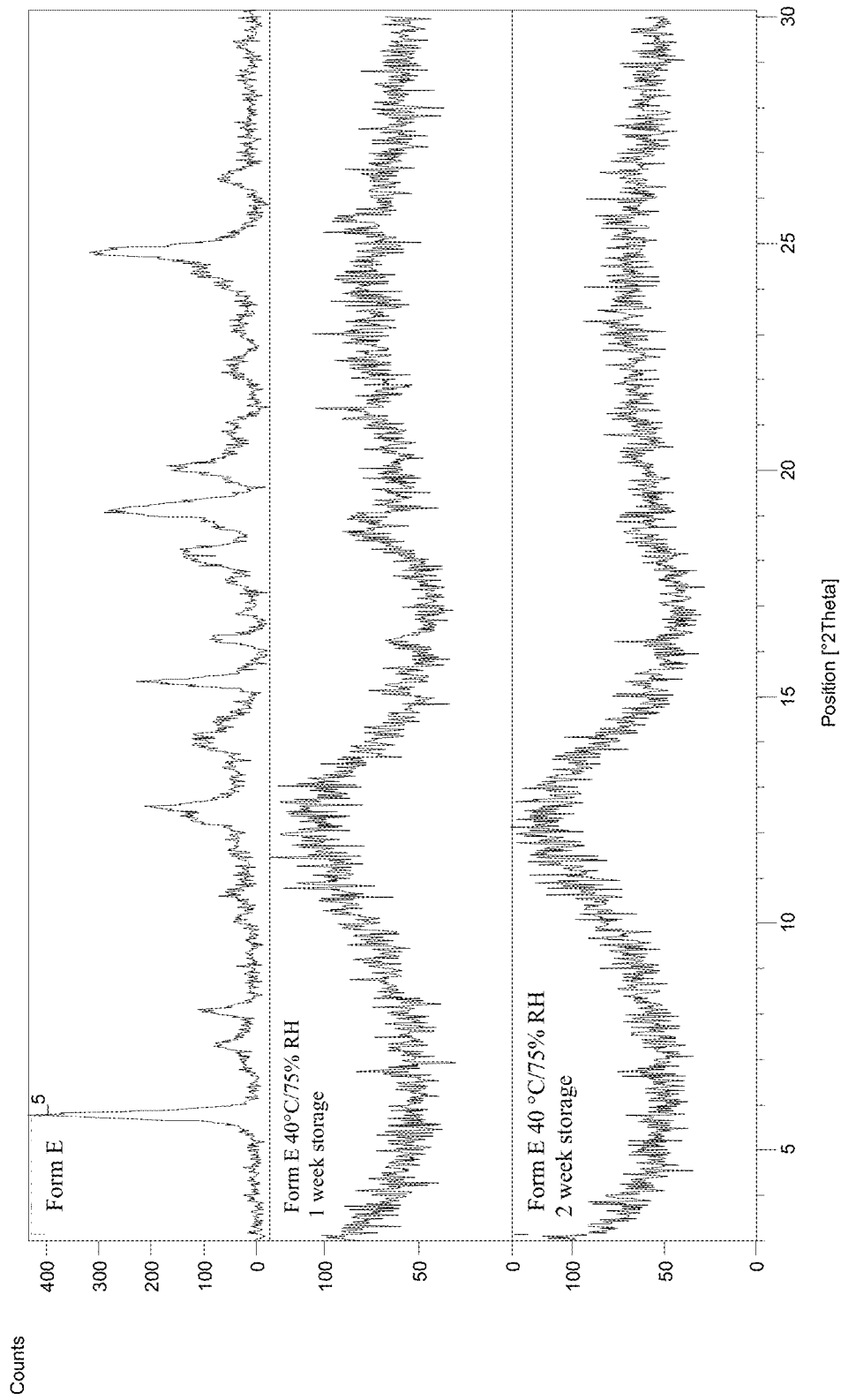
FIG. 30 depicts the change in the XRPD pattern for Form E of Compound 1 when stored at 40° C./75% RH for 1 week or 2 weeks, respectively, as compared to the initial forms of Form A and Form E.

XRPD analysis after 1 week storage (open container) at 40° C./75% RH showed the material to be predominantly amorphous with visible peaks present corresponding with Form A. HPLC analysis indicated a purity of ca. 97.7%. XRPD analysis after 2 week storage (open container) at 40° C./75% RH showed the material to be predominantly amorphous with visible peaks present corresponding with Form A. HPLC analysis indicated a purity of ca. 97.3%. The comparative XRPD results are shown in FIG. 30.

Figure 31:
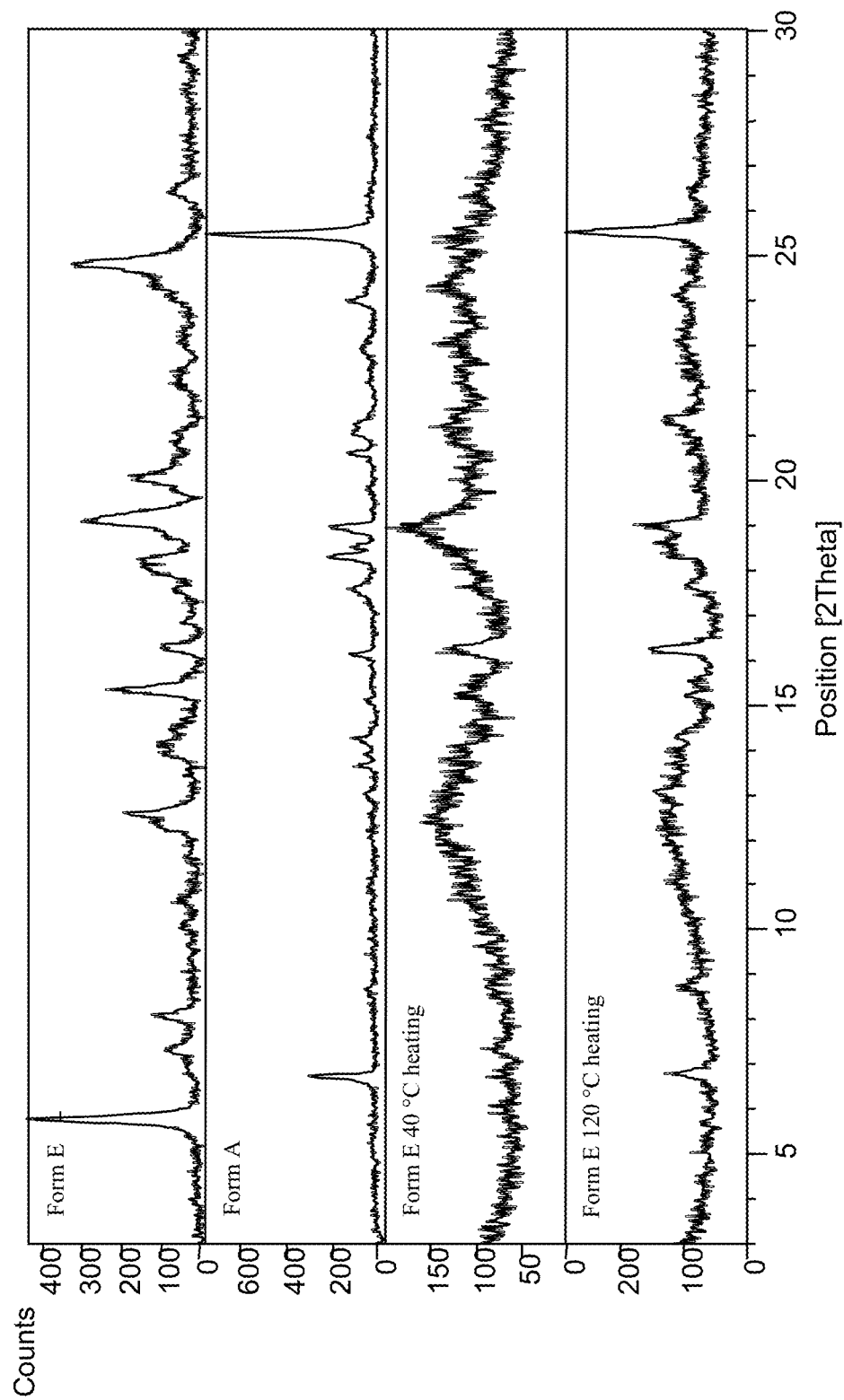
FIG. 31 depicts the change in the XRPD pattern for Form E of Compound 1 when heated to 40° C. and 120° C. as compared to Forms A and E prior to drying.

In order to determine whether Form E remains the same after losing the solvent present, a sample of Form E was heated to 120° C. (i.e., just past the temperature at which the solvent is lost) and then XRPD analysis was carried out. The XRPD showed that the material had converted to Form A. Similarly, after drying at ambient under vacuum for 7 days and then for a further 2 days at 40° C., Form E lost some crystallinity and converted to Form A. The comparative XRPD results are shown in FIG. 31.

Example 6

Preparation of Form F ca. 120 mg of Compound 1 was weighed into a vial and ca. 200 μl of NMP was then added in order to dissolve the material. Anti-solvent addition was then carried out by adding a total of ca. 4.5 ml of TBME in 500 μl aliquots to obtain a cloudy solution. The sample was then allowed to stand for ca. 2 hours before the solid was isolated. The solid material was then left to dry vacuum at ambient for 7 days and at 40° C. for a further 2 days.

XRPD analysis (FIG. 32) showed the material to be crystalline. PLM analysis (not shown) indicated birefringent, very thin, plate-like crystals which appear to grow in clusters. TGA/DTA (FIG. 33) showed a weight loss of ca. 10.2% between 70-120° C. (15.1 wt % NMP required for a mono solvate) after drying for 7 days at ambient temperature under vacuum. DSC analysis (FIG. 34) showed an endotherm at onset 97° C. (peak 100.9° C.) corresponding with the weight loss in the TGA. A final endotherm is seen at onset ca. 204.2° C. (peak 208.3° C.) corresponding with the Form A melt. IR analysis (FIG. 35) showed some small shifts in comparison with Form A. $^1$H-NMR (not shown) carried out in deuterated DMSO after 7 days of drying at ambient under vacuum showed a spectrum which corresponds with the input free base with a non-stoichiometric amount of NMP present. DVS analysis (FIG. 36) corresponded with the TGA data where the material is seen to contain solvent, which is lost as the relative humidity is increased. Post DVS XRPD (not shown) indicated that the material converted predominantly to Form A (traces of Form F remaining). KF analysis (not shown) indicated the presence of ca. 0.87% water. HPLC purity analysis indicated a purity of ca. 97.0%. Form F could not be detected by HPLC analysis for the aqueous solubility. The solubility is therefore poor.

Figure 37:
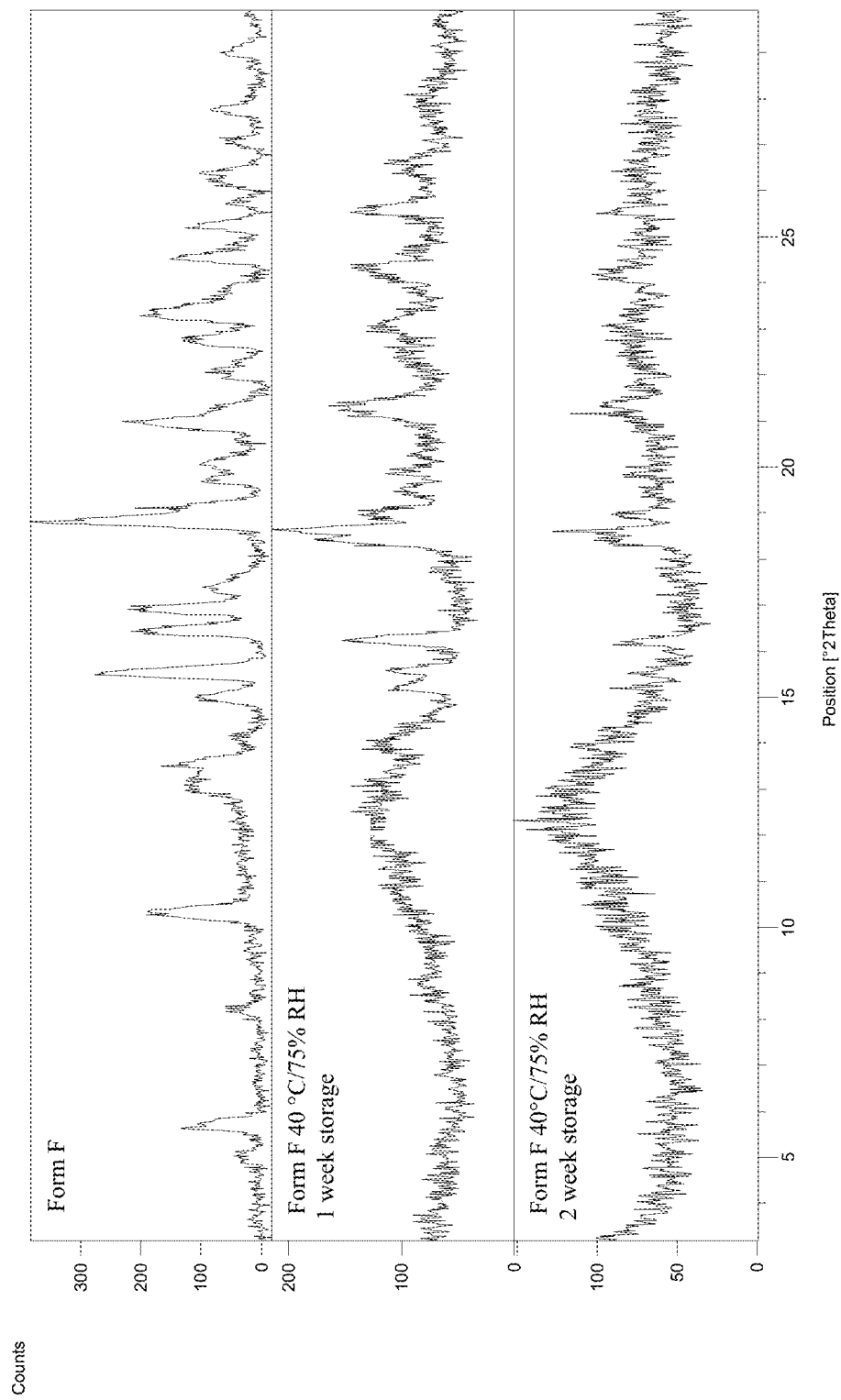
FIG. 37 depicts the change in the XRPD pattern for Form F of Compound 1 when stored at 40° C./75% RH for 1 week or 2 weeks, respectively, as compared to the initial forms of Form A and Form F.

XRPD analysis after 1 week storage (open container) at 40° C./75% RH showed the material converted to Form A, with some loss in crystallinity. HPLC analysis indicated a purity of ca. 96.8%. XRPD analysis after 2 week storage (open container) at 40° C./75% RH showed the material to be partially crystalline with peaks present corresponding with Form A. HPLC analysis indicated a purity of ca. 96.3%. The comparative XRPD results are shown in FIG. 37.

Figure 38:
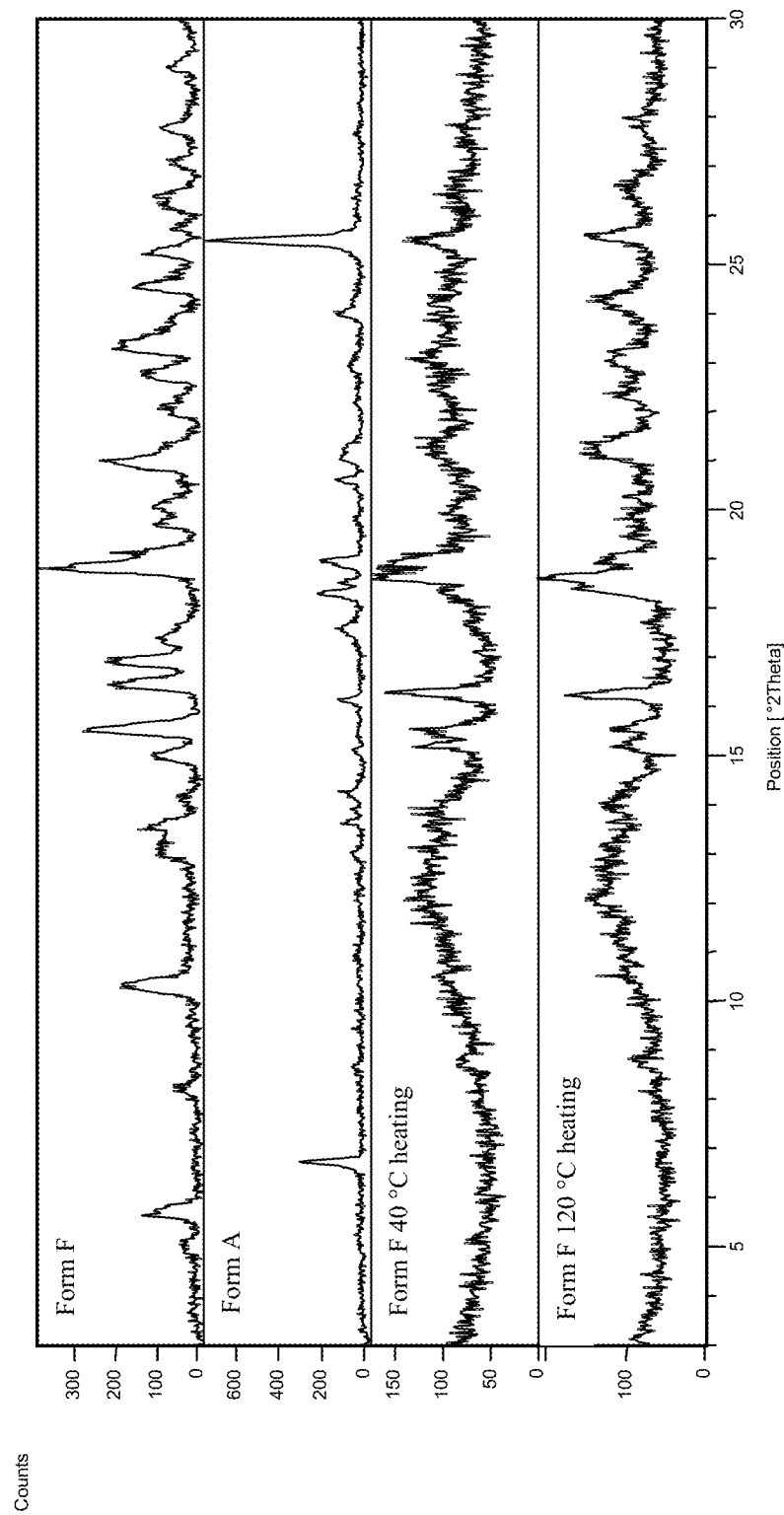
FIG. 38 depicts the change in the XRPD pattern for Form F of Compound 1 when heated to 40° C. and 120° C., as compared to Forms A and F prior to drying.

In order to determine whether Form F remains the same after losing the solvent present, a sample of Form F was heated to 120° C. (i.e., just past the temperature at which the solvent is lost) and then XRPD analysis was carried out. The XRPD showed that the material had converted predominantly to Form A. Similarly, after drying at ambient temperature under vacuum br 7 days and then for a further 2 days at 40° C., Form F lost some crystallinity and converted predominantly to Form A. The comparative XRPD results are shown in FIG. 38.

Example 7

Preparation of Form G ca. 120 mg of Compound 1 was weighed into a vial and slurried in ca. 100 µl of NMP. This was temperature cycled between ca. 0° C. and ambient (ca. 22° C.) whilst stirring in 2 hour cycles for a period of 2-3 days. Overnight, the sample was kept at ca. 2-5° C. Solid material was isolated and left to dry under vacuum at ambient for 7 days and at 40° C. for a further 2 days. A portion of the solid was also dried at 80° C. for ca. 4 days.

XRPD analysis (FIG. 39) showed the material to be crystalline. PLM analysis (not shown) indicated birefringent, plate-like crystals. TGA/DTA (FIG. 40A) showed weight losses of ca. 23.6% and 10.2% after drying for 4 days at ambient temperature under vacuum. After drying for 7 days at ambient temperature under vacuum and a further 2 days at 40° C., the TGA (FIG. 40B) showed a weight loss of ca. 6.3% between ca. 70-110° C. After drying for 4 days at 80° C., the TGA (FIG. 40C) showed a weight loss of ca. 2.8% between ca. 70-110° C. DSC analysis after drying at 80° C. (FIG. 41) showed an endotherm at onset ca. 205.3° C. (peak 210.0° C.). IR analysis after 4 days of ambient temperature drying (FIG. 42) showed some shifts in comparison with Form A and also the presence of NMP. $^1$H NMR (not shown) carried out in deuterated DMSO after 4 days of drying at ambient temperature under vacuum corresponded with the input free base with a significant amount of NMP present. DVS analysis (FIG. 43) corresponded with the TGA data, where the material is seen to contain significant amounts of solvent that are lost as the relative humidity is increased. Post DVS XRPD (not shown) indicated that the material converted to Form A. KF analysis (not shown) indicated the presence of ca. 0.45% water. HPLC purity analysis indicated a purity of ca. 97.0%. Form F in the HPLC chromatogram to determine aqueous solubility was below the limit of quantification. The aqueous solubility is therefore poor.

Figure 44:
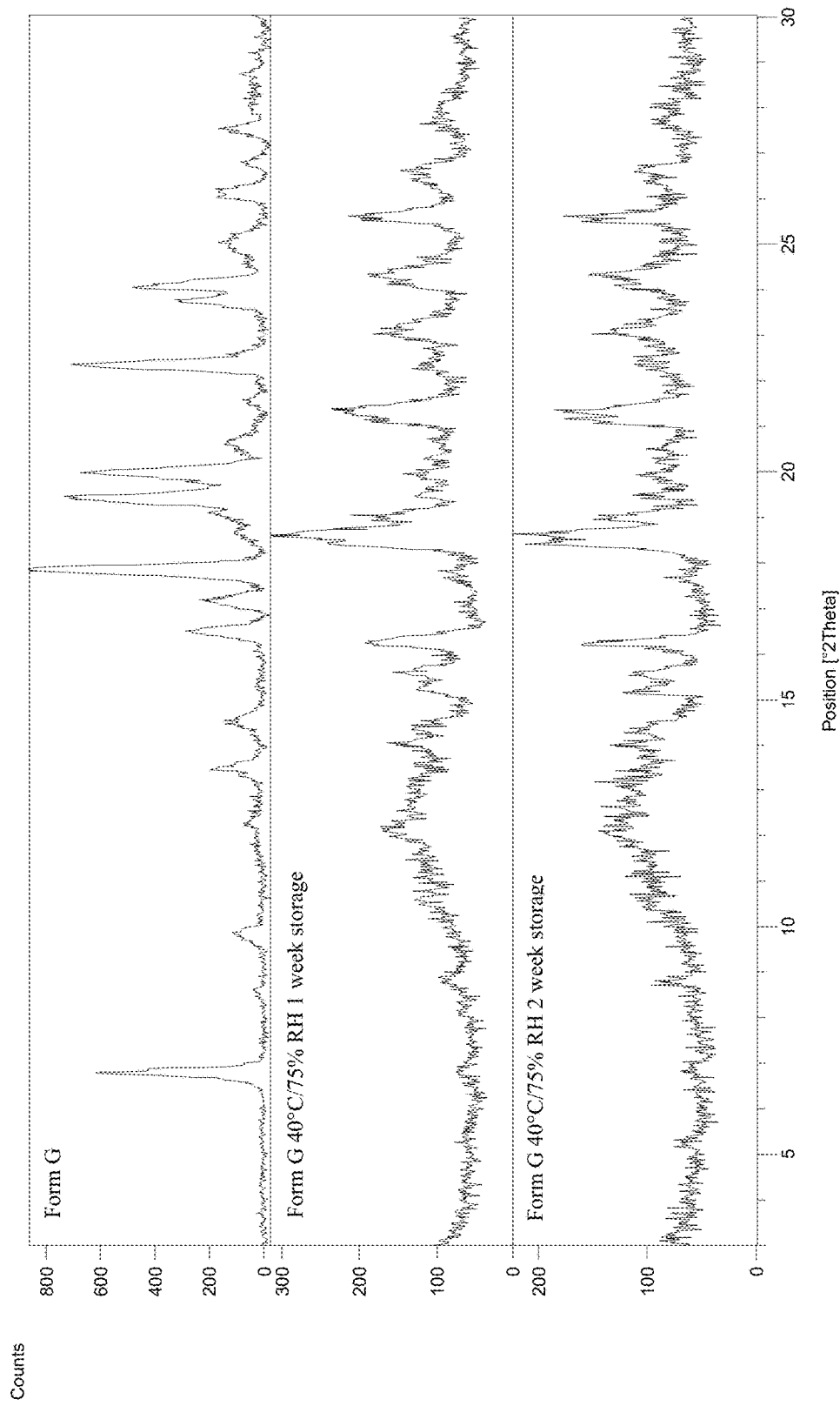
FIG. 44 depicts the change in the XRPD pattern for Form C of Compound 1 when stored at 40° C./75% RH for 1 week or 2 weeks, respectively, as compared to the initial forms of Form A and Form C.

XRPD analysis after 1 week storage (open container) at 40° C./75% RH showed the material converted predominantly to Form A, with some loss in crystallinity. HPLC analysis indicated a purity of ca. 96.8%. XRPD analysis after 2 week storage (open container) at 40° C./75% RH showed the material converted predominantly to Form A, with some loss in crystallinity. HPLC analysis indicated a purity of ca. 96.2%. The comparative XRPD results are shown in FIG. 44.

Figure 45:
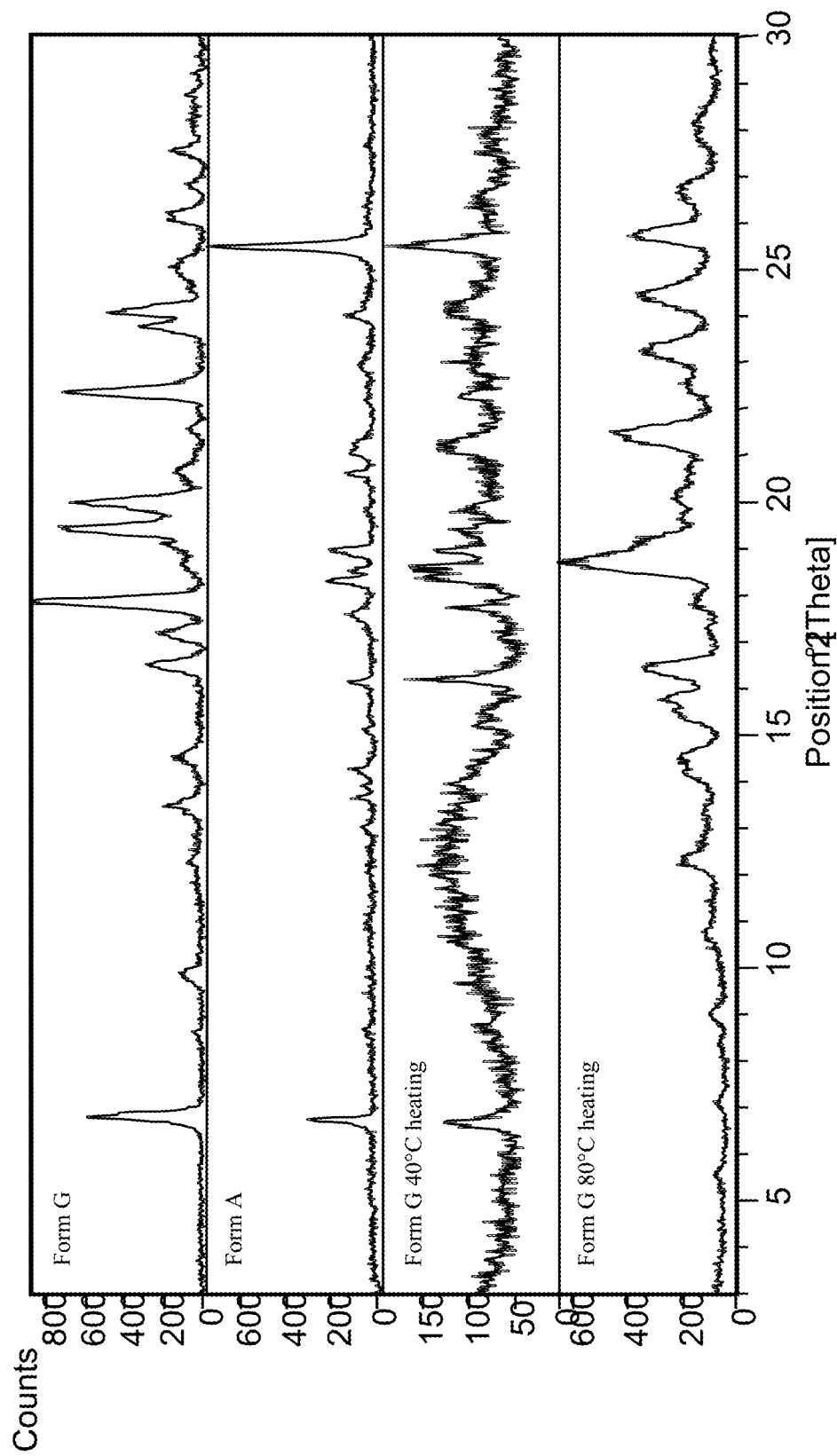
FIG. 45 depicts the change in the XRPD pattern for Form C of Compound 1 when heated to 40° C. and 80° C., as compared to Forms A and C prior to drying.

After drying at ambient under vacuum for 7 days and then for a further 2 days at 40° C., Form G converted to Form A. After drying at 80° C. for 4 days. Form G converted to Form A. The comparative XRPD results are shown in FIG. 45.

Example 8

Polymorph Stability Studies

The results from the competitive slurries carried out at ambient (ca. 22° C.) and 60° C. are tabulated below.

TABLE 1

Competitive Slurry results at ambient and 60° C.

| Solvent System | Ambient (approx. 22° C.) | 60° C. |
| --- | --- | --- |
| Dichloromethane | Form B | Form B |
| Isopropanol | Form A | Form A |
| Acetone | Form A | Form A |
| Ethyl Acetate | Form A | Form A |
| Acetone:Water (80:20) | Form A | Form H |

From slurrying at both ambient and 60° C., the majority of experiments resulted in conversion to Form A, thus indicating that Form A is likely the more stable form in comparison with Form B. Form B has been obtained consistently throughout the study from dichloromethane and tetrahydrofuran. A new polymorphic form, labelled Form H, was obtained from the competitive slurry carried out in acetone:water (80:20) at 60° C.

Example 9

Preparation of Form H ca. 10 mg of Form A and ca. 10 mg of Form B were weighed into a vial. ca. 200 µl of acetone:water (80:20%) was added to the vial to form a slurry. The sample was allowed to stir at ca. 50° C. for 3 days. The solid material was isolated and left to dry at ambient before analysis was carried out. Further drying was also carried out at 40° C. for 2 days.

XRPD analysis (FIG. 46) showed the material to be crystalline, with the diffractogram different from all identified polymorphic forms. PLM analysis (not shown) indicated birefringent, block-like crystals. The material visually appeared yellow in colour. TGA/DTA (FIG. 47) after 2 days of drying at 40° C., showed a 4.4% weight loss from the outset up to ca. 120° C. The final endotherm in the DTA trace appears to correspond with the Form A melt, (3.14 wt % is required for 1 mole equivalent of water.)

Figure 48:
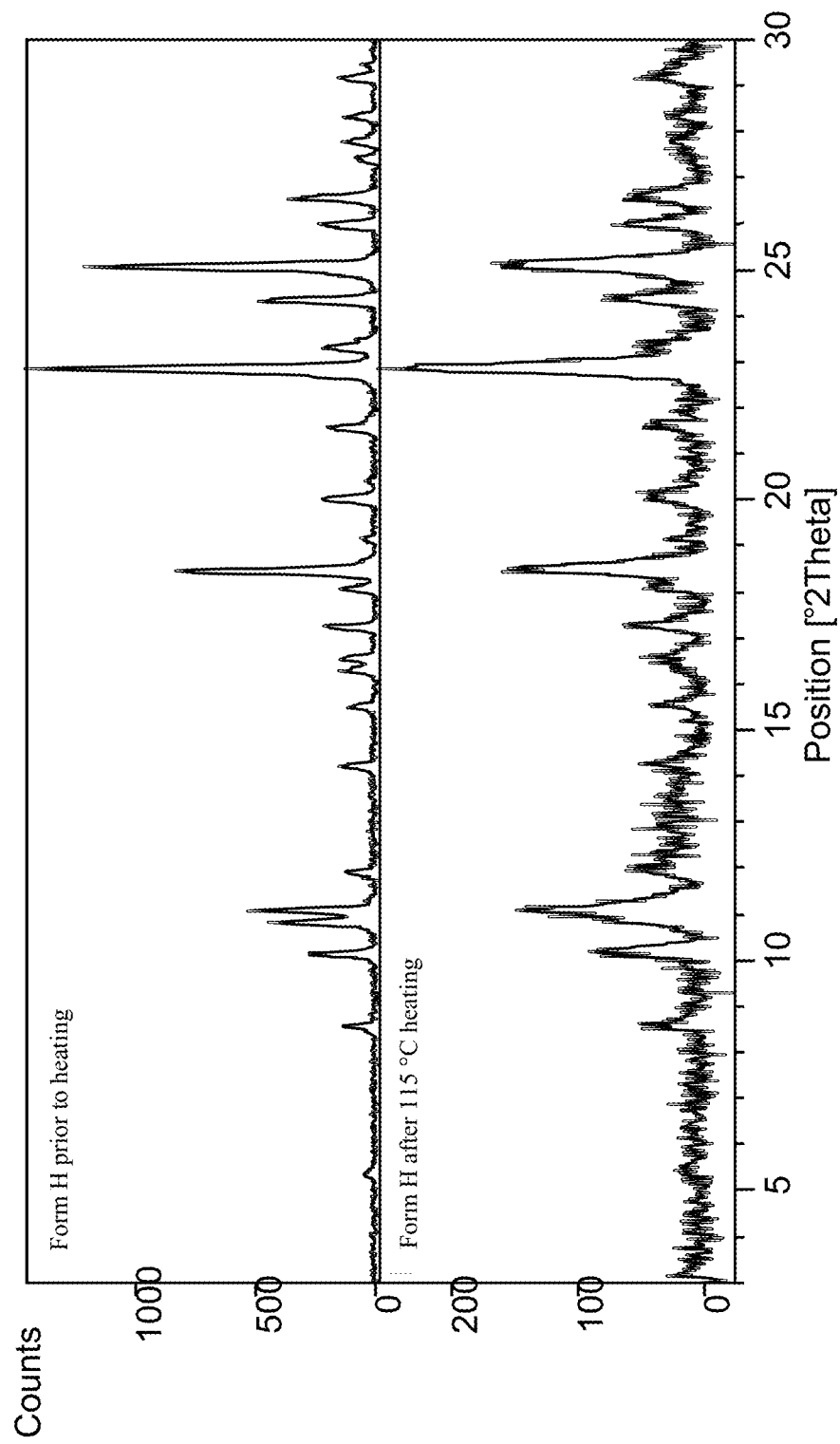
FIG. 48 depicts the XRPD pattern for Form H of Compound 1 after heating to 115° C.

To examine whether Form H changes to Form A after heating to 115° C. (point after the solvent loss), the Form H material was heated to 115° C. and XRPD analysis and DSC analysis were then carried out. The XRPD diffractogram (FIG. 48) after heating still corresponded with Form H, with some loss in crystallinity likely due to the harsh heating conditions. The DSC analysis (FIG. 49) indicated overlapping endotherms between ca. 115-135° C., followed by an exotherm at peak 143.9° C., likely indicating a polymorphic transition. A final endotherm was present at onset 202.7° C. (peak 206.6° C.) corresponding with the Form A melt.

Figure 50:
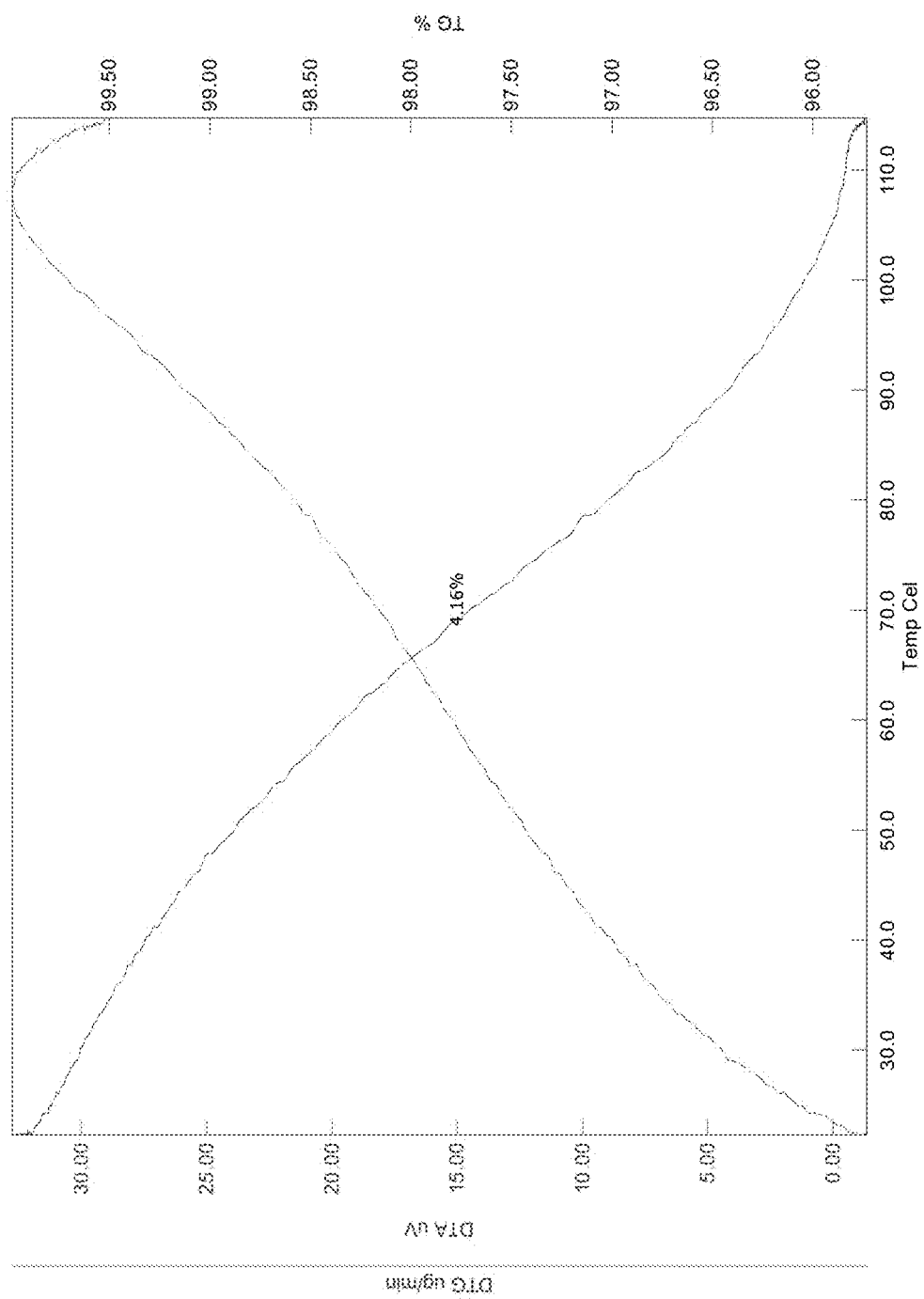
FIG. 50 depicts the TGA/DTA pattern for Form H of Compound 1 when heated to 115° C.
Figure 51:
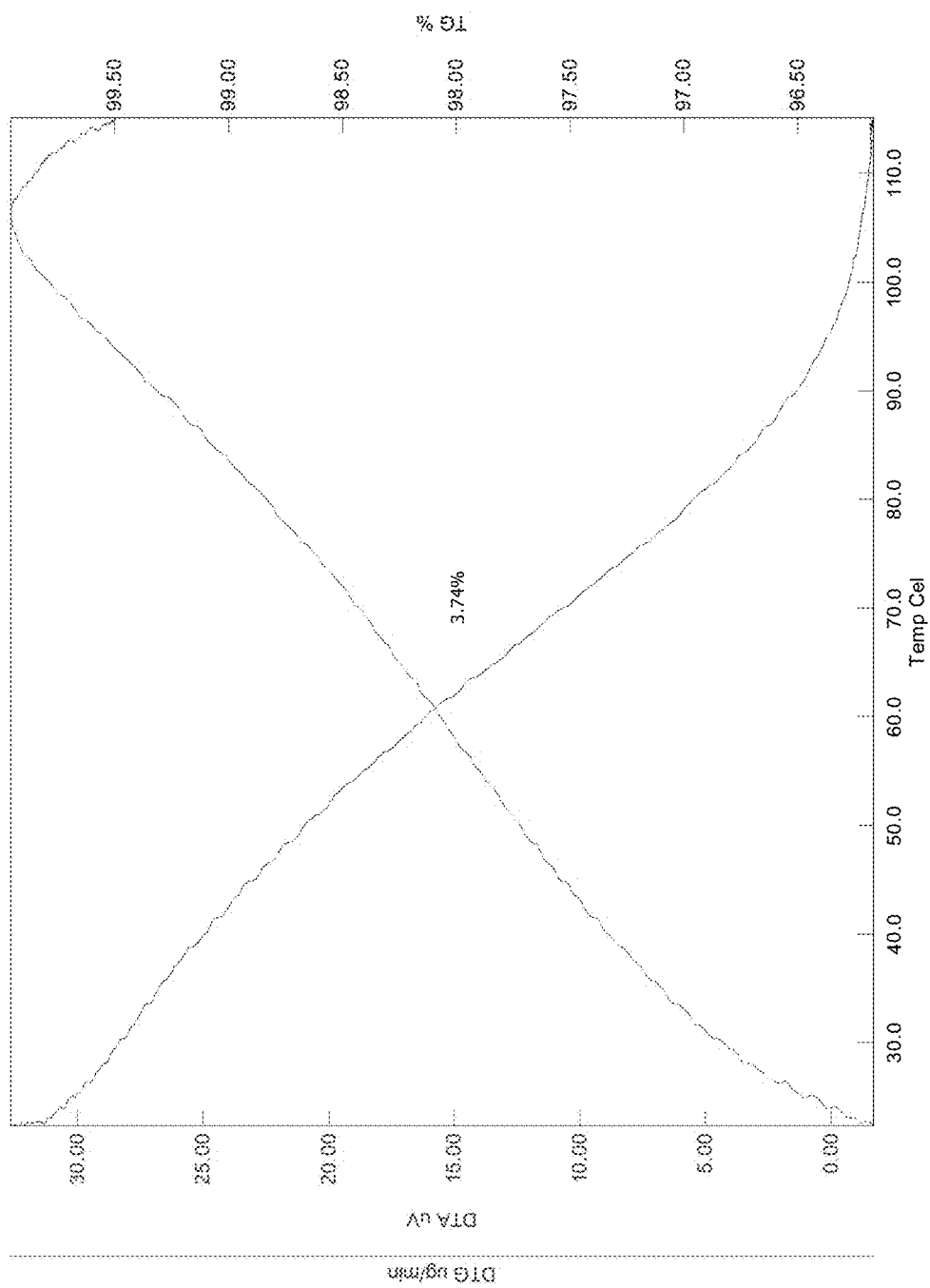
FIG. 51 depicts the TGA/DTA pattern for Form H of Compound 1 leaving the heated material on a bench for approximately one hour.

To test whether Form H picks up water after desolvating/dehydrating the material by heating to 115° C., a further test was carried out whereby Form H was heated to 115° C. in a TGA pan. The sample was then removed from the TGA pan and allowed to sit on the bench for ca. 1 hour. After 1 hour, another TGA was carried out up to 115° C. TGA for the sample heated to 115° C. showed a ca. 4.2% weight loss of the solvent/water present (FIG. 50). TGA after leaving the desolvated/dehydrated material on the bench for ca. 1 hour, showed a ca. 3.7% loss up to 115° C. (FIG. 51). The material therefore picked up water upon standing at ambient conditions on the bench. This indicates that it is either hygroscopic or rapidly rehydrates following dehydration/desolvation.

Example 10

Preparation of Form I

Approximately ca. 5 mL of acetonitrile:water (10%) was added to ca. 1 g of Compound 1 free base to form a slurry. In a separate vial, ca. 3 mL of acetonitrile:water (10%) was added to 1 equivalent of hydrobromic acid (48%). The acid solution was then added dropwise over a 1 hour period to the free base slurry whilst stirring and maintaining a temperature between 0-5° C. After the complete addition of the acid, a further 3 mL of acetonitrile:water (10%) was added. The reaction was stirred for ca. 1 day before being isolated and dried under vacuum at ambient (ca. 22° C.). A yield of ca. 79% was obtained.

Compound 1 hydrobromide salt material was ground using a Retsch Ball Mill for ca. 25 minutes, with a 5 minute break midway to prevent the sample from overheating.

Approximately 500 mg of amorphous Compound 1 hydrobromide salt material was slurried in ca. 18 mL of acetone:water (90:10). The suspension was then temperature cycled between 4 and 25° C. in four hour cycles for ca. 2 days, before being isolated and dried under vacuum at ambient (ca. 22° C.). The secondary screen analysis was carried out on Form I after drying.

Figure 53:
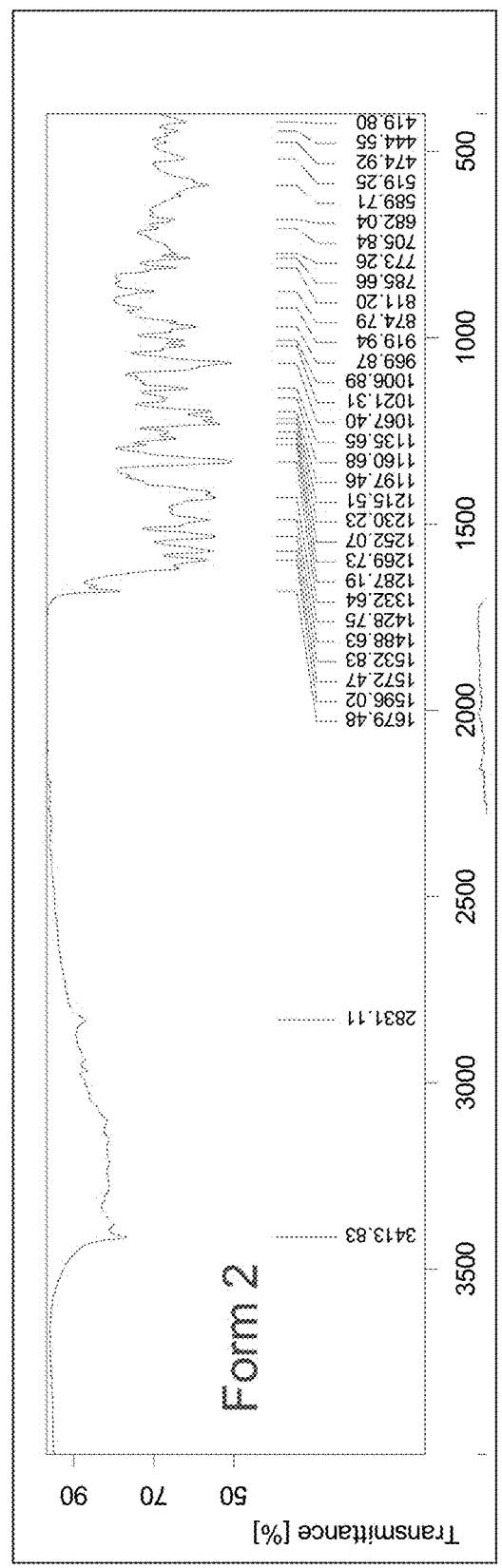
FIG. 53 depicts the IR spectra for Form I of Compound 1.
Figure 54:
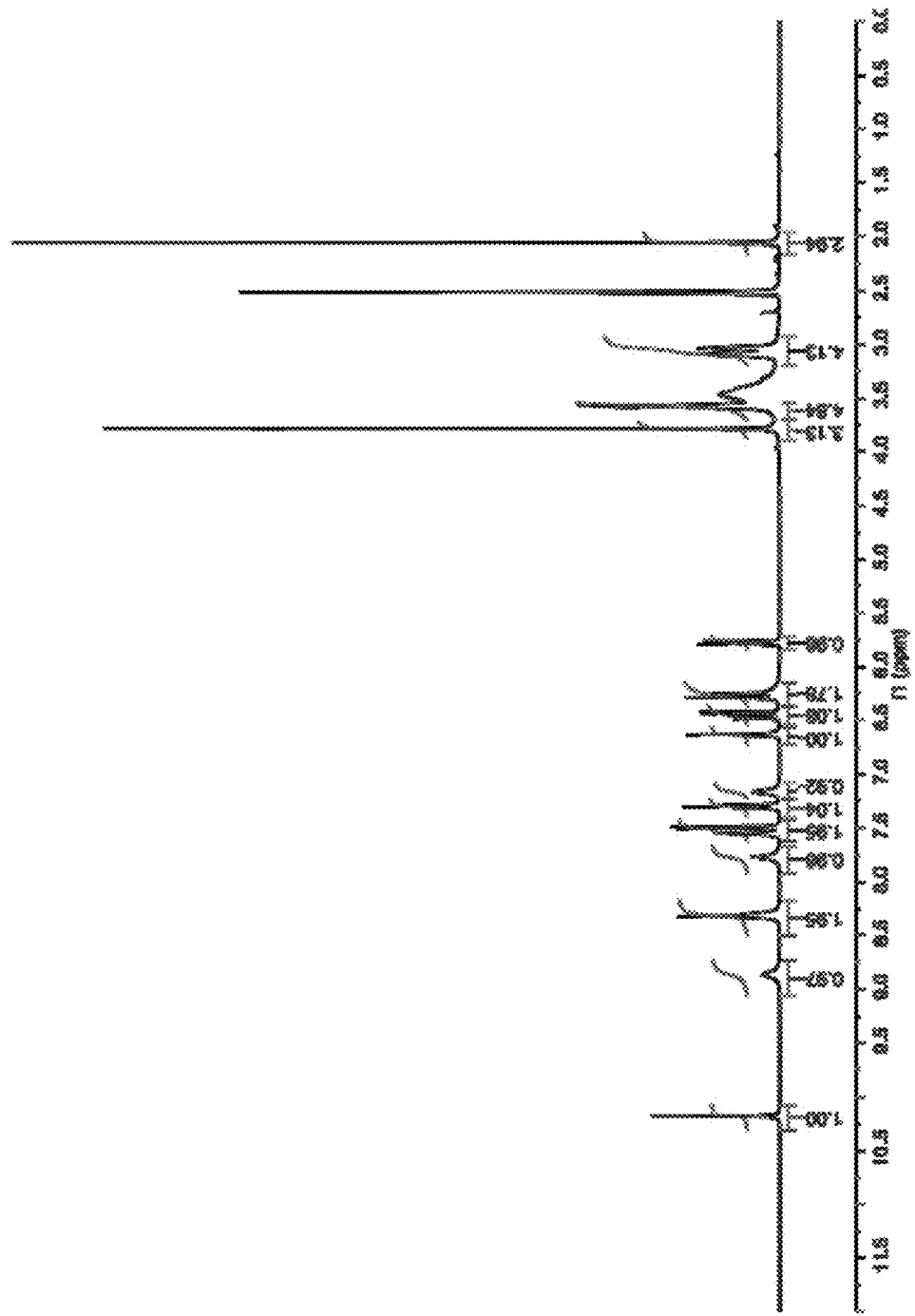
FIG. 54 depicts the ¹H NMR spectrum for Form I of Compound 1.
Figure 55:
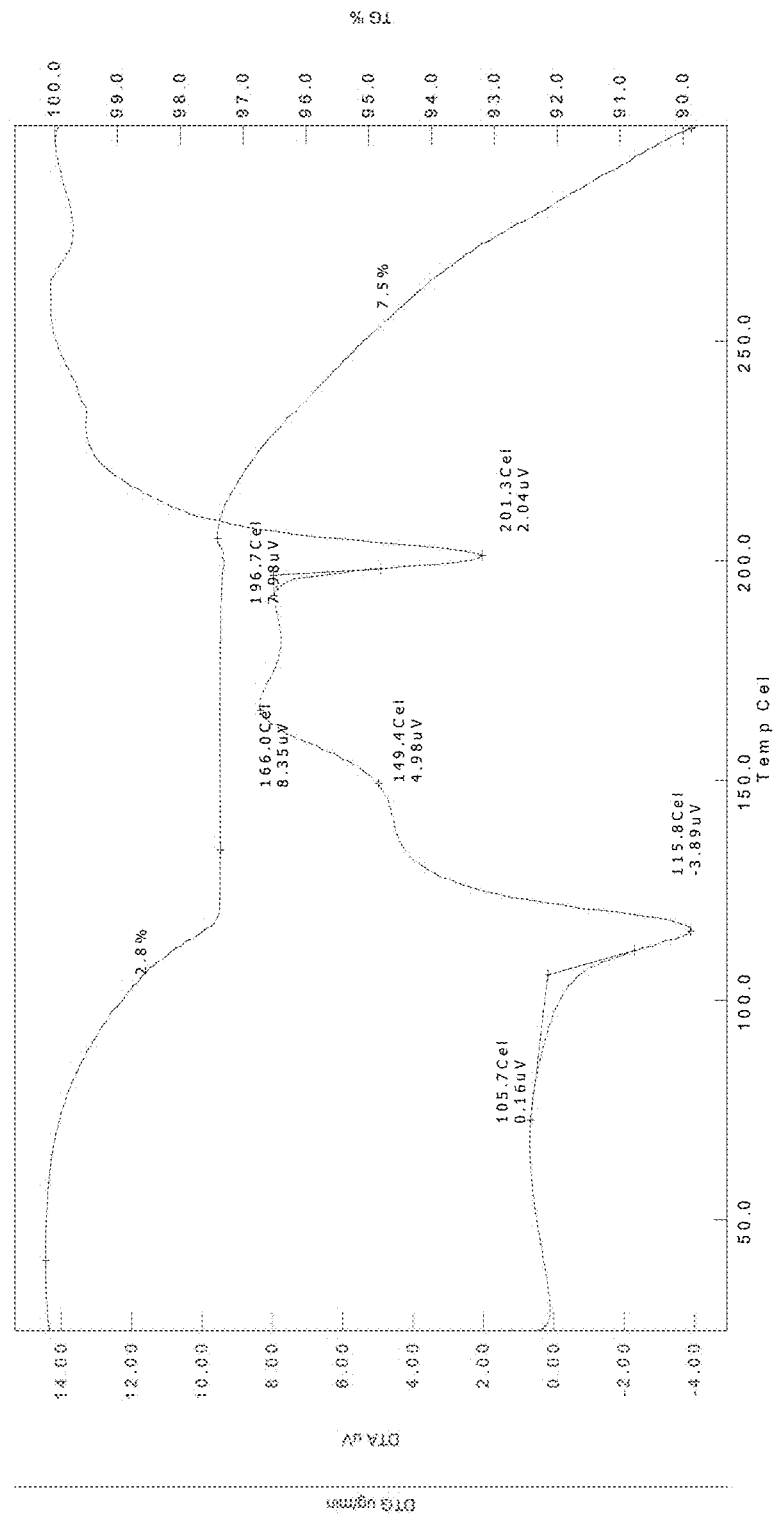
FIG. 55 depicts the TGA/DTA thermogram for Form I of Compound 1 following 3 clays of drying under vacuum.
Figure 56:
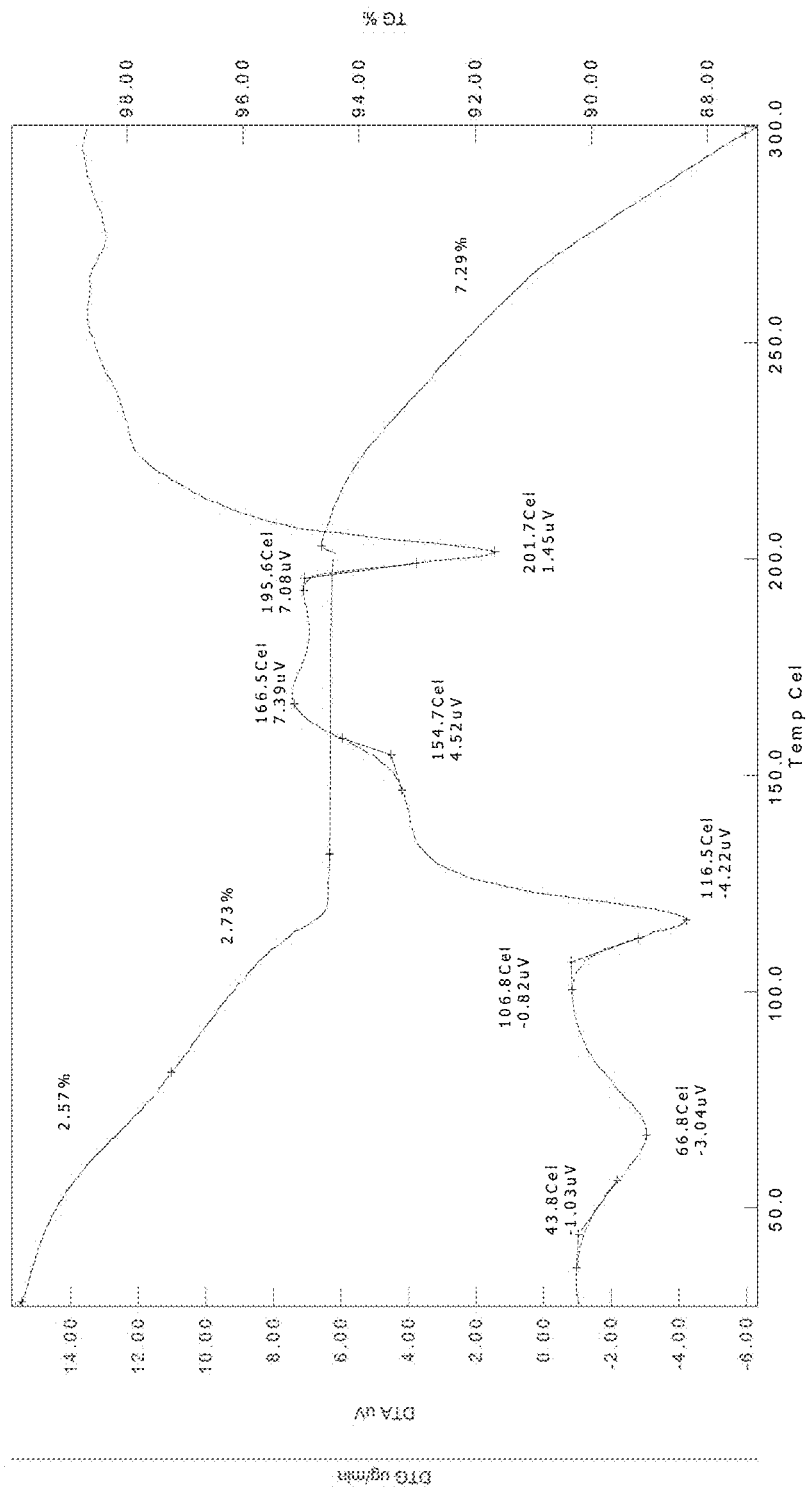
FIG. 56 depicts the TGA/DTA thermogram for Form I of Compound 1 after drying and standing at ambient for ca. 1 hour.
Figure 57:
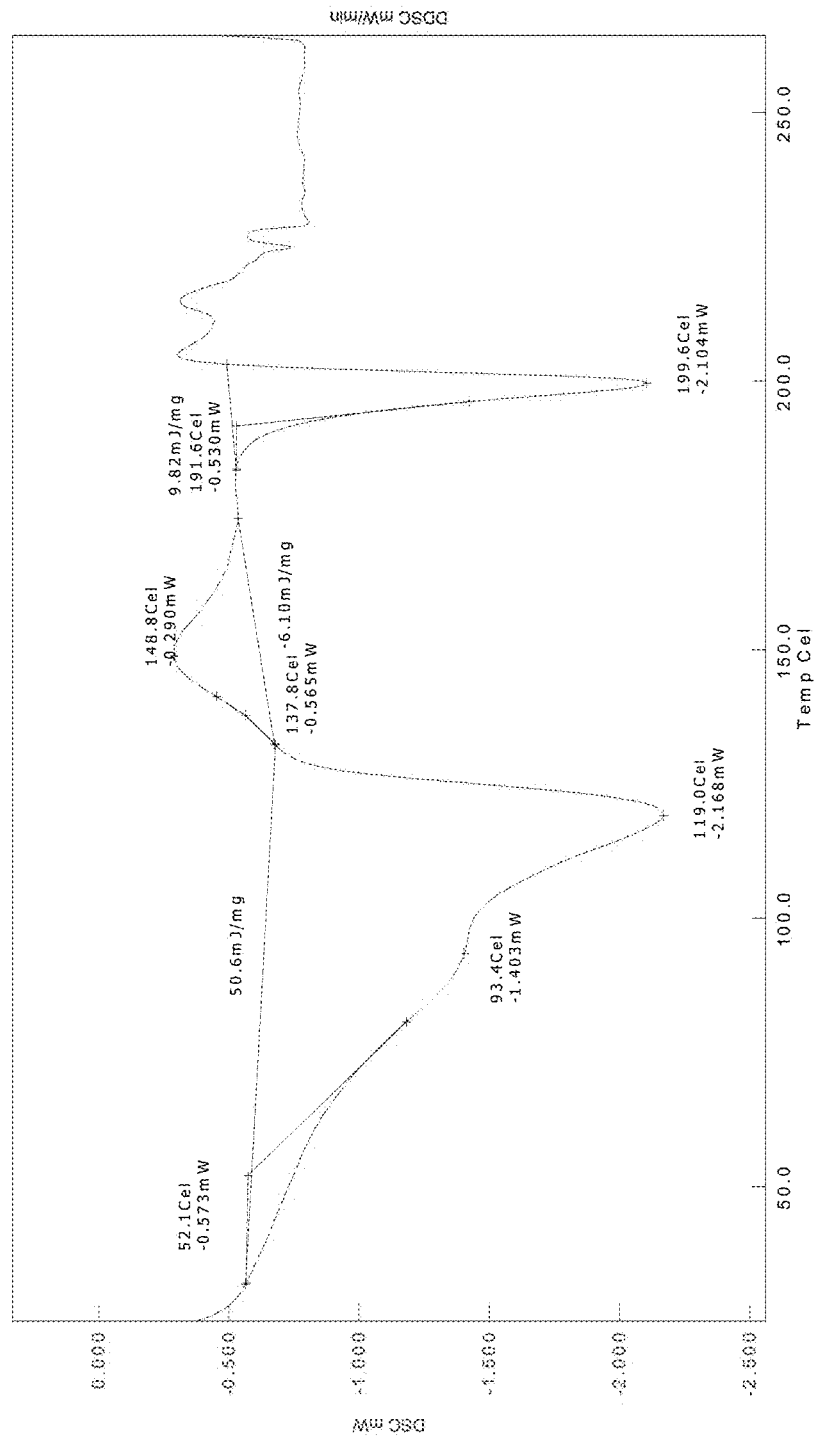
FIG. 57 depicts the DSC thermogram for Form I of Compound 1.
Figure 58:
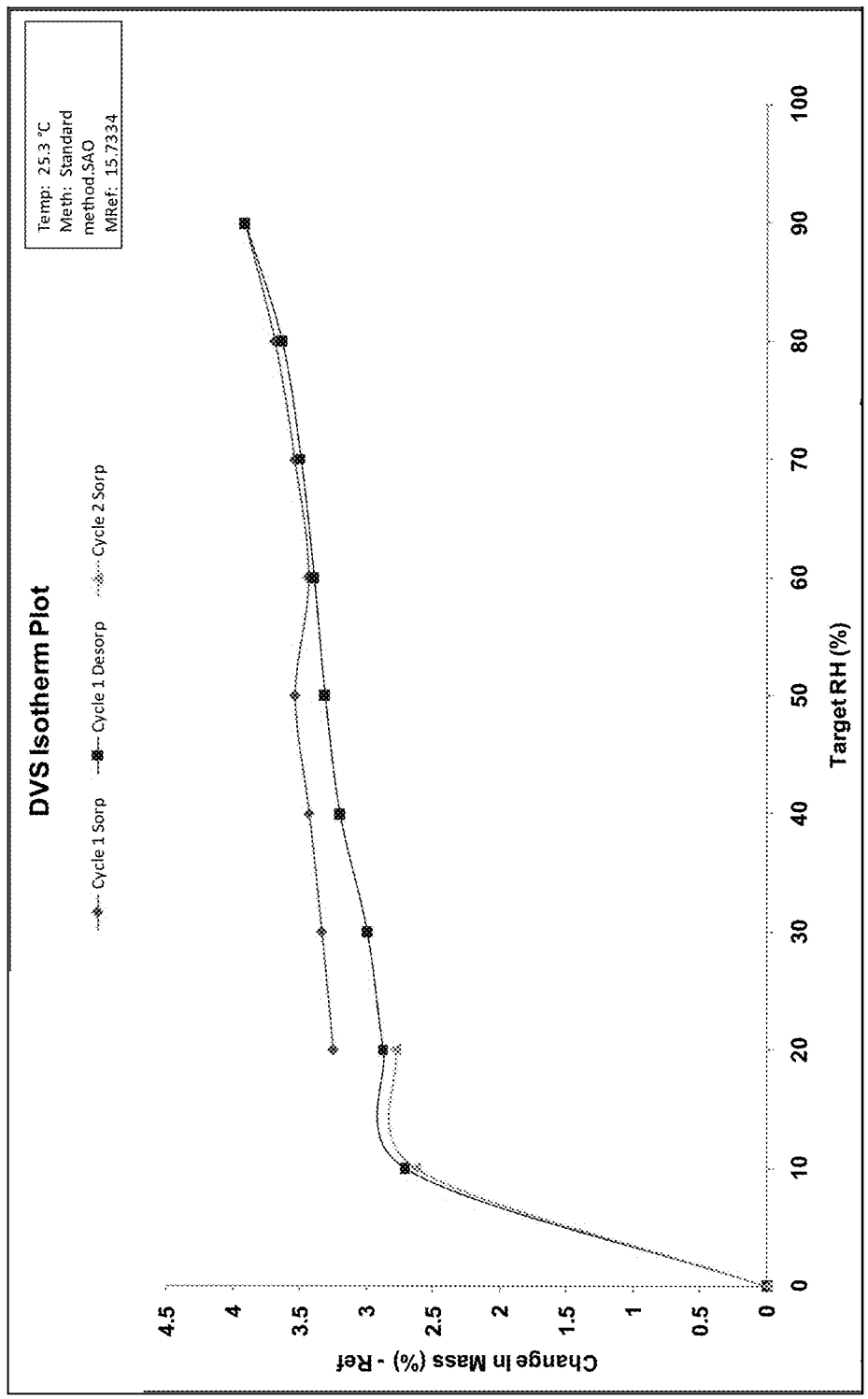
FIG. 58 depicts the DVS analysis for Form I of Compound 1.

Form I was scaled-up for further analysis. During the scale-up, a colour change was observed from yellow to a light beige/cream colour. XRPD analysis (FIG. 52) showed the material produced from scale-up to be crystalline and predominantly consistent with the small scale Form I diffractogram. IR and $^1$H NMR are depicted in FIG. 53 and FIG. 54, respectively. PLM analysis indicated birefringent, fibrous, needle-like crystals when wet. Upon drying the material appeared to lose its needle-like morphology, appearing as small particles with no clearly defined morphology. Hot stage microscopy indicated melting at ca. 135° C. with some recrystallization occurring at ca. 180° C., followed by complete melting by ca. 210° C. After drying under vacuum for ca. 72 hours, the TGA/DTA indicated a weight loss of 2.8% from ca. 80 to 120° C. corresponding with an endotherm in the DTA trace (FIG. 55). An exotherm was observed in the DTA trace at onset ca. 149° C. (peak ca. 166° C.), followed by a further endotherm at onset ca. 197° C. (peak ca. 201° C.). After standing at ambient conditions, the TGA/DTA was re-run showing a weight loss of 2.6% from the outset to ca. 80° C., followed by a further weight loss of 2.8% between ca. 80° C. and 120° C. corresponding with two endotherms in the DTA trace (FIG. 56). An exotherm was then observed in the DTA trace at onset ca. 155° C. (peak ca. 167° C.) followed by a further endotherm at onset ca. 196° C. (peak ca. 202° C.). The DSC analysis indicated overlapping endotherms starting from the outset, followed by an exotherm at onset ca. 138° C. (peak ca. 149° C.) and a further endotherm at onset ca. 92° C. (peak ca. 200° C.) (FIG. 57). DVS analysis (FIG. 58) showed the following observations:

Cycle 1—Sorption 20-90% RH
  Sample gradually takes up ca. 0.66% mass.
Cycle 2—Desorption 90-0% RH
  Between 90-10% RH, sample mass decreases gradually by ca. 1.2%.
  A rapid loss of ca. 2.7% occurs between 10-0% RH,
Cycle 3—Sorption 0-20% RH
  Moisture uptake of ca. 2.8% between 0-20% RH.

Figure 59:
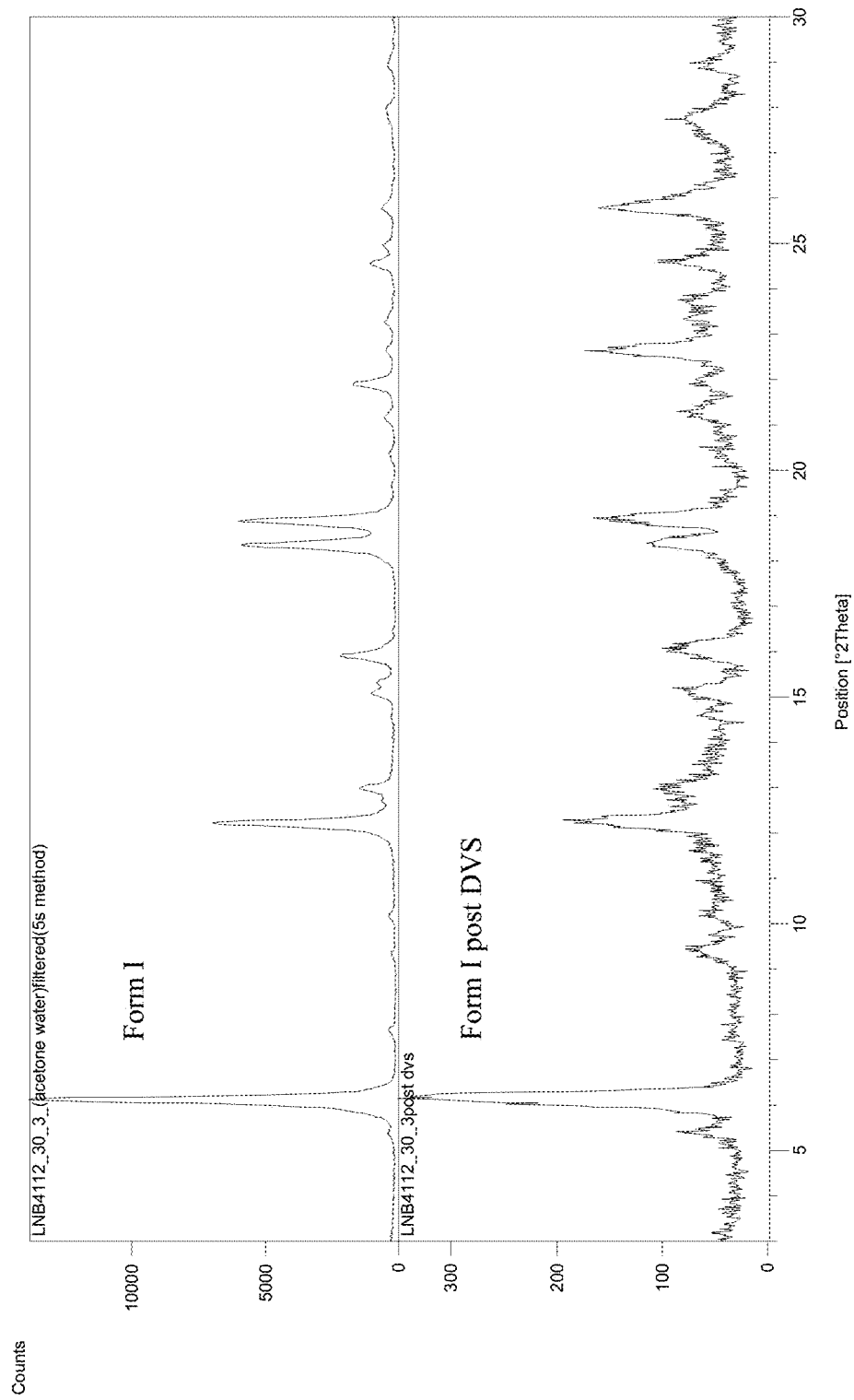
FIG. 59 depicts the Post DVS XRPD analysis for Form I of Compound 1.
Figure 60:
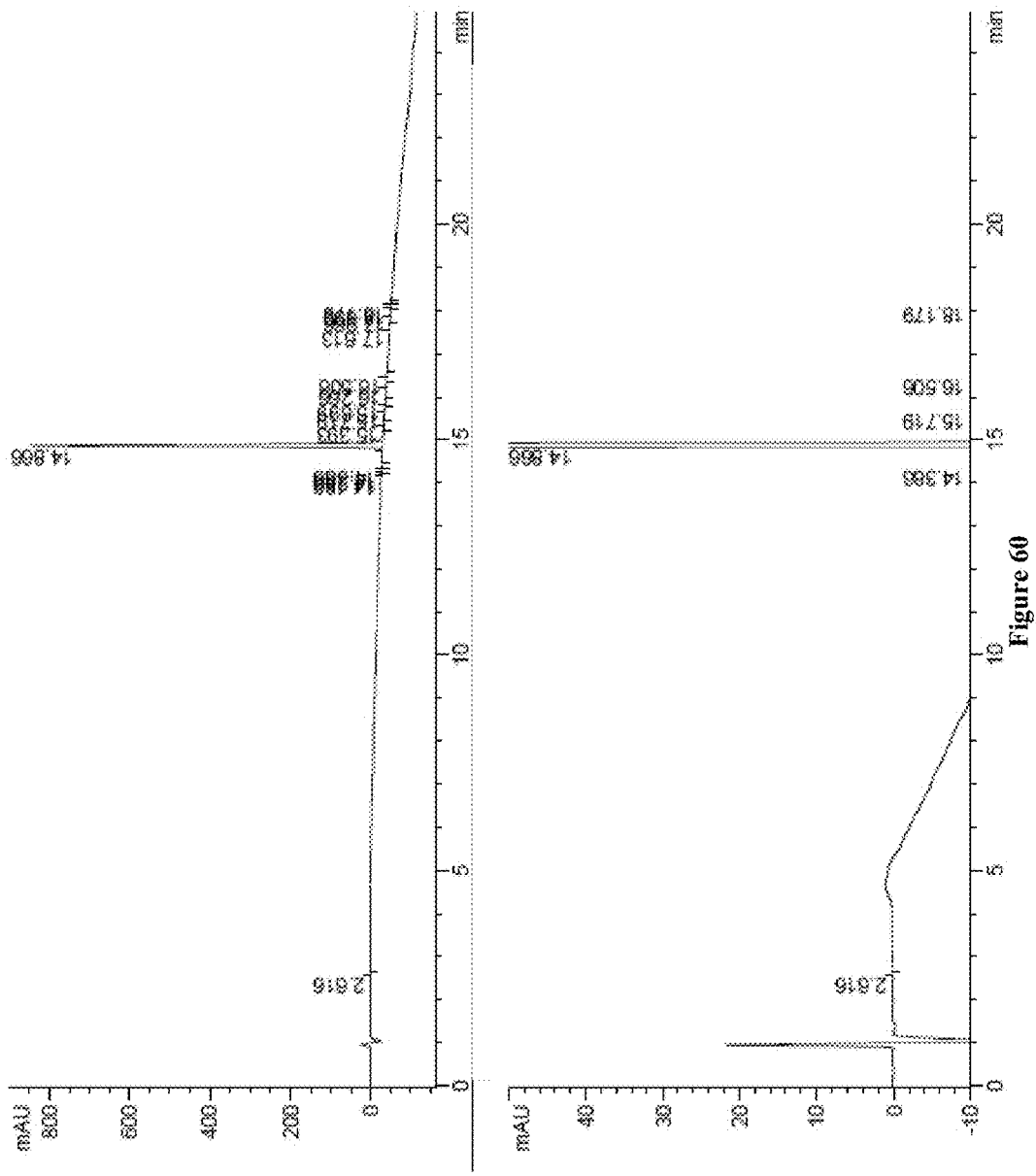
FIG. 60 depicts the HPLC analysis for Form I of Compound 1.
Figure 61:
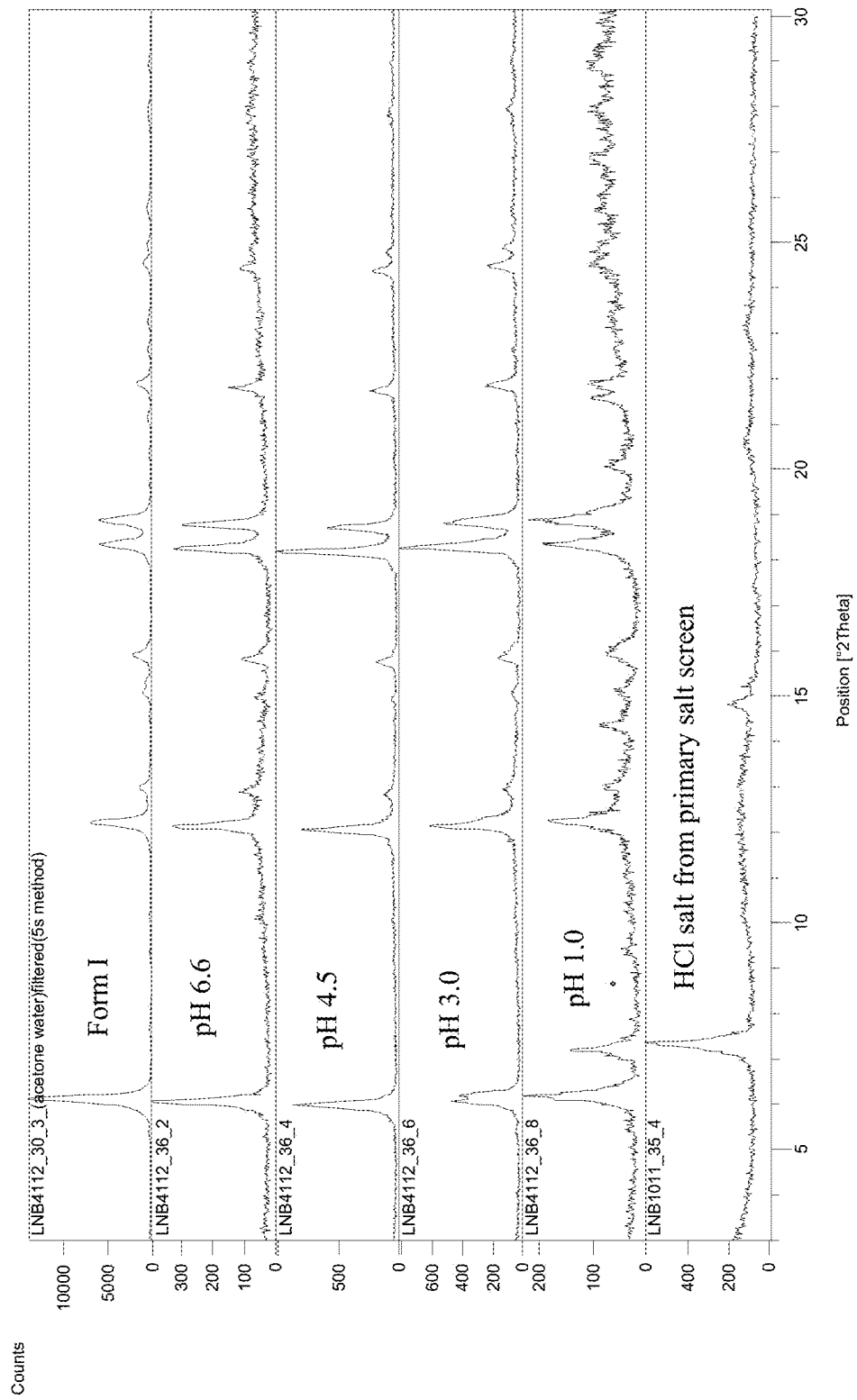
FIG. 61 depicts the XRPD analysis of solids remaining after thermodynamic solubility studies of Form I of Compound 1.

The input material containing ca. 5.6% water appeared to be relatively non-hygroscopic. Approximately 1 equivalent of water was lost at the lower RH percentages. Post DVS XRPD analysis indicated that the material remained as Form I (FIG. 59). No polymorphic form changes were evident. KF analysis indicated the presence of ca. 5.4% water. HPLC purity analysis indicated a purity of ca. 99.66% (FIG. 60). Ion chromatography indicated the presence of 1.64% bromide (ca. 12.57% required for 1 equivalent). XRPD analysis carried out on the thermodynamic solubility experiment solids remaining after 24 hours, indicated that for pH 6.6, 4.5 and 3.0 the material remained as Form I (FIG. 61). For pH 1, the material appeared to be a mixture of Form I and possibly the HCl salt formed during screening.

From the characterisation carried out on Form I, this form was determined to be a hydrated version of the freebase rather than a bromide salt form. The TGA/DTA and DVS data appear to suggest that this may be either a hygroscopic monohydrate or a dihydrate form.

7 Day Stability Studies at 25° C., 80° C., 40° C./75% RH (Open and Closed Conditions).

Figure 62:
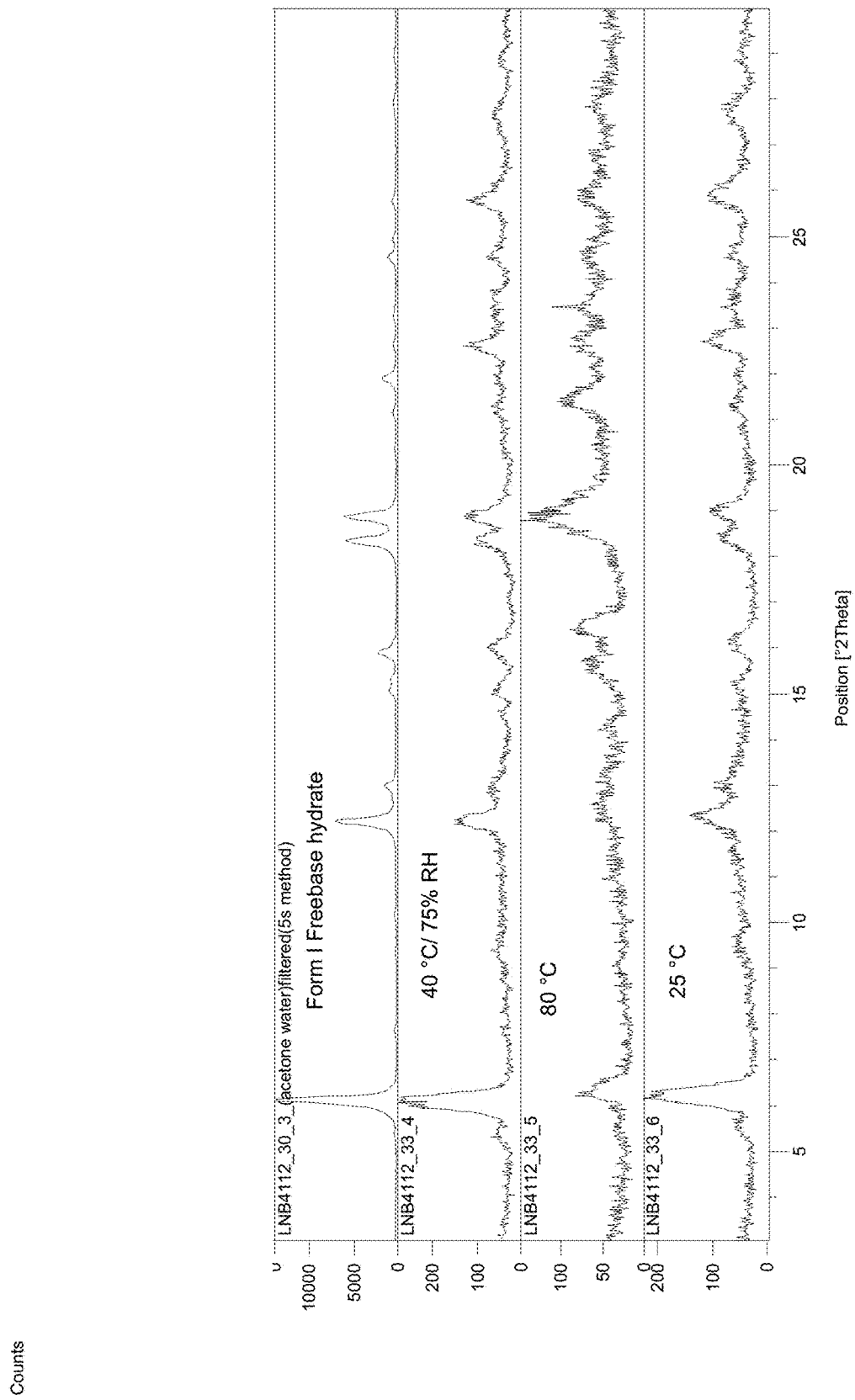
FIG. 62 depicts the XRPD analysis of 1 week stability tests on Form I of Compound 1 using open containers.
Figure 63:
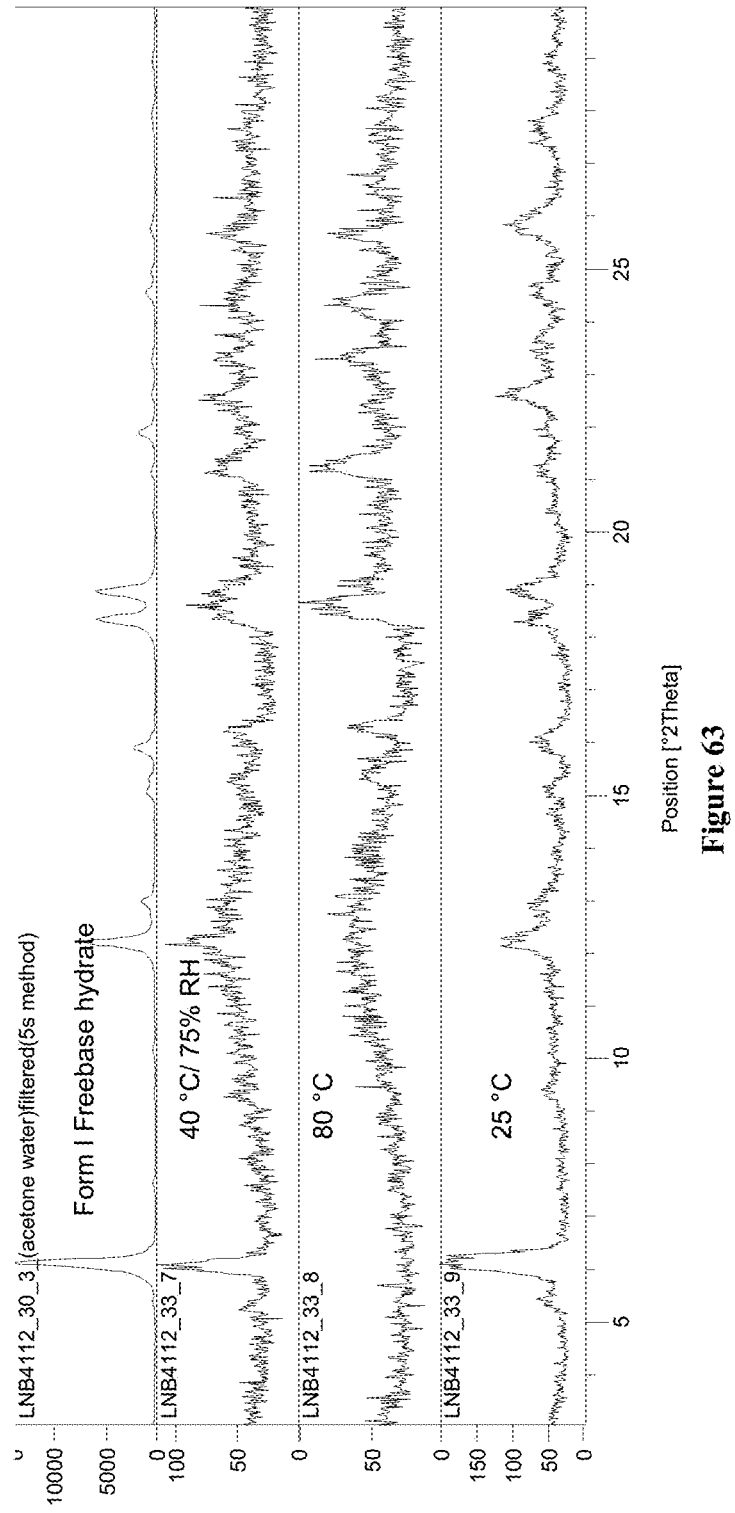
FIG. 63 depicts the XRPD analysis of 1 week stability tests on Form I of Compound 1 using closed containers.

Approximately 15 mg of Form I was placed separately into vials and then exposed to 25° C., 80° C. and 40° C./75% RH environments (open and closed vials) for 1 week to determine stability. The resulting solids were analysed by XRPD and HPLC to establish if any changes had occurred. Results are presented in Tables 2 and 3 and FIGS. 62 and 63.

TABLE 2

1 week stability studies (Open container)

| Condition | Purity | XRPD analysis |
| --- | --- | --- |
| 40° C./75% RH | 98.9% | Form I |
| 80° C. | 98.5% | Form I (some loss in crystallinity) |
| 25° C. | 98.7% | Form I |

TABLE 3

| 1 week stability studies (Closed container) | | |
|---|---|---|
| Condition | Purity | XRPD Analysis |
| 40° C./75% RH | 99.3% | Form I (some loss in crystallinity) |
| 80° C. | 99.2% | Form I (some loss in crystallinity) |
| 25° C. | 99.4% | Form I |

Thermodynamic Solubility Studies.

Slurries of Form I were created in media of various pH (pH 1; pH 3; pH 4.5 and pH 6.6) and shakers for ca. 24 hours. After 24 hours, the slurries were filtered and the solution analysed by HPLC in order to determine the solubility at the various pH levels. For the buffer solutions, KCl/HCl was used for pH 1 and ciliate/phosphate combinations for pH 3, 4.5 and 6.6 (10 mM). The pH of the solutions was also measured prior to HPLC analysis. XRPD analysis was carried out on the remaining solids after 24 hours of shaking. Results are represented in Table 4:

TABLE 4

| Thermodynamic Solubility studies | | |
|---|---|---|
| Buffer pH | pH prior to analysis | Solubility (mg/mL) |
| 1 | 0.95 | 3.266 |
| 3 | 2.26 | 0.023 |
| 4.5 | 3.38 | 0.002 |
| 6.6 | 5.04 | Not detected |

I claim:

1. A composition comprising a solid form of Compound 1:

wherein the solid form of Compound 1 is selected from the group consisting of Form A, Form B, Form C, Form D, Form E, Form F, Form G, Form H, and Form I; and wherein the composition is substantially free of impurities.

2. The composition of claim 1, wherein the composition comprises at least about 90% by weight of the solid form of Compound 1.

3. The composition of claim 2, wherein the composition comprises at least about 95% by weight of the solid form of Compound 1.

4. The composition of claim 3, wherein the composition comprises at least about 97% by weight of the solid form of Compound 1.

5. The composition of claim 4, wherein the composition comprises at least about 98% by weight of the solid form of Compound 1.

6. The composition of claim 5, wherein the composition comprises at least about 99% by weight of the solid form of Compound 1.

7. The composition of claim 6, wherein the composition comprises at least about 99.5% by weight of the solid form of Compound 1.

8. The composition of claim 7, wherein the composition comprises at least about 99.8% by weight of the solid form of Compound 1.

9. The composition of claim 1, wherein the composition contains no more than 5.0 area percent HPLC of total organic impurities relative to the total area of an HPLC chromatogram of the solid form of Compound 1.

10. The composition of claim 9, wherein the composition contains no more than 3.0 area percent HPLC of total organic impurities relative to the total area of an HPLC chromatogram of the solid form of Compound 1.

11. The composition of claim 10, wherein the composition contains no more than 1.5 area percent HPLC of total organic impurities relative to the total area of an HPLC chromatogram of the solid form of Compound 1.

12. The composition of claim 11, wherein the composition contains no more than 1.0 area percent HPLC of total organic impurities relative to the total area of an HPLC chromatogram of the solid form of Compound 1.

13. The composition of claim 12, wherein the composition contains no more than 0.6 area percent HPLC of total organic impurities relative to the total area of an HPLC chromatogram of the solid form of Compound 1.

14. The composition of claim 13, wherein the composition contains no more than 0.5 area percent HPLC of total organic impurities relative to the total area of an HPLC chromatogram of the solid form of Compound 1.

15. A composition comprising Compound 1:

wherein Compound 1 is a crystalline solid form substantially free of an amorphous form of Compound 1.

16. The composition of claim 15, wherein Compound 1 is at least 90% crystalline.

17. The composition of claim 16, wherein Compound 1 is at least 95% crystalline.

18. The composition of claim 17, wherein Compound 1 is at least 97% crystalline.

19. The composition of claim 18, wherein Compound 1 is at least 98% crystalline.

20. The composition of claim 19, wherein Compound 1 is at least 99% crystalline.

* * * * *